(12) United States Patent
Barth et al.

(10) Patent No.: US 9,045,739 B2
(45) Date of Patent: Jun. 2, 2015

(54) IMMUNOKINASES

(75) Inventors: Stefan Barth, Roetgen (DE); Mehmet Kemal Tur, Köln (DE); Michael Stöcker, Aachen (DE); Rainer Fischer, Monschau (DE)

(73) Assignee: Fraunhofer-Gesellschaft Zur Forderung Der Angewandten Forschung E.V., Munich (DE)

( * ) Notice: Subject to any disclaimer, the term of this patent is extended or adjusted under 35 U.S.C. 154(b) by 1530 days.

(21) Appl. No.: 10/586,111

(22) PCT Filed: Jan. 13, 2005

(86) PCT No.: PCT/EP2005/050131
§ 371 (c)(1),
(2), (4) Date: Oct. 12, 2006

(87) PCT Pub. No.: WO2005/068616
PCT Pub. Date: Jul. 28, 2005

(65) Prior Publication Data
US 2009/0136475 A1    May 28, 2009

(30) Foreign Application Priority Data

Jan. 16, 2004 (EP) .................................. 04000847
Jul. 29, 2004 (EP) .................................. 04017928

(51) Int. Cl.
*C12N 5/10* (2006.01)
*C12N 9/12* (2006.01)
*C12N 15/62* (2006.01)

(52) U.S. Cl.
CPC .............. *C12N 9/12* (2013.01); *C07K 2319/01* (2013.01); *C12N 15/62* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,583,034 A | 12/1996 | Green et al. | |
| 5,670,324 A * | 9/1997 | Littman et al. ..................... | 435/6 |
| 5,739,350 A | 4/1998 | Kelly et al. | |
| 5,935,835 A | 8/1999 | Marshall et al. | |
| 6,015,556 A | 1/2000 | Bagshawe | |
| 6,346,406 B1 | 2/2002 | Ryazanov et al. | |
| 2002/0151684 A1 | 10/2002 | Mayer et al. | |
| 2002/0176851 A1 | 11/2002 | Seed et al. | |
| 2003/0104985 A1 | 6/2003 | Matulic-Adamic et al. | |
| 2003/0166512 A1 | 9/2003 | Xie | |
| 2003/0186384 A1 | 10/2003 | Barth et al. | |
| 2003/0198595 A1 | 10/2003 | Goldenberg et al. | |
| 2004/0110928 A1 | 6/2004 | Crisanti et al. | |
| 2004/0204377 A1 | 10/2004 | Rana | |
| 2005/0153915 A1 | 7/2005 | Usman et al. | |
| 2005/0159381 A1 | 7/2005 | McSwiggen et al. | |
| 2005/0176024 A1 | 8/2005 | McSwiggen et al. | |
| 2005/0176025 A1 | 8/2005 | McSwiggen et al. | |
| 2006/0105975 A1 | 5/2006 | Pendergrast et al. | |
| 2006/0280749 A1 | 12/2006 | Rosenblum et al. | |

FOREIGN PATENT DOCUMENTS

| | | |
|---|---|---|
| CA | 2447161 A1 | 11/2002 |
| EP | 1741781 A2 | 1/2001 |
| WO | 98/41648 A2 | 9/1998 |
| WO | 01/80880 A2 | 11/2001 |
| WO | 02/094185 A2 | 11/2002 |
| WO | 2004/031404 | 4/2004 |
| WO | 2004/044141 A2 | 5/2004 |
| WO | 2004/078215 A2 | 9/2004 |
| WO | 2004/104588 A1 | 12/2004 |
| WO | 2005/040379 A2 | 5/2005 |
| WO | 2005/042558 A1 | 5/2005 |
| WO | 2005/059135 A2 | 6/2005 |
| WO | 2005/085470 A1 | 9/2005 |
| WO | 2006/021553 A1 | 3/2006 |
| WO | 2006/114409 A1 | 11/2006 |
| WO | 2007/056153 A2 | 5/2007 |
| WO | 2008/012296 A1 | 1/2008 |

OTHER PUBLICATIONS

Shohat et al ( Biochem and Biophy acta 2002, 1600, pp. 45-50 ).*
Witkowski et al., Biochemistry 38:11643-11650, 1999.*
Kisselev L., Structure, 2002, vol. 10: 8-9.*
Murphy et al (J. Lab clin Med 1194, pp. 255-162, abstract.*
Haxhinasto et al., "Synergistic B Cell Activation by CD40 and the B Cell Antigen Receptor," The Journal of Biological Chemistry, vol. 279, No. 4, pp. 2575-2582, 2004.
Dilber et al., "Intercellular delivery of thymidine kinase prodrug activating enzyme by the herpes simplex virus protein, VP22," Gene Therapy, 6, 12-71, 1999.
Andre et al., "Aptamer-oligonucleotide binding studied by capillary electrophoresis: Cation effect and separation efficiency," Electrophoresis, 26:3247-3255 (2005).
Barth et al., "Compatible-Solute-Supported Periplasmic Expression of Functional Recombinant Proteins under Stress Conditions," Applied and Environmental Microbiology, 66(4):1572-1579 (Apr. 2000).

(Continued)

*Primary Examiner* — Tekchand Saidha
*Assistant Examiner* — Md. Younus Meah
(74) *Attorney, Agent, or Firm* — Dardi & Herbert, PLLC; Curtis B. Herbert

(57) ABSTRACT

A synthetic, soluble, endogenous complex formed from at least one component A and at least one component B, whereby component A comprises a binding domain for extracellular surface structures that internalize upon binding of component A of said complex, and component B has a constitutive catalytic kinase activity and effects cell biosynthesis/signalling including cell death after internalization. The complex allows to influence the growth and the physiology of cells. In particular said complex, nucleic acid molecules encoding it, cells transfected or transformed with these nucleic acid molecules are usable for the preparation of medicaments for the treatment of proliferative diseases, inflammatory diseases, allergies and autoimmune diseases.

8 Claims, 22 Drawing Sheets

(56) References Cited

OTHER PUBLICATIONS

Baskin et al., "Copper-free click chemistry for dynamic in vivo imaging," Proc. Natl. Acad. Sci. USA, 104 (43):16793-16797 (Oct. 23, 2007).

Blank et al., "Aptamers as tools for target validation," Current Opinion in Chemical Biology, 9:336-342 (2005).

Brinkmann et al., "Recombinant immunotoxins for cancer therapy," Expert Opin. Biol. Ther., 1(4):693-702 (2001).

Cassiday et al., "Yeast genetic selections to optimize RNA decoys for transcription factor NF-kB," PNAS, 100(7):3930-3935 (Apr. 1, 2003).

Chaudhary et al., "A rapid method of cloning functional variable-region antibody genes in Escherichia coli as single-chain immunotoxins," Proc. Natl. Acad. Sci. USA, 87:1066-1070 (1990).

Chiu et al., "Visualizing a Correlation between siRNA Localization, Cellular Uptake, and RNAi in Living Cells," Chemistry & Biology, 11:1165-1175 (Aug. 2004).

Crooke, "Antisense Strategies," Current Molecular Medicine, 4:465-487 (2004).

Dyba et al., "Small molecule toxins targeting tumor receptors," Current Pharmaceutical Design, 10:2311-2334 (2004).

Dykxhoorn et al., "Killing the Messenger: Short RNAs that Silence Gene Expression," Nature Reviews Molecular Cell Biology, 4:457-467 (Jun. 2003).

Dykxhoorn et al., "The silent treatment: siRNAs as small molecule drugs," Gene Therapy, 13:541-552 (2006).

Farokhzad et al., "Nanoparticle-Aptamer Bioconjugates: A New Approach for Targeting Prostate Cancer Cells," Cancer Research, 64:7668-7672 (Nov. 1, 2004).

Hochuli, "Large-scale chromatography of recombinant proteins," Journal of Chromatography, 444:293-302. (1988).

Izquierdo, "Short interfering RNAs as a tool for cancer gene therapy," Cancer Gene Therapy, 12:217-227 (2005).

Kaminski et al., "Iodine-131-Anti-B1 Radioimmunotherapy for B-Cell Lymphoma," Journal of Clinical Oncology, 14 (7):1974-1981 (Jul. 1996).

Kapp et al., "Preliminary report: Growth of Hodgkin's lymphoma derived cells in immune compromised mice," Annals of Oncology, 3 (Suppl. 4): S21-S23 (1992).

Karkare et al., "RNA Interference Silencing the Transcriptional Message," Applied Biochemistry and Biotechnology, 119:1-12 (2004).

Keppler et al., "Labeling of fusion proteins of 06-alkylguanine-DNA alkyltransferase with small molecules in vivo and in vitro," Methods, 32:437-444 (2004).

Khaled et al., "Controllable Self-Assembly of Nanoparticles for Specific Delivery of Multiple Therapeutic Molecules to Cancer Cells Using RNA Nanotechnology," Nano Letters, 5(9):1797-1808 (2005).

Leclercq et al., "Cellular Signalling by Sphingosine Kinase and Sphingosine 1-Phosphate," IUBMB Life, 58(8):467-472 (Aug. 2006).

Lim et al., "Synthesis of Water-Soluble Dendrimers Based on Melamine Bearing 16 Paclitaxel Groups," Organic Letters, 10(2):201-204 (2008).

Lorenz et al., "Steroid and lipid conjugates of siRNAs to enhance cellular uptake and gene silencing in liver cells", Bioorganic & Medicinal Chemistry Letters, 14:4975-4977 (2004).

Meyer et al., "FRET imaging reveals that functional neurokinin-1 receptors are monomeric and reside in membrane microdomains of live cells," PNAS US, 103 (7):2138-2143 (Feb. 14, 2006).

Niemeyer et al., "Detecting antigens by quantitative immuno-PCR," Nature Protocols, 2(8):1918-1930 (2007).

Pennell et al., "Designing Immunotoxins for Cancer Therapy," Immunologic Research, 25(2):177-191 (2002).

Porath et al., "Metal chelate affinity chromatography, a new approach to protein fractionation," Nature, 258:598-599 (Dec. 18, 1975).

Molecular Cloning: A Laboratory Manual (Third Edition) by Joseph Sambrook et al. (1 page).

Scanlon, "Anti-Genes: siRNA, Ribozymes and Antisense," Current Pharmaceutical Biotechnology, 5:415-420 (2004).

Selzer et al., "N-ras inhibits apoptosis in human melanoma grown in SCID mice by reciprocal regulation of BCL-2 and the BCL-2 associated protein bax," Poster 179, Radiotherapy and Oncology, 40:S48 (1996).

Song et al., "Antibody mediated in vivo delivery of small interfering RNAs via cell-surface receptors," Nature Biotechnology, 23(6):709-717 (Jun. 2005).

Soutschek et al., "Therapeutic silencing of an endogenous gene by systemic administration of modified siRNAs," Nature, 432:173-178 (Nov. 11, 2004).

Steinborn et al., "Application of a wide-range yeast vector (CoMed) system to recombinant protein production in dimorphic Arxula adeninivorans, methylotrophic Hansenula polymorpha and other yeasts," Microbial Cell Factories, 5:33 (2006) (13 pages).

Stocker et al., "Secretion of functional anti-CD30-angiogenin immunotoxins into the supernatant of transfected 293T-cells," Protein Expression and Purification, 28:211-219 (2003).

Thorpe et al., "Chemokine/chemokine receptor nomenclature: IUIS/WHO Subcommitte on Chemokine Nomenclature," Cytokine, 21:48-49 (2003).

Tur et al., "Recombinant CD64-Specific Single Chain Immunotoxin Exhibits Specific Cytotoxicity against Acute Myeloid Leukemia Cells," Cancer Research, 63:8414-8419 (Dec. 1, 2003).

Wadhwa et al, "Know-how of RNA interference and its applications in research and therapy," Mutation Research, 567:71-84 (2004).

Wu et al., "Arming Antibodies: prospects and challenges for immunoconjugates," Nature Biotechnology, 23(9):1137-1146 (Sep. 2005).

Wu et al., "Targeted delivery of methotrexate to epidermal growth factor receptor-positive brain tumors by means of cetuximab (IMC-C225) dendrimer bioconjugates," Mol. Cancer Ther., 5(1):52-59 (Jan. 2006).

Dufner et al., "Harnessing phage and ribosome display for antibody optimisation," TRENDS in Biotechnology 24 (11):523-529 (2006).

Kampmeier et al., "Rapid optical imaging of EGF receptor expression with a single-chain antibody SNAP-tag fusion protein," Eur J Nucl Med Mol Imaging 37:1926-1934 (2010).

Riemer et al., "Matching of trastuzumab (Herceptin®) epitope mimics onto the surface of Her-2/neu—a new method of epitope definition," Molecular Immunology 42:1121-1124 (2005).

Stancovski et al, "Mechanistic aspects of the opposing effects of monoclonal antibodies to the ERBB2 receptor on tumor growth," Proc. Natl. Acad. Sci. USA 88:8691-8695 (Oct. 1991).

Witte et al., "Monoclonal antibodies trageting the VEGF receptor-2 (Flk1/KDR) as an anti-angiogenic therapeutic strategy," Cancer and Metastasis Reviews 17:155-161 (1998).

Wu et al., "Humanization of a Murine Monoclonal Antibody by Simultaneous Optimization of Framework and CDR Residues," J. Mol. Biol. 294:151-162 (1999).

Yu et al., "Interaction between Bevacizumab and Murine VEGF-A: A Reassessment," Investigative Opthamology & Visual Science, 49(2):522-527 (Feb. 2008).

* cited by examiner

```
atg gag aca gac aca ctc ctg cta tgg gta ctg ctg ctc tgg gtt cca    48
Met Glu Thr Asp Thr Leu Leu Leu Trp Val Leu Leu Leu Trp Val Pro
 1               5                  10                  15 ggt tcc act ggt gac tct aga atg gtc cag gcc tcg atg agg agc cca    96
Gly Ser Thr Gly Asp Ser Arg Met Val Gln Ala Ser Met Arg Ser Pro
            20                  25                  30 aat atg gag acg ttc aaa cag cag aag gtg gag gac ttt tat gat att   144
Asn Met Glu Thr Phe Lys Gln Gln Lys Val Glu Asp Phe Tyr Asp Ile
        35                  40                  45 gga gag gag ctg ggc agt ggc cag ttt gcc atc gtg aag aag tgc cgg   192
Gly Glu Glu Leu Gly Ser Gly Gln Phe Ala Ile Val Lys Lys Cys Arg
    50                  55                  60 gag aag agc acg ggg ctg gag tat gca gcc aag ttc att aag aag agg   240
Glu Lys Ser Thr Gly Leu Glu Tyr Ala Ala Lys Phe Ile Lys Lys Arg
65                  70                  75                  80 cag agc cgg gcc agc cgt cgg ggc gtg tgc cgg gag gaa atc gag cgg   288
Gln Ser Arg Ala Ser Arg Arg Gly Val Cys Arg Glu Glu Ile Glu Arg
        85                  90                  95 gag gtg agc atc ctg cgg cag gtg ctg cac ccc aac atc atc acg ctg   336
Glu Val Ser Ile Leu Arg Gln Val Leu His Pro Asn Ile Ile Thr Leu
            100                 105                 110 cac gac gtc tat gag aac cgc acc gac gtg gtg ctc atc ctt gag cta   384
His Asp Val Tyr Glu Asn Arg Thr Asp Val Val Leu Ile Leu Glu Leu
        115                 120                 125 gtg tcc gga gga gaa ctg ttt gat ttc ctg gcc cag aag gag tcg tta   432
Val Ser Gly Gly Glu Leu Phe Asp Phe Leu Ala Gln Lys Glu Ser Leu
    130                 135                 140 agt gag gag gaa gcc acc agc ttc att aag cag atc ctg gat ggg gtg   480
Ser Glu Glu Glu Ala Thr Ser Phe Ile Lys Gln Ile Leu Asp Gly Val
145                 150                 155                 160 aat tac ctt cac aca aag aaa att gct cac ttt gat ctc aag cca gaa   528
Asn Tyr Leu His Thr Lys Lys Ile Ala His Phe Asp Leu Lys Pro Glu
        165                 170                 175 aac atc atg ttg tta gac aag aat atc cca att cca cac atc aag ctg   576
Asn Ile Met Leu Leu Asp Lys Asn Ile Pro Ile Pro His Ile Lys Leu
            180                 185                 190 att gac ttt ggc ctg gct cac gaa ata gaa gat gga gtt gaa ttt aaa   624
Ile Asp Phe Gly Leu Ala His Glu Ile Glu Asp Gly Val Glu Phe Lys
        195                 200                 205 aac att ttt ggg aca cct gaa ttt gtt gct cca gaa atc gtg aac tat   672
Asn Ile Phe Gly Thr Pro Glu Phe Val Ala Pro Glu Ile Val Asn Tyr
    210                 215                 220 gag cca ctg gga ctg gag gcc gac atg tgg agc att gga gtc atc acc   720
Glu Pro Leu Gly Leu Glu Ala Asp Met Trp Ser Ile Gly Val Ile Thr
225                 230                 235                 240
```

FIG. 5A

| | | | | | | | | | | | | | | | |
|---|---|---|---|---|---|---|---|---|---|---|---|---|---|---|---|
| tat | atc | ctt | cta | agt | gga | gcg | tcc | ccc | ttc | ctg | gga | gac | aca | aaa | caa | 768 |
| Tyr | Ile | Leu | Leu | Ser | Gly | Ala | Ser | Pro | Phe | Leu | Gly | Asp | Thr | Lys | Gln | |
| | | | | 245 | | | | 250 | | | | | 255 | | | |

```
tat atc ctt cta agt gga gcg tcc ccc ttc ctg gga gac aca aaa caa     768
Tyr Ile Leu Leu Ser Gly Ala Ser Pro Phe Leu Gly Asp Thr Lys Gln
                245             250                 255 gaa acc ctg gca aat atc act gct gtg agt tac gac ttt gat gag gaa     816
Glu Thr Leu Ala Asn Ile Thr Ala Val Ser Tyr Asp Phe Asp Glu Glu
                260             265                 270 ttc ttc agc cag aca agc gag ctg gcc aag gac ttc att cgg aag ctt     864
Phe Phe Ser Gln Thr Ser Glu Leu Ala Lys Asp Phe Ile Arg Lys Leu
                275             280                 285 ctt gtg aaa gag acc cgg aaa cgg ctt acc atc caa gag gct ctc aga     912
Leu Val Lys Glu Thr Arg Lys Arg Leu Thr Ile Gln Glu Ala Leu Arg
                290             295                 300 cat ccc tgg atc gga tcc aaa cta gct gag cac gaa ggt gac gcg gcc     960
His Pro Trp Ile Gly Ser Lys Leu Ala Glu His Glu Gly Asp Ala Ala
305                 310             315                 320 cag ccg gcc atg gcc cag gtc aag ctg cag gag tca ggg act gaa ctg    1008
Gln Pro Ala Met Ala Gln Val Lys Leu Gln Glu Ser Gly Thr Glu Leu
                325             330                 335 gca aag cct ggg gcc gca gtg aag atg tcc tgc aag gct tct ggc tac    1056
Ala Lys Pro Gly Ala Ala Val Lys Met Ser Cys Lys Ala Ser Gly Tyr
                340             345                 350 acc ttt act gac tac tgg atg cac tgg gtt aaa cag agg cct gga cag    1104
Thr Phe Thr Asp Tyr Trp Met His Trp Val Lys Gln Arg Pro Gly Gln
                355             360                 365 ggt ctg gaa tgg att gga tac att aat cct aac act gct tat act gac    1152
Gly Leu Glu Trp Ile Gly Tyr Ile Asn Pro Asn Thr Ala Tyr Thr Asp
370                 375             380 tac aat cag aaa ttc aag gac aag gcc aca ttg act gca gac aaa tcc    1200
Tyr Asn Gln Lys Phe Lys Asp Lys Ala Thr Leu Thr Ala Asp Lys Ser
385                 390             395                 400 tcc agc aca gcc tac atg caa ctg cgc agc ctg acc tct gag gat tct    1248
Ser Ser Thr Ala Tyr Met Gln Leu Arg Ser Leu Thr Ser Glu Asp Ser
                405             410                 415 gca gtc tat tac tgt gca aaa aag aca act cag act acg tgg ggg ttt    1296
Ala Val Tyr Tyr Cys Ala Lys Lys Thr Thr Gln Thr Thr Trp Gly Phe
                420             425                 430 cct ttt tgg ggc caa ggg acc acg gtc acc gtc tcc tca ggt gga ggc    1344
Pro Phe Trp Gly Gln Gly Thr Thr Val Thr Val Ser Ser Gly Gly Gly
                435             440                 445 ggt tca ggc gga ggt ggc tct ggt ggt gga tcg gac att gtg ctg        1392
Gly Ser Gly Gly Gly Gly Ser Gly Gly Gly Gly Ser Asp Ile Val Leu
450                 455             460 acc cag tct cca aaa tcc atg gcc atg tca gtc gga gag agg gtc acc    1440
Thr Gln Ser Pro Lys Ser Met Ala Met Ser Val Gly Glu Arg Val Thr
465                 470             475                 480
```

FIG. 5B

```
ttg agc tgc aag gcc agt gag aat gtg gat tct ttt gtt tcc tgg tat    1488
Leu Ser Cys Lys Ala Ser Glu Asn Val Asp Ser Phe Val Ser Trp Tyr
            485                 490                 495 caa cag aaa cca ggc cag tct cct aaa ctg ctg ata tac ggg gcc tcc    1536
Gln Gln Lys Pro Gly Gln Ser Pro Lys Leu Leu Ile Tyr Gly Ala Ser
            500                 505                 510 aac cgg tac act ggg gtc ccc gat cgc ttc gca ggc agt gga tct gga    1584
Asn Arg Tyr Thr Gly Val Pro Asp Arg Phe Ala Gly Ser Gly Ser Gly
            515                 520                 525 aga gat ttc act ctg acc atc agc agt gtg cag gct gaa gac ctt gca    1632
Arg Asp Phe Thr Leu Thr Ile Ser Ser Val Gln Ala Glu Asp Leu Ala
            530                 535                 540 gat tat cac tgt gga cag aat tac agg tat ccg ctc acg ttc ggt gct    1680
Asp Tyr His Cys Gly Gln Asn Tyr Arg Tyr Pro Leu Thr Phe Gly Ala
545                 550                 555                 560 ggc acc aag ctg gaa atc aaa cgg gcg gcc gca ggg ccc gaa caa aaa    1728
Gly Thr Lys Leu Glu Ile Lys Arg Ala Ala Ala Gly Pro Glu Gln Lys
            565                 570                 575 ctc atc tca gaa gag gat ctg aat agc gcc gtc gac cat cat cat cat    1776
Leu Ile Ser Glu Glu Asp Leu Asn Ser Ala Val Asp His His His His
            580                 585                 590 cat cat tga                                                        1785
His His
            595
```

FIG. 5C

```
Met Glu Thr Asp Thr Leu Leu Leu Trp Val Leu Leu Leu Trp Val Pro
 1           5                   10                  15
Gly Ser Thr Gly Asp Ser Arg Met Val Gln Ala Ser Met Arg Ser Pro
             20                  25                  30
Asn Met Glu Thr Phe Lys Gln Gln Lys Val Glu Asp Phe Tyr Asp Ile
             35                  40                  45
Gly Glu Glu Leu Gly Ser Gly Gln Phe Ala Ile Val Lys Lys Cys Arg
 50                  55                  60
Glu Lys Ser Thr Gly Leu Glu Tyr Ala Ala Lys Phe Ile Lys Lys Arg
 65                  70                  75                  80
Gln Ser Arg Ala Ser Arg Arg Gly Val Cys Arg Glu Glu Ile Glu Arg
             85                  90                  95
Glu Val Ser Ile Leu Arg Gln Val Leu His Pro Asn Ile Ile Thr Leu
             100                 105                 110
His Asp Val Tyr Glu Asn Arg Thr Asp Val Val Leu Ile Leu Glu Leu
             115                 120                 125
Val Ser Gly Gly Glu Leu Phe Asp Phe Leu Ala Gln Lys Glu Ser Leu
 130                 135                 140
Ser Glu Glu Glu Ala Thr Ser Phe Ile Lys Gln Ile Leu Asp Gly Val
 145                 150                 155                 160
Asn Tyr Leu His Thr Lys Lys Ile Ala His Phe Asp Leu Lys Pro Glu
             165                 170                 175
Asn Ile Met Leu Leu Asp Lys Asn Ile Pro Ile Pro His Ile Lys Leu
             180                 185                 190
Ile Asp Phe Gly Leu Ala His Glu Ile Glu Asp Gly Val Glu Phe Lys
             195                 200                 205
Asn Ile Phe Gly Thr Pro Glu Phe Val Ala Pro Glu Ile Val Asn Tyr
 210                 215                 220
Glu Pro Leu Gly Leu Glu Ala Asp Met Trp Ser Ile Gly Val Ile Thr
 225                 230                 235                 240
Tyr Ile Leu Leu Ser Gly Ala Ser Pro Phe Leu Gly Asp Thr Lys Gln
             245                 250                 255
Glu Thr Leu Ala Asn Ile Thr Ala Val Ser Tyr Asp Phe Asp Glu Glu
             260                 265                 270
Phe Phe Ser Gln Thr Ser Glu Leu Ala Lys Asp Phe Ile Arg Lys Leu
             275                 280                 285
Leu Val Lys Glu Thr Arg Lys Arg Leu Thr Ile Gln Glu Ala Leu Arg
 290                 295                 300
His Pro Trp Ile Gly Ser Lys Leu Ala Glu His Glu Gly Asp Ala Ala
 305                 310                 315                 320
Gln Pro Ala Met Ala Gln Val Lys Leu Gln Glu Ser Gly Thr Glu Leu
             325                 330                 335
Ala Lys Pro Gly Ala Ala Val Lys Met Ser Cys Lys Ala Ser Gly Tyr
             340                 345                 350
Thr Phe Thr Asp Tyr Trp Met His Trp Val Lys Gln Arg Pro Gly Gln
             355                 360                 365
Gly Leu Glu Trp Ile Gly Tyr Ile Asn Pro Asn Thr Ala Tyr Thr Asp
 370                 375                 380
Tyr Asn Gln Lys Phe Lys Asp Lys Ala Thr Leu Thr Ala Asp Lys Ser
 385                 390                 395                 400
Ser Ser Thr Ala Tyr Met Gln Leu Arg Ser Leu Thr Ser Glu Asp Ser
             405                 410                 415
Ala Val Tyr Tyr Cys Ala Lys Lys Thr Thr Gln Thr Thr Trp Gly Phe
             420                 425                 430
Pro Phe Trp Gly Gln Gly Thr Thr Val Thr Val Ser Ser Gly Gly Gly
             435                 440                 445
Gly Ser Gly Gly Gly Gly Ser Gly Gly Gly Gly Ser Asp Ile Val Leu
 450                 455                 460
```

FIG. 6A

```
Thr Gln Ser Pro Lys Ser Met Ala Met Ser Val Gly Glu Arg Val Thr
465                 470                 475                 480
Leu Ser Cys Lys Ala Ser Glu Asn Val Asp Ser Phe Val Ser Trp Tyr
                485                 490                 495
Gln Gln Lys Pro Gly Gln Ser Pro Lys Leu Leu Ile Tyr Gly Ala Ser
                500                 505                 510
Asn Arg Tyr Thr Gly Val Pro Asp Arg Phe Ala Gly Ser Gly Ser Gly
            515                 520                 525
Arg Asp Phe Thr Leu Thr Ile Ser Ser Val Gln Ala Glu Asp Leu Ala
    530                 535                 540
Asp Tyr His Cys Gly Gln Asn Tyr Arg Tyr Pro Leu Thr Phe Gly Ala
545                 550                 555                 560
Gly Thr Lys Leu Glu Ile Lys Arg Ala Ala Ala Gly Pro Glu Gln Lys
                565                 570                 575
Leu Ile Ser Glu Glu Asp Leu Asn Ser Ala Val Asp His His His His
                580                 585                 590
His His
```

FIG. 6B

```
atg gag aca gac aca ctc ctg cta tgg gta ctg ctc tgg gtt cca         48
Met Glu Thr Asp Thr Leu Leu Leu Trp Val Leu Leu Trp Val Pro
 1               5                  10                  15 ggt tcc act ggt gac gcg gcc cag ccg gcc atg gcc cag gtc aag ctg     96
Gly Ser Thr Gly Asp Ala Ala Gln Pro Ala Met Ala Gln Val Lys Leu
                 20                  25                  30 cag gag tca ggg act gaa ctg gca aag cct ggg gcc gca gtg aag atg    144
Gln Glu Ser Gly Thr Glu Leu Ala Lys Pro Gly Ala Ala Val Lys Met
         35                  40                  45 tcc tgc aag gct tct ggc tac acc ttt act gac tac tgg atg cac tgg    192
Ser Cys Lys Ala Ser Gly Tyr Thr Phe Thr Asp Tyr Trp Met His Trp
     50                  55                  60 gtt aaa cag agg cct gga cag ggt ctg gaa tgg att gga tac att aat    240
Val Lys Gln Arg Pro Gly Gln Gly Leu Glu Trp Ile Gly Tyr Ile Asn
 65                  70                  75                  80 cct aac act gct tat act gac tac aat cag aaa ttc aag gac aag gcc    288
Pro Asn Thr Ala Tyr Thr Asp Tyr Asn Gln Lys Phe Lys Asp Lys Ala
                 85                  90                  95 aca ttg act gca gac aaa tcc tcc agc aca gcc tac atg caa ctg cgc    336
Thr Leu Thr Ala Asp Lys Ser Ser Ser Thr Ala Tyr Met Gln Leu Arg
                100                 105                 110 agc ctg acc tct gag gat tct gca gtc tat tac tgt gca aaa aag aca    384
Ser Leu Thr Ser Glu Asp Ser Ala Val Tyr Tyr Cys Ala Lys Lys Thr
            115                 120                 125 act cag act acg tgg ggg ttt cct ttt tgg ggc caa ggg acc acg gtc    432
Thr Gln Thr Thr Trp Gly Phe Pro Phe Trp Gly Gln Gly Thr Thr Val
        130                 135                 140 acc gtc tcc tca ggt gga ggc ggt tca ggc gga ggt ggc tct ggc ggt    480
Thr Val Ser Ser Gly Gly Gly Gly Ser Gly Gly Gly Gly Ser Gly Gly
145                 150                 155                 160 ggc gga tcg gac att gtg ctg acc cag tct cca aaa tcc atg gcc atg    528
Gly Gly Ser Asp Ile Val Leu Thr Gln Ser Pro Lys Ser Met Ala Met
                165                 170                 175 tca gtc gga gag agg gtc acc ttg agc tgc aag gcc agt gag aat gtg    576
Ser Val Gly Glu Arg Val Thr Leu Ser Cys Lys Ala Ser Glu Asn Val
            180                 185                 190 gat tct ttt gtt tcc tgg tat caa cag aaa cca ggc cag tct cct aaa    624
Asp Ser Phe Val Ser Trp Tyr Gln Gln Lys Pro Gly Gln Ser Pro Lys
        195                 200                 205 ctg ctg ata tac ggg gcc tcc aac cgg tac act ggg gtc ccc gat cgc    672
Leu Leu Ile Tyr Gly Ala Ser Asn Arg Tyr Thr Gly Val Pro Asp Arg
    210                 215                 220 ttc gca ggc agt gga tct gga aga gat ttc act ctg acc atc agc agt    720
Phe Ala Gly Ser Gly Ser Gly Arg Asp Phe Thr Leu Thr Ile Ser Ser
225                 230                 235                 240
```

FIG. 7A

```
gtg cag gct gaa gac ctt gca gat tat cac tgt gga cag aat tac agg      768
Val Gln Ala Glu Asp Leu Ala Asp Tyr His Cys Gly Gln Asn Tyr Arg
            245                 250                 255 tat ccg ctc acg ttc ggt gct ggc acc aag ctg gaa atc aaa cgg gcg      816
Tyr Pro Leu Thr Phe Gly Ala Gly Thr Lys Leu Glu Ile Lys Arg Ala
            260                 265                 270 gcc gca ctc gag tct aga atg gtc cag gcc tcg atg agg agc cca aat      864
Ala Ala Leu Glu Ser Arg Met Val Gln Ala Ser Met Arg Ser Pro Asn
            275                 280                 285 atg gag acg ttc aaa cag cag aag gtg gag gac ttt tat gat att gga      912
Met Glu Thr Phe Lys Gln Gln Lys Val Glu Asp Phe Tyr Asp Ile Gly
            290                 295                 300 gag gag ctg ggc agt ggc cag ttt gcc atc gtg aag aag tgc cgg gag      960
Glu Glu Leu Gly Ser Gly Gln Phe Ala Ile Val Lys Lys Cys Arg Glu
305                 310                 315                 320 aag agc acg ggg ctg gag tat gca gcc aag ttc att aag aag agg cag     1008
Lys Ser Thr Gly Leu Glu Tyr Ala Ala Lys Phe Ile Lys Lys Arg Gln
            325                 330                 335 agc cgg gcc agc cgt cgg ggc gtg tgc cgg gag gaa atc gag cgg gag     1056
Ser Arg Ala Ser Arg Arg Gly Val Cys Arg Glu Glu Ile Glu Arg Glu
            340                 345                 350 gtg agc atc ctg cgg cag gtg ctg cac ccc aac atc atc acg ctg cac     1104
Val Ser Ile Leu Arg Gln Val Leu His Pro Asn Ile Ile Thr Leu His
            355                 360                 365 gac ctc tat gag aac cgc acc gac gtg gtg ctc atc ctt gag cta gtg     1152
Asp Leu Tyr Glu Asn Arg Thr Asp Val Val Leu Ile Leu Glu Leu Val
            370                 375                 380 tcc gga gga gaa ctg ttt gat ttc ctg gcc cag aag gag tcg tta agt     1200
Ser Gly Gly Glu Leu Phe Asp Phe Leu Ala Gln Lys Glu Ser Leu Ser
385                 390                 395                 400 gag gag gaa gcc acc agc ttc att aag cag atc ctg gat ggg gtg aat     1248
Glu Glu Glu Ala Thr Ser Phe Ile Lys Gln Ile Leu Asp Gly Val Asn
            405                 410                 415 tac ctt cac aca aag aaa att gct cac ttt gat ctc aag cca gaa aac     1296
Tyr Leu His Thr Lys Lys Ile Ala His Phe Asp Leu Lys Pro Glu Asn
            420                 425                 430 atc atg ttg tta gac aag aat atc cca att cca cac atc aag ctg att     1344
Ile Met Leu Leu Asp Lys Asn Ile Pro Ile Pro His Ile Lys Leu Ile
            435                 440                 445 gac ttt ggc ctg gct cac gaa ata gaa gat gga gtt gaa ttt aaa aac     1392
Asp Phe Gly Leu Ala His Glu Ile Glu Asp Gly Val Glu Phe Lys Asn
            450                 455                 460 att ttt ggg aca cct gaa ttt gtt gct cca gaa atc gtg aac tat gag     1440
Ile Phe Gly Thr Pro Glu Phe Val Ala Pro Glu Ile Val Asn Tyr Glu
465                 470                 475                 480
```

FIG. 7B

```
cca ctg gga ctg gag gcc gac atg tgg agc att gga gtc atc acc tat    1488
Pro Leu Gly Leu Glu Ala Asp Met Trp Ser Ile Gly Val Ile Thr Tyr
            485                 490                 495 atc ctt cta agt gga gcg tcc ccc ttc ctg gga gac aca aaa caa gaa    1536
Ile Leu Leu Ser Gly Ala Ser Pro Phe Leu Gly Asp Thr Lys Gln Glu
            500                 505                 510 acc ctg gca aat atc act gct gtg agt tac gac ttt gat gag gaa ttc    1584
Thr Leu Ala Asn Ile Thr Ala Val Ser Tyr Asp Phe Asp Glu Glu Phe
            515                 520                 525 ttc agc cag aca agc gag ctg gcc aag gac ttc att cgg aag ctt ctt    1632
Phe Ser Gln Thr Ser Glu Leu Ala Lys Asp Phe Ile Arg Lys Leu Leu
            530                 535                 540 gtg aaa gag acc cgg aaa cgg ctt acc atc caa gag gct ctc aga cat    1680
Val Lys Glu Thr Arg Lys Arg Leu Thr Ile Gln Glu Ala Leu Arg His
545                 550                 555                 560 ccc tgg atc gga tcc aaa cta gct gag cac gaa ttt cga gga ggg ccc    1728
Pro Trp Ile Gly Ser Lys Leu Ala Glu His Glu Phe Arg Gly Gly Pro
                565                 570                 575 gaa caa aaa ctc atc tca gaa gag gat ctg aat agc gcc gtc gac cat    1776
Glu Gln Lys Leu Ile Ser Glu Glu Asp Leu Asn Ser Ala Val Asp His
            580                 585                 590 cat cat cat cat cat tga                                            1794
His His His His His
            595
```

FIG. 7C

```
Met Glu Thr Asp Thr Leu Leu Leu Trp Val Leu Leu Leu Trp Val Pro
 1               5                  10                  15
Gly Ser Thr Gly Asp Ala Ala Gln Pro Ala Met Ala Gln Val Lys Leu
            20                  25                  30
Gln Glu Ser Gly Thr Glu Leu Ala Lys Pro Gly Ala Ala Val Lys Met
        35                  40                  45
Ser Cys Lys Ala Ser Gly Tyr Thr Phe Thr Asp Tyr Trp Met His Trp
    50                  55                  60
Val Lys Gln Arg Pro Gly Gln Gly Leu Glu Trp Ile Gly Tyr Ile Asn
 65              70                  75                      80
Pro Asn Thr Ala Tyr Thr Asp Tyr Asn Gln Lys Phe Lys Asp Lys Ala
                85                  90                  95
Thr Leu Thr Ala Asp Lys Ser Ser Ser Thr Ala Tyr Met Gln Leu Arg
            100                 105                 110
Ser Leu Thr Ser Glu Asp Ser Ala Val Tyr Tyr Cys Ala Lys Lys Thr
        115                 120                 125
Thr Gln Thr Thr Trp Gly Phe Pro Phe Trp Gly Gln Gly Thr Thr Val
    130                 135                 140
Thr Val Ser Ser Gly Gly Gly Ser Gly Gly Gly Gly Ser Gly Gly
145             150                 155                 160
Gly Gly Ser Asp Ile Val Leu Thr Gln Ser Pro Lys Ser Met Ala Met
            165                 170                 175
Ser Val Gly Glu Arg Val Thr Leu Ser Cys Lys Ala Ser Glu Asn Val
            180                 185                 190
Asp Ser Phe Val Ser Trp Tyr Gln Gln Lys Pro Gly Gln Ser Pro Lys
        195                 200                 205
Leu Leu Ile Tyr Gly Ala Ser Asn Arg Tyr Thr Gly Val Pro Asp Arg
    210                 215                 220
Phe Ala Gly Ser Gly Ser Gly Arg Asp Phe Thr Leu Thr Ile Ser Ser
225                 230                 235                 240
Val Gln Ala Glu Asp Leu Ala Asp Tyr His Cys Gly Gln Asn Tyr Arg
            245                 250                 255
Tyr Pro Leu Thr Phe Gly Ala Gly Thr Lys Leu Glu Ile Lys Arg Ala
            260                 265                 270
Ala Ala Leu Glu Ser Arg Met Val Gln Ala Ser Met Arg Ser Pro Asn
        275                 280                 285
Met Glu Thr Phe Lys Gln Gln Lys Val Glu Asp Phe Tyr Asp Ile Gly
    290                 295                 300
Glu Glu Leu Gly Ser Gly Gln Phe Ala Ile Val Lys Lys Cys Arg Glu
305                 310                 315                 320
Lys Ser Thr Gly Leu Glu Tyr Ala Ala Lys Phe Ile Lys Lys Arg Gln
            325                 330                 335
Ser Arg Ala Ser Arg Arg Gly Val Cys Arg Glu Glu Ile Glu Arg Glu
        340                 345                 350
Val Ser Ile Leu Arg Gln Val Leu His Pro Asn Ile Ile Thr Leu His
    355                 360                 365
Asp Leu Tyr Glu Asn Arg Thr Asp Val Val Leu Ile Leu Glu Leu Val
    370                 375                 380
Ser Gly Gly Glu Leu Phe Asp Phe Leu Ala Gln Lys Glu Ser Leu Ser
385                 390                 395                 400
Glu Glu Glu Ala Thr Ser Phe Ile Lys Gln Ile Leu Asp Gly Val Asn
            405                 410                 415
Tyr Leu His Thr Lys Lys Ile Ala His Phe Asp Leu Lys Pro Glu Asn
        420                 425                 430
Ile Met Leu Leu Asp Lys Asn Ile Pro Ile Pro His Ile Lys Leu Ile
    435                 440                 445
Asp Phe Gly Leu Ala His Glu Ile Glu Asp Gly Val Glu Phe Lys Asn
450                 455                 460
```

FIG. 8A

```
Ile Phe Gly Thr Pro Glu Phe Val Ala Pro Glu Ile Val Asn Tyr Glu
465                 470                 475                 480
Pro Leu Gly Leu Glu Ala Asp Met Trp Ser Ile Gly Val Ile Thr Tyr
                485                 490                 495
Ile Leu Leu Ser Gly Ala Ser Pro Phe Leu Gly Asp Thr Lys Gln Glu
                500                 505                 510
Thr Leu Ala Asn Ile Thr Ala Val Ser Tyr Asp Phe Asp Glu Glu Phe
            515                 520                 525
Phe Ser Gln Thr Ser Glu Leu Ala Lys Asp Phe Ile Arg Lys Leu Leu
        530                 535                 540
Val Lys Glu Thr Arg Lys Arg Leu Thr Ile Gln Glu Ala Leu Arg His
545                 550                 555                 560
Pro Trp Ile Gly Ser Lys Leu Ala Glu His Glu Phe Arg Gly Gly Pro
                565                 570                 575
Glu Gln Lys Leu Ile Ser Glu Glu Asp Leu Asn Ser Ala Val Asp His
                580                 585                 590
His His His His
        595
```

FIG. 8B

```
atg aaa tac ctg ctg ccg acc gct gct gct ggt ctg ctc ctc gct      48
Met Lys Tyr Leu Leu Pro Thr Ala Ala Ala Gly Leu Leu Leu Ala
 1           5                  10                  15 gcc cag ccg gcg atg gcc atg ggc cat cat cat cat cat cat cat      96
Ala Gln Pro Ala Met Ala Met Gly His His His His His His His
             20                  25                  30 cat cac agc agc ggc cat atc gac gac gac gac aag cat atg aag ctt  144
His His Ser Ser Gly His Ile Asp Asp Asp Asp Lys His Met Lys Leu
             35                  40                  45 atg gcc cag ccg gcc atg gcc cag gtc aag ctg cag gag tca ggg act  192
Met Ala Gln Pro Ala Met Ala Gln Val Lys Leu Gln Glu Ser Gly Thr
         50                  55                  60 gaa ctg gca aag cct ggg gcc gca gtg aag atg tcc tgc aag gct tct  240
Glu Leu Ala Lys Pro Gly Ala Ala Val Lys Met Ser Cys Lys Ala Ser
65                  70                  75                  80 ggc tac acc ttt act gac tac tgg atg cac tgg gtt aaa cag agg cct  288
Gly Tyr Thr Phe Thr Asp Tyr Trp Met His Trp Val Lys Gln Arg Pro
                 85                  90                  95 gga cag ggt ctg gaa tgg att gga tac att aat cct aac act gct tat  336
Gly Gln Gly Leu Glu Trp Ile Gly Tyr Ile Asn Pro Asn Thr Ala Tyr
             100                 105                 110 act gac tac aat cag aaa ttc aag gac aag gcc aca ttg act gca gac  384
Thr Asp Tyr Asn Gln Lys Phe Lys Asp Lys Ala Thr Leu Thr Ala Asp
            115                 120                 125 aaa tcc tcc agc aca gcc tac atg caa ctg cgc agc ctg acc tct gag  432
Lys Ser Ser Ser Thr Ala Tyr Met Gln Leu Arg Ser Leu Thr Ser Glu
        130                 135                 140 gat tct gca gtc tat tac tgt gca aaa aag aca act cag act acg tgg  480
Asp Ser Ala Val Tyr Tyr Cys Ala Lys Lys Thr Thr Gln Thr Thr Trp
145                 150                 155                 160 ggg ttt cct ttt tgg ggc caa ggg acc acg gtc acc gtc tcc tca ggt  528
Gly Phe Pro Phe Trp Gly Gln Gly Thr Thr Val Thr Val Ser Ser Gly
                165                 170                 175 gga ggc ggt tca ggc gga ggt ggc tct ggc ggt ggc gga tcg gac att  576
Gly Gly Gly Ser Gly Gly Gly Gly Ser Gly Gly Gly Gly Ser Asp Ile
            180                 185                 190 gtg ctg acc cag tct cca aaa tcc atg gcc atg tca gtc gga gag agg  624
Val Leu Thr Gln Ser Pro Lys Ser Met Ala Met Ser Val Gly Glu Arg
        195                 200                 205 gtc acc ttg agc tgc aag gcc agt gag aat gtg gat tct ttt gtt tcc  672
Val Thr Leu Ser Cys Lys Ala Ser Glu Asn Val Asp Ser Phe Val Ser
210                 215                 220 tgg tat caa cag aaa cca ggc cag tct cct aaa ctg ctg ata tac ggg  720
Trp Tyr Gln Gln Lys Pro Gly Gln Ser Pro Lys Leu Leu Ile Tyr Gly
225                 230                 235                 240
```

FIG. 9A

```
gcc tcc aac cgg tac act ggg gtc ccc gat cgc ttc gca ggc agt gga    768
Ala Ser Asn Arg Tyr Thr Gly Val Pro Asp Arg Phe Ala Gly Ser Gly
                245                 250                 255 tct gga aga gat ttc act ctg acc atc agc agt gtg cag gct gaa gac    816
Ser Gly Arg Asp Phe Thr Leu Thr Ile Ser Ser Val Gln Ala Glu Asp
                260                 265                 270 ctt gca gat tat cac tgt gga cag aat tac agg tat ccg ctc acg ttc    864
Leu Ala Asp Tyr His Cys Gly Gln Asn Tyr Arg Tyr Pro Leu Thr Phe
                275                 280                 285 ggt gct ggc acc aag ctg gaa atc aaa cgg gcg gcc gca gag ctc ggc    912
Gly Ala Gly Thr Lys Leu Glu Ile Lys Arg Ala Ala Ala Glu Leu Gly
                290                 295                 300 gga ggt ggc tct atg gca gac gaa gat ctc atc ttc cgc ctg gaa ggc    960
Gly Gly Gly Ser Met Ala Asp Glu Asp Leu Ile Phe Arg Leu Glu Gly
305                 310                 315                 320 gtt gat ggc ggc cag tcc ccc cga gct ggc cat gat ggt gat tct gat   1008
Val Asp Gly Gly Gln Ser Pro Arg Ala Gly His Asp Gly Asp Ser Asp
                    325                 330                 335 ggg gac agc gac gat gag gaa ggt tac ttc atc tgc ccc atc acg gat   1056
Gly Asp Ser Asp Asp Glu Glu Gly Tyr Phe Ile Cys Pro Ile Thr Asp
                340                 345                 350 gac cca agc tcg aac cag aat gtc aat tcc aag gtt aat aag tac tac   1104
Asp Pro Ser Ser Asn Gln Asn Val Asn Ser Lys Val Asn Lys Tyr Tyr
                355                 360                 365 agc aac cta aca aaa agt gag cgg tat agc tcc agc ggg tcc ccg gca   1152
Ser Asn Leu Thr Lys Ser Glu Arg Tyr Ser Ser Ser Gly Ser Pro Ala
            370                 375                 380 aac tcc ttc cac ttc aag gaa gcc tgg aag cac gca atc cag aag gcc   1200
Asn Ser Phe His Phe Lys Glu Ala Trp Lys His Ala Ile Gln Lys Ala
385                 390                 395                 400 aag cac atg ccc gac ccc tgg gct gag ttc cac ctg gaa gat att gcc   1248
Lys His Met Pro Asp Pro Trp Ala Glu Phe His Leu Glu Asp Ile Ala
                    405                 410                 415 acc gaa cgt gct act cga cac agg tac aac gcc gtc acc ggg gaa tgg   1296
Thr Glu Arg Ala Thr Arg His Arg Tyr Asn Ala Val Thr Gly Glu Trp
                420                 425                 430 ctg gat gat gaa gtt ctg atc aag atg gca tct cag ccc ttc ggc cga   1344
Leu Asp Asp Glu Val Leu Ile Lys Met Ala Ser Gln Pro Phe Gly Arg
                435                 440                 445 gga gca atg agg gag tgc ttc cgg acg aag aag ctc tcc aac ttc ttg   1392
Gly Ala Met Arg Glu Cys Phe Arg Thr Lys Lys Leu Ser Asn Phe Leu
        450                 455                 460 cat gcc cag cag tgg aag ggc gcc tcc aac tac gtg gcg aag cgc tac   1440
His Ala Gln Gln Trp Lys Gly Ala Ser Asn Tyr Val Ala Lys Arg Tyr
465                 470                 475                 480
```

FIG. 9B

```
atc gag ccc gta gac cgg gat gtg tac ttt gag gac gtg cgt cta cag    1488
Ile Glu Pro Val Asp Arg Asp Val Tyr Phe Glu Asp Val Arg Leu Gln
            485                 490                 495 atg gag gcc aag ctc tgg ggg gag gag tat aat cgg cac aag ccc ccc    1536
Met Glu Ala Lys Leu Trp Gly Glu Glu Tyr Asn Arg His Lys Pro Pro
        500                 505                 510 aag cag gtg gac atc atg cag atg tgc atc atc gag ctg aag gac aga    1584
Lys Gln Val Asp Ile Met Gln Met Cys Ile Ile Glu Leu Lys Asp Arg
            515                 520                 525 ccg ggc aag ccc ctc ttc cac ctg gag cac tac atc gag ggc aag tac    1632
Pro Gly Lys Pro Leu Phe His Leu Glu His Tyr Ile Glu Gly Lys Tyr
        530                 535                 540 atc aag tac aac tcc aac tct ggc ttt gtc cgc gat gac aac atc cgc    1680
Ile Lys Tyr Asn Ser Asn Ser Gly Phe Val Arg Asp Asp Asn Ile Arg
545                 550                 555                 560 ctg acg ccg cag gcc ttc agc cac ttc act ttt gag cgt tcc ggc cat    1728
Leu Thr Pro Gln Ala Phe Ser His Phe Thr Phe Glu Arg Ser Gly His
            565                 570                 575 cag ctg ata gtg gtg gac atc cag gga gtt ggg gat ctc tac act gac    1776
Gln Leu Ile Val Val Asp Ile Gln Gly Val Gly Asp Leu Tyr Thr Asp
        580                 585                 590 cca cag atc cac acg gag acg ggc act gac ttt gga gac ggc aac cta    1824
Pro Gln Ile His Thr Glu Thr Gly Thr Asp Phe Gly Asp Gly Asn Leu
            595                 600                 605 ggt gtc cgc ggg atg gcg ctc ttc ttc tac tct cat gcc tgc aac cgg    1872
Gly Val Arg Gly Met Ala Leu Phe Phe Tyr Ser His Ala Cys Asn Arg
        610                 615                 620 att tgc gag agc atg ggc ctt gct ccc ttt gac ctc tcg ccc cgg gag    1920
Ile Cys Glu Ser Met Gly Leu Ala Pro Phe Asp Leu Ser Pro Arg Glu
625                 630                 635                 640 agg gat gca gtg aat cag aac acc aag ctg ctg caa tca gcc aag acc    1968
Arg Asp Ala Val Asn Gln Asn Thr Lys Leu Leu Gln Ser Ala Lys Thr
            645                 650                 655 atc ttg aga gga aca gag gaa aaa tgt ggg agc ccc cga gta agg acc    2016
Ile Leu Arg Gly Thr Glu Glu Lys Cys Gly Ser Pro Arg Val Arg Thr
        660                 665                 670 ctc tct ggg agc cgg cca ccc ctc ctc cgt ccc ctt tca gag aac tct    2064
Leu Ser Gly Ser Arg Pro Pro Leu Leu Arg Pro Leu Ser Glu Asn Ser
        675                 680                 685 gga gac gag aac atg agc gac gtg acc ttc gac tct ctc cct tct tcc    2112
Gly Asp Glu Asn Met Ser Asp Val Thr Phe Asp Ser Leu Pro Ser Ser
        690                 695                 700 cca tct tcg gcc aca cca cac agc cag aag cta gac cac ctc cat tgg    2160
Pro Ser Ser Ala Thr Pro His Ser Gln Lys Leu Asp His Leu His Trp
705                 710                 715                 720
```

FIG. 9C

```
cca gtc ttc agt gac ctc gat aac atg gca tcc aga gac cat gat cat    2208
Pro Val Phe Ser Asp Leu Asp Asn Met Ala Ser Arg Asp His Asp His
            725                 730                 735 cta gac aac cac cgg gag tct gag aat agt ggg gac agc gga tac ccc    2256
Leu Asp Asn His Arg Glu Ser Glu Asn Ser Gly Asp Ser Gly Tyr Pro
            740                 745                 750 agt gag aag cgg ggt gag ctg gat gac cct gag ccc cga gaa cat ggc    2304
Ser Glu Lys Arg Gly Glu Leu Asp Asp Pro Glu Pro Arg Glu His Gly
            755                 760                 765 cac tca tac agt aat cgg aag tac gag tct gac gaa gac agc ctg ggc    2352
His Ser Tyr Ser Asn Arg Lys Tyr Glu Ser Asp Glu Asp Ser Leu Gly
            770                 775                 780 agc tct gga cgg gta tgt gta gag aag tgg aat ctc ctc aac tcc tcc    2400
Ser Ser Gly Arg Val Cys Val Glu Lys Trp Asn Leu Leu Asn Ser Ser
785                 790                 795                 800 cgc ctc cac ctg ccg agg gct tcg gcc gtg gcc ctg gaa gtg caa agg    2448
Arg Leu His Leu Pro Arg Ala Ser Ala Val Ala Leu Glu Val Gln Arg
            805                 810                 815 ctt aat gct ctg gac ctc gaa aag aaa atc ggg aag tcc att ttg ggg    2496
Leu Asn Ala Leu Asp Leu Glu Lys Lys Ile Gly Lys Ser Ile Leu Gly
            820                 825                 830 aag gtc cat ctg gcc atg gtg cgc tac cac gag ggt ggg cgc ttc tgc    2544
Lys Val His Leu Ala Met Val Arg Tyr His Glu Gly Gly Arg Phe Cys
            835                 840                 845 gag aag ggc gag gag tgg gac cag gag tcg gct gtc ttc cac ctg gag    2592
Glu Lys Gly Glu Glu Trp Asp Gln Glu Ser Ala Val Phe His Leu Glu
850                 855                 860 cac gca gcc aac ctg ggc gag ctg gag gcc atc gtg ggc ctg gga ctc    2640
His Ala Ala Asn Leu Gly Glu Leu Glu Ala Ile Val Gly Leu Gly Leu
865                 870                 875                 880 atg tac tcg cag ttg cct cat cac atc cta gcc gat gtc tct ctg aag    2688
Met Tyr Ser Gln Leu Pro His His Ile Leu Ala Asp Val Ser Leu Lys
            885                 890                 895 gag aca gaa gag aac aaa acc aaa gga ttt gat tac tta cta aag gcc    2736
Glu Thr Glu Glu Asn Lys Thr Lys Gly Phe Asp Tyr Leu Leu Lys Ala
            900                 905                 910 gct gaa gct ggc gac agg cag tcc atg atc cta gtg gcg cga gct ttt    2784
Ala Glu Ala Gly Asp Arg Gln Ser Met Ile Leu Val Ala Arg Ala Phe
            915                 920                 925 gac tct ggc cag aac ctc agc ccg gac agg tgc caa gac tgg cta gag    2832
Asp Ser Gly Gln Asn Leu Ser Pro Asp Arg Cys Gln Asp Trp Leu Glu
            930                 935                 940 gcc ctg cac tgg tac aac act gcc ctg gag atg acg gac tgt gat gag    2880
Ala Leu His Trp Tyr Asn Thr Ala Leu Glu Met Thr Asp Cys Asp Glu
945                 950                 955                 960
```

FIG. 9D

```
ggc ggt gag tac gac gga atg cag gac gag ccc cgg tac atg atg ctg    2928
Gly Gly Glu Tyr Asp Gly Met Gln Asp Glu Pro Arg Tyr Met Met Leu
            965             970             975 gcc agg gag gcc gag atg ctg ttc aca gga ggc tac ggg ctg gag aag    2976
Ala Arg Glu Ala Glu Met Leu Phe Thr Gly Gly Tyr Gly Leu Glu Lys
        980             985             990 gac ccg cag aga tca ggg gac ttg tat acc cag gca gca gag gca gcg    3024
Asp Pro Gln Arg Ser Gly Asp Leu Tyr Thr Gln Ala Ala Glu Ala Ala
            995             1000                1005 atg gaa gcc atg aag ggc cga ctg gcc aac cag tac tac caa aag gct    3072
Met Glu Ala Met Lys Gly Arg Leu Ala Asn Gln Tyr Tyr Gln Lys Ala
    1010                1015                1020 gaa gag gcc tgg gcc cag atg gag gag taa                            3102
Glu Glu Ala Trp Ala Gln Met Glu Glu
1025                1030
```

FIG. 9E

```
Met Lys Tyr Leu Leu Pro Thr Ala Ala Ala Gly Leu Leu Leu Leu Ala
 1           5                  10                  15
Ala Gln Pro Ala Met Ala Met Gly His His His His His His His His
            20              25                  30
His His Ser Ser Gly His Ile Asp Asp Asp Asp Lys His Met Lys Leu
        35                  40                  45
Met Ala Gln Pro Ala Met Ala Gln Val Lys Leu Gln Glu Ser Gly Thr
    50              55                  60
Glu Leu Ala Lys Pro Gly Ala Ala Val Lys Met Ser Cys Lys Ala Ser
65              70              75                          80
Gly Tyr Thr Phe Thr Asp Tyr Trp Met His Trp Val Lys Gln Arg Pro
                85                  90                  95
Gly Gln Gly Leu Glu Trp Ile Gly Tyr Ile Asn Pro Asn Thr Ala Tyr
            100                 105                 110
Thr Asp Tyr Asn Gln Lys Phe Lys Asp Lys Ala Thr Leu Thr Ala Asp
        115                 120                 125
Lys Ser Ser Ser Thr Ala Tyr Met Gln Leu Arg Ser Leu Thr Ser Glu
    130                 135                 140
Asp Ser Ala Val Tyr Tyr Cys Ala Lys Lys Thr Thr Gln Thr Thr Trp
145             150                 155                     160
Gly Phe Pro Phe Trp Gly Gln Gly Thr Thr Val Thr Val Ser Ser Gly
                165                 170                 175
Gly Gly Gly Ser Gly Gly Gly Gly Ser Gly Gly Gly Gly Ser Asp Ile
            180                 185                 190
Val Leu Thr Gln Ser Pro Lys Ser Met Ala Met Ser Val Gly Glu Arg
        195                 200                 205
Val Thr Leu Ser Cys Lys Ala Ser Glu Asn Val Asp Ser Phe Val Ser
    210                 215                 220
Trp Tyr Gln Gln Lys Pro Gly Gln Ser Pro Lys Leu Leu Ile Tyr Gly
225             230                 235                     240
Ala Ser Asn Arg Tyr Thr Gly Val Pro Asp Arg Phe Ala Gly Ser Gly
                245                 250                 255
Ser Gly Arg Asp Phe Thr Leu Thr Ile Ser Ser Val Gln Ala Glu Asp
            260                 265                 270
Leu Ala Asp Tyr His Cys Gly Gln Asn Tyr Arg Tyr Pro Leu Thr Phe
        275                 280                 285
Gly Ala Gly Thr Lys Leu Glu Ile Lys Arg Ala Ala Ala Glu Leu Gly
    290                 295                 300
Gly Gly Gly Ser Met Ala Asp Glu Asp Leu Ile Phe Arg Leu Glu Gly
305             310                 315                     320
Val Asp Gly Gly Gln Ser Pro Arg Ala Gly His Asp Gly Asp Ser Asp
                325                 330                 335
Gly Asp Ser Asp Asp Glu Glu Gly Tyr Phe Ile Cys Pro Ile Thr Asp
            340                 345                 350
Asp Pro Ser Ser Asn Gln Asn Val Asn Ser Lys Val Asn Lys Tyr Tyr
        355                 360                 365
Ser Asn Leu Thr Lys Ser Glu Arg Tyr Ser Ser Ser Gly Ser Pro Ala
    370                 375                 380
Asn Ser Phe His Phe Lys Glu Ala Trp Lys His Ala Ile Gln Lys Ala
385             390                 395                     400
Lys His Met Pro Asp Pro Trp Ala Glu Phe His Leu Glu Asp Ile Ala
                405                 410                 415
Thr Glu Arg Ala Thr Arg His Arg Tyr Asn Ala Val Thr Gly Glu Trp
            420                 425                 430
Leu Asp Asp Glu Val Leu Ile Lys Met Ala Ser Gln Pro Phe Gly Arg
        435                 440                 445
Gly Ala Met Arg Glu Cys Phe Arg Thr Lys Lys Leu Ser Asn Phe Leu
    450                 455                 460
His Ala Gln Gln Trp Lys Gly Ala Ser Asn Tyr Val Ala Lys Arg Tyr
465                 470                 475                 480
```

FIG. 10A

```
Ile Glu Pro Val Asp Arg Asp Val Tyr Phe Glu Asp Val Arg Leu Gln
            485                 490                 495
Met Glu Ala Lys Leu Trp Gly Glu Glu Tyr Asn Arg His Lys Pro Pro
            500                 505                 510
Lys Gln Val Asp Ile Met Gln Met Cys Ile Ile Glu Leu Lys Asp Arg
            515                 520                 525
Pro Gly Lys Pro Leu Phe His Leu Glu His Tyr Ile Glu Gly Lys Tyr
    530                 535                 540
Ile Lys Tyr Asn Ser Asn Ser Gly Phe Val Arg Asp Asp Asn Ile Arg
545                 550                 555                 560
Leu Thr Pro Gln Ala Phe Ser His Phe Thr Phe Glu Arg Ser Gly His
                565                 570                 575
Gln Leu Ile Val Val Asp Ile Gln Gly Val Gly Asp Leu Tyr Thr Asp
            580                 585                 590
Pro Gln Ile His Thr Glu Thr Gly Thr Asp Phe Gly Asp Gly Asn Leu
        595                 600                 605
Gly Val Arg Gly Met Ala Leu Phe Phe Tyr Ser His Ala Cys Asn Arg
    610                 615                 620
Ile Cys Glu Ser Met Gly Leu Ala Pro Phe Asp Leu Ser Pro Arg Glu
625                 630                 635                 640
Arg Asp Ala Val Asn Gln Asn Thr Lys Leu Leu Gln Ser Ala Lys Thr
                645                 650                 655
Ile Leu Arg Gly Thr Glu Glu Lys Cys Gly Ser Pro Arg Val Arg Thr
            660                 665                 670
Leu Ser Gly Ser Arg Pro Pro Leu Leu Arg Pro Leu Ser Glu Asn Ser
        675                 680                 685
Gly Asp Glu Asn Met Ser Asp Val Thr Phe Asp Ser Leu Pro Ser Ser
    690                 695                 700
Pro Ser Ser Ala Thr Pro His Ser Gln Lys Leu Asp His Leu His Trp
705                 710                 715                 720
Pro Val Phe Ser Asp Leu Asp Asn Met Ala Ser Arg Asp His Asp His
                725                 730                 735
Leu Asp Asn His Arg Glu Ser Glu Asn Ser Gly Asp Ser Gly Tyr Pro
            740                 745                 750
Ser Glu Lys Arg Gly Glu Leu Asp Asp Pro Glu Pro Arg Glu His Gly
        755                 760                 765
His Ser Tyr Ser Asn Arg Lys Tyr Glu Ser Asp Glu Asp Ser Leu Gly
    770                 775                 780
Ser Ser Gly Arg Val Cys Val Glu Lys Trp Asn Leu Leu Asn Ser Ser
785                 790                 795                 800
Arg Leu His Leu Pro Arg Ala Ser Ala Val Ala Leu Glu Val Gln Arg
                805                 810                 815
Leu Asn Ala Leu Asp Leu Glu Lys Lys Ile Gly Lys Ser Ile Leu Gly
            820                 825                 830
Lys Val His Leu Ala Met Val Arg Tyr His Glu Gly Gly Arg Phe Cys
        835                 840                 845
Glu Lys Gly Glu Glu Trp Asp Gln Glu Ser Ala Val Phe His Leu Glu
    850                 855                 860
His Ala Ala Asn Leu Gly Glu Leu Glu Ala Ile Val Gly Leu Gly Leu
865                 870                 875                 880
Met Tyr Ser Gln Leu Pro His His Ile Leu Ala Asp Val Ser Leu Lys
                885                 890                 895
Glu Thr Glu Glu Asn Lys Thr Lys Gly Phe Asp Tyr Leu Leu Lys Ala
            900                 905                 910
Ala Glu Ala Gly Asp Arg Gln Ser Met Ile Leu Val Ala Arg Ala Phe
        915                 920                 925
Asp Ser Gly Gln Asn Leu Ser Pro Asp Arg Cys Gln Asp Trp Leu Glu
    930                 935                 940
Ala Leu His Trp Tyr Asn Thr Ala Leu Glu Met Thr Asp Cys Asp Glu
945                 950                 955                 960
```

FIG. 10B

```
Gly Gly Glu Tyr Asp Gly Met Gln Asp Glu Pro Arg Tyr Met Met Leu
                965             970             975
Ala Arg Glu Ala Glu Met Leu Phe Thr Gly Gly Tyr Gly Leu Glu Lys
            980             985             990
Asp Pro Gln Arg Ser Gly Asp Leu Tyr Thr Gln Ala Ala Glu Ala Ala
        995             1000            1005
Met Glu Ala Met Lys Gly Arg Leu Ala Asn Gln Tyr Tyr Gln Lys Ala
    1010            1015            1020
Glu Glu Ala Trp Ala Gln Met Glu Glu
1025            1030
```

FIG. 10C

```
Gly Gly Gly Gly Ser Gly Gly Gly Gly Ser Gly Gly Gly Gly Ser
```

FIG. 11

```
Glu Gln Lys Leu Ile Ser Glu Glu Asp Leu
```

FIG. 12

```
Asp Xaa Trp Xaa Xaa Gly
```

IMMUNOKINASES

RELATED APPLICATION

This application claims priority to PCT application Ser. No. PCT/EP2005/050131 filed Jan. 13, 2005, which claims priority to European Application No. 04000847.6 filed Jan. 16, 2004 and European Application No. 04017928.5 filed Jul. 29, 2004, each of which are hereby incorporated herein by reference.

TECHNICAL FIELD OF THE INVENTION

The present invention relates to a synthetic, soluble, endogenous complex formed from at least one component A and at least one component B, whereby component A comprises a binding domain for extra-cellular surface structures that internalize upon binding of component A of said complex, and component B has a constitutive catalytic kinase activity and effects cell biosynthesis/signalling including cell death after internalization through phosphorylation. The present invention also relates to nucleic acids and/or vectors coding for such a complex. The present invention furthermore provides a method for influencing the cell growth and/or the physiology of cells to which said complex, nucleic acids or vectors have been targeted. The invention further relates to cells, or cell lines or non-human organisms, such as plants including algae and/or microorganisms, including yeast and fungi, producing the complex of the present invention. The present invention also concerns a kit comprising said complex, nucleic acids, vectors and/or cells. The present invention relates to the use of said complex, nucleic acids, vectors, cells or kit for the manufacturing of a medicament for the treatment of proliferative diseases, allergies, autoimmune diseases and/or chronic inflammation. The present invention further relates to the use of said complex, nucleic acids or vectors, cells and/or kit for targeted modulation of cellular signalling pathways, in order to effect the gene expression, and/or the viability of the target cell in a therapeutic manner. The invention further relates to a medicament comprising said complex, nucleic acids, vectors, cells or organisms. Furthermore the complexes, nucleic acids, vectors, cells and kits of the present invention are usable in prognostic, diagnostic and analytic kinase assays.

INTRODUCTION OF THE INVENTION

Medications currently available for proliferative diseases, such as chemotherapeutic agents, have the disadvantage of inducing considerable side effects due to their relative non-specificity. It has been attempted to moderate these by various therapeutic concepts. One potential approach is the use of immunotherapeutic agents to increase the specificity of medication. This approach has been especially useful for the treatment of tumors.

One type of an immunotherapeutic agent are immunotoxins. An immunotoxin comprises a monoclonal antibody (moAb) or a recombinant antibody fragment with a specific affinity for surface markers of target cells, which is coupled to a cytotoxic reagent. Cytotoxic agents are selected from toxins or radioactive elements. An immunotherapeutic wherein the cytotoxic agent is a radioactive elements is called radioimmunoconjugate. Immunotoxins and radioimmunoconjugate have been used for the treatment of malignancies.

Another type of immunotherapeutic agent are anti-immunoconjugates. An anti-immunoconjugate comprises a structure relevant to pathogenesis or a fragment thereof, which is coupled to a toxin component. Anti-immunoconjugates are used for the treatment of autoimmune diseases, tissue reactions or allergies.

When radioactively labeled anti-B-cell moAb were used with B-cell lymphomas, tumor regressions and even complete remissions could be observed (1). In contrast, the results with moAb against solid tumors were rather disillusioning. The relative large size of the ITs used in these studies seemed to interfere with their ability to penetrate the tumors, and made them ineffective therapeutics. The low tumor penetration rate posed a particular challenging problem for poorly vascularized tumors. In order to obtain better tissue and tumor penetration and in general improved diffusion properties, the ITs were miniaturized. It was also speculated, that these smaller ITs would be less immunogenic because of the reduced size of the antigenic determinants (2). Therefore proteolytically cleaved antibody fragments (miniaturized) were conjugated to the above mentioned effector functions (radioactive elements or toxins).

Improved cloning techniques allowed the preparation of completely recombinant ITs: Coding regions of immunoglobulin light and heavy chain variable regions, amplified by polymerase chain reaction, are joined together by a synthetic linker (e.g. $(Gly_4Ser)_3$) (SEQ ID NO: 7). The resulting single chain fragment of variable region genes (scFv) is then genetically fused to a coding region of a catalytically active enzyme including cytotoxically active proteins or polypeptides (3).

The peptidic cell poisons, which have been mostly used to date and thus best, characterized are the bacterial toxins diphtheria toxin (DT), *Pseudomonas* exotoxin A (PE), and the plant-derived Ricin-A (4). The mechanism of cytotoxic activity is essentially the same in all of these toxins despite of their different evolutionary backgrounds. The catalytic domain inhibits protein biosynthesis by direct modification of the elongation factor 2 (EF-2), which is important to translation, or by inactivation of the EF-2 binding site at the 28S-rRNA subunit of ribosomes.

In most of the constructs employed to date, the systemic application of immunotoxins results in more or less severe side effects. In addition to the "vascular leak" syndrome, thrombocytopenia, hemolysis, renal insufficiency and sickness also occur, depending on the construct employed and the applied dosage (4). Dose-dependent liver damage was also observed (5). In addition to the documented side effects, the immunogenicity of the constructs is one of the key problems of immunotherapy. This applies, in particular, to the humoral defense against the catalytic domains employed, such as Ricin (HARA), PE, or DT (2). Theoretically, all non-human structures can provoke an immune response. Thus, the repeated administration of immunotoxins and immunoconjugates is limited. A logical consequence of these problems is the development of human immunotoxins.

To date, human toxins used in immunotoxins have in most of all cases been selected from ribonucleases (6). Since human RNases are present in extracellular fluids, plasma and tissues, they are considered less immunogenic when used in immunotoxins. Angiogenin (ANG), a 14 kDa protein having a 64% sequence homology with RNase A, was first isolated from a tumor-cell-conditioned medium, where it was discovered due to its capability of inducing angiogenesis (7). It was shown that the t-RNA-specific RNase activity of Angiogenin has a cytotoxic potential. In accordance with that, chemically conjugated immunotoxins subsequently exhibited a cell-specific toxic activity. To evaluate the efficacy of ANG-based immunotoxins, different conformations of ANG with, e.g. epidermal growth factor (EGF) or CD30 ligand, were constructed and successfully tested in vitro (8). Another member of the RNase superfamily is eosinophilic neurotoxin (EDN). For EDN, which has a size of 18.4 kDa, only the direct neurotoxicity has been described to date. Based on the documented potency, different EDN-based immunotoxins have been constructed and successfully tested in vitro (9).

Very recently it was shown that proteases like granzyme B or derivatives thereof can efficiently fulfill the effector function of immunotoxins (WO-A-01/80880).

Protein phosphorylation is one of the most important mechanisms by which extracellular signals are transformed into biological responses in cells. Activation of protein kinases is the most common mode of signal transduction in biological systems. The three basic components of the phosphorylation systems are: 1) phosphoproteins that alter their properties by phosphorylation and dephosphorylation; 2) protein kinases that transfer a phosphate group from donor substrates, such as ATP and GTP, to serine, threonine, tyrosine or histidine residues; and 3) protein phosphatases that dephoshorylate phosphorylated proteins, thereby restoring the particular protein phosphorylation system to its basal stage. The eukaryotic protein kinases (ePK) represent the largest superfamily of homologous proteins that are involved in the regulation of intracellular signaling pathways. These kinases phosphorylate amino acid (aa) residues located in the loops or turns of their substrates. To regulate signal transduction pathways, there are approximately 2000 kinases and 500 protein phosphatases encoded within the human genome (10). A large number of these kinases are encoded by oncogenes and tumor-suppressor genes. The primary structures of hundreds of these enzymes are known, and all contain a conserved catalytic core of about 250-300 aa residues. The conserved structural features of the catalytic domain have been found from yeast, lower eukaryotes to mammals. The catalytic domain of a kinase domain is further divided into 12 smaller, subdomains, defined as regions uninterrupted by large insertions and containing characteristic, highly conserved aa residues. Subdomain I-IV, located at the amino-terminus of the catalytic domain, is involved in anchoring and orienting the nucleotide ATP. Subdomains VI-IX form a large lobe structure at the carboxy-terminus of the catalytic domain and are involved in the binding of substrates and catalyzing the phospho-transfer reaction. The pattern of aa residues found within subdomain VIB (HRD motif), VIII (A/SPE motif), and IX (DXWXXG motif (SEQ ID NO. 9) are highly conserved among different protein kinases.

The eukaryotic protein kinases make up a large superfamily of homologous proteins (11). A classification scheme is founded on a catalytic domain phylogeny, which reveals families of enzymes that have related substrate specificities and modes of regulation according to the scheme of Hanks and Hunter (12). Most protein kinases contain a conserved catalytic domain belonging to the eukaryotic protein kinase (ePK) superfamily (all other protein kinases are classified as atypical protein kinases (aPKs)). ePK's are classified into seven major groups, and are subdivided into families, and subfamilies, based on the sequence of their ePK domains:

Atypical protein kinases (aPK) lack sequence similarity to the ePK domains, but either have protein kinase activity, or a clear homology of aPKs with protein kinase activity. All aPK families are small, several having just one member in vertebrates. None have been found in invertebrates. A number of reports have shown that the kinases of this subfamily play critical roles in signaling pathways that control cell growth, differentiation and survival. Recently, several investigators have identified a number of aPKC-interacting proteins and their characterization is helping to unravel the mechanisms of action and functions of these kinases. Recently, a new family of aPKs called alpha kinases that does not have any homology to the serine/threonine/tyrosine protein kinase superfamily has been identified (13). The alpha kinases differ from serine/threonine/tyrosine protein kinases in that they phosphorylate a threonine aa residue located in the alpha helical region of the substrate.

Free calcium is a major second messenger in all cell types. One mechanism by which calcium ions exert their effects is by binding to a 17-kDa protein, calmodulin (CaM). The binding of four calcium ions to calmodulin changes its conformation and promotes its interaction with a number of other proteins, including several classes of protein kinases that are activated by the calcium/CaM complex (14). Classifying the calcium/CaM-dependent protein kinases is based on their substrate specificity. Some of these enzymes have only one substrate, and are designed as "dedicated" calcium/CaM-dependent protein kinases, while others have broad substrate specificity and are termed "multifunctional" kinases. The dedicated calcium/CaM-dependent protein kinases comprise three enzymes. Phosphorylase kinase, myosin light chain kinase and eukaryotic elongation factor-2 kinase. Multifunctional calcium/CaM-dependent protein kinases comprise four enzymes referred to as CaM-kinases I, II, IV and pro-apoptotic serine/threonine death protein kinases.

One of the positive mediators of apoptosis is DAP-kinase (DAPk) (15). DAPk is a pro-apoptotic calcium/CaM-regulated serine/threonine kinase with tumor-suppressive activity. DAPk is frequently inactivated by promoter methylation in human cancer. Its expression is frequently lost in human carcinoma and B- and (NK)/T-cell malignancies, in some cases in association with more aggressive stages of disease (16). Very recently, it has been shown, that no expression of DAPk was detectable in high-metastatic lung carcinoma cell lines, whereas the low-metastatic counterparts were positive for DAPk. Four additional kinases that have a significant homology in their catalytic domain to DAPk were recently identified. ZIP(Dlk)-kinase and DRP-1, also named DAPk2, are the closest family, members, as their catalytic domains share approximately 80% identity to that of DAPk. Two more distant DAPk-related proteins are DRAK1 and DRAK2. Both the pro-apoptotic and tumor-suppressive functions of DAPk depend on its kinase catalytic activity. The CaM-regulatory segment of DAPk possesses an autoinhibitory effect on the catalytic activity, and is relieved by binding to Ca2+-activated CaM. Consistently, the deletion of this segment from DAPk-ΔCaM mutant generated a constitutively active kinase ("super-killing kinase"), which displayed CaM-independent substrate phosphorylation in vitro and promoted apoptotic activity in vivo (17). Eukaryotic elongation factor-2 kinase (eEF-2k) belongs to the alpha kinases and is distinct from the main family of protein kinases with which they share no sequence similarity (18). The activity of eukaryotic elongation factor-2 (eEF-2) is crucial for the elongation step of mRNA translation. eEF-2 activity is regulated by phosphorylation. To be active, eEF-2 must be dephosphorylated, since phosphorylation at Thr-56 and 58 causes inactivation, resulting in the termination of mRNA translation. Phosphorylation of eEF-2 at Thr-56 and 58 by the highly specific calcium/CaM-dependent eEF-2k results in eEF-2 inactivation and, therefore, may regulate the global rate of protein synthesis at the elongation stage in animal cells. eEF-2k is itself regulated both negatively and positively by phosphorylation on at least five different serine residues, probably mediated by seven or more protein kinases. Very recently, it has been shown, that a point mutation at Ser-499, eEF2K S499D, transforms the kinase into a constitutively active form (19).

Protein phosphorylation is implicated in cellular processes such as proliferation, differentiation, secretion, invasion, angiogenesis, metastasis and apoptosis. Protein kinases and phosphatases play key roles in regulating these processes. Changes in the level, subcellular location and activity of kinases and phosphatases have consequences on normal cell function and maintenance of cellular homeostasis. Dysfunction in activities of protein kinases may lead to severe pathological states. In cancer, as well as in other proliferative diseases, deregulated cell proliferation, differentiation and survival frequently results from abnormal protein phosphorylation.

The identification of the key roles of protein kinases in proliferative diseases has led to extensive efforts to develop kinase inhibitors for treatment of a wide range of cancers. Many different tyrosine and serine/threonine protein kinases have been selected as candidates for drug discovery activities in oncology/inflammatory research, based either on their overexpression and/or on dysfunction in a particular organ or tissue, or through their association in deregulated signal transduction/cell cycle pathways. To date, more than 30 different tyrosine kinase targets are under evaluation in drug discovery projects in oncology. Chemical inhibitors (organic molecules, peptide inhibitors), antisense oligonucleotides and kinase-selective antibodies have been developed which target intracellular kinases.

Nevertheless, development was slow and associated with problems, mainly because of the associated toxicity, attributed to the poor selectivity of these compounds. Protein kinase inhibitors mainly bind at the active site of the enzyme, in competition with ATP+, and whether such inhibitors could ever be used for the long-term treatment of chronic conditions, such as rheumatoid arthritis, is still questionable.

Similarly the state of the art immunotoxins, such as chemically-linked or recombinant immunotoxins comprising ribonucleases, are still associated with the problem of unspecific toxicity. This problem reduces the efficiency of compositions comprising said immunotoxins, and limits their usefulness as therapeutic agents.

Very recently, different chimeric proteins of kinases fused to distinct ligands were developed: A) Ligand-kinase fusion proteins were constructed to influence T-cell behaviour after transfection (U.S. Pat. No. 5,670,324): after transformation of T-cells with a vector coding for a chimeric CD4-kinase fusion, the expressed chimeric membrane-bound molecules may be used to identify drugs that block T cell activation or low level self-antigens. B) Chimeric kinase-based receptors were also constructed to redirect immune effector cells. Human immune effector cells transformed with a vector encoding for a membrane-bound ligand-kinase fusion proteins may be able to specifically target cells via their extracellular ligand and may initiate killing of the target cells by activity of the fused kinase acticity triggering activation of the transformed immune effector cell (US 2002/0176851 A1). C) Cyclin dependent kinases (CDKs), in particular human Myt-1 kinase and derivatives thereof were fused to the constant region of immunoglobulin molecules, which may improve pharmokinetic properties and simplify expression and purification of Myt-1 (U.S. Pat. No. 5,935,835). D) Other kinase-based fusion proteins, in particular scFv-kinase fusion proteins were constructed for the indirect identification of protein-protein interactions inside living cells after their transformation with two different vectors (US 2002/0151684 A1).

None of these kinase fusions is available as a soluble protein that would allow their use as a human immunotoxin.

Surprisingly it was found that the above-mentioned problems can be solved by soluble, endogenous complexes comprising cell-specific antibody fragment(s) which is/are linked to constantly and catalytically active kinase(s) that develop cytotoxic/regulative activity upon internalization of the complex. Surprisingly, the complexes of the present invention are superior over state of the art immunotoxins in that they have a higher specificity combining specific binding to a target cell with specific constitutive catalytic activity inside the target cell, a reduced immunogenicity, an improved activity and are resistant to non-specific inactivation, and are thus are less prone to activity reduction.

SUMMARY OF THE INVENTION

The present invention concerns a synthetic complex formed from at least one component A and at least one component B, whereby component A comprises a binding domain for extra-cellular surface structures that internalize upon binding of component A of said complex, and component B has constitutively a catalytic kinase activity, said complex is soluble and effects cell death after internalization. The component A is selected from the group of actively binding structures consisting of antibodies or their derivatives or fragments thereof, and/or chemical molecules such as carbohydrates, lipids, nucleic acids, peptides, vitamins, etc., and/or small molecules with up to 100 atoms with receptor-binding activity such as ligands, in particular single ions, peptidic molecules, non-peptidic molecules, etc., and/or cell surface carbohydrate binding proteins and their ligands such as lectins, in particular calnexins, o-type lectins, l-type lectins, m-type lectins, p-type lectins, r-type lectins, galectins and their derivatives, and/or receptor binding molecules such as natural ligands to the cluster of differentiation (CD) antigens, like CD30, CD40, etc., cytokines such as chemokines, colony stimulating factors, type-1 cytokines, type-2 cytokines, interferons, interleukins, lymphokines, monokines, etc., and/or adhesion molecules including their derivatives and mutants, and/or derivatives or combinations of any of the above listed of actively binding structures, which bind to CD antigens, cytokine receptors, hormone receptors, growth factor receptors, ion pumps, channel-forming proteins. The component A may also be selected from the group of passively binding structures consisting of allergens, peptidic allergens, recombinant allergens, allergen-idiotypical antibodies, autoimmune-provoking structures, tissue-rejection-inducing structures, immunoglobulin constant regions and their derivatives, mutants or combinations thereof. The complex of the present invention is directed by its component A to a target cell comprising a binding partner for the above listed binding structures of A. In a further embodiment the component A of the complex has a higher valency by comprising two or more identical and/or different binding structures. The complex of the present invention also comprises a component B which is at least one kinase selected from the following three classes of kinases: 1. eukaryotic protein kinase (ePK) superfamily, 2. histidine protein kinase (HPK) superfamily or 3. atypical protein kinase (aPK) superfamily. In a further embodiment the component B is a human kinase or a non-human kinase. A further embodiment of the invention is a complex wherein the ePK is selected from the group of calcium/calmodulin-regulated (CaM) death-promoting kinases, consisting of death-associated protein kinase (DAP-kinase, DAPk), DAP kinase-related protein kinase 1 (DRP-1), also named DAP-kinase 2 (DAPk2), DAP like kinase/Zipper interacting protein kinase (Dlk/ZIP-kinase), also named DAP-kinase 3 (DAPK3) and DAP kinase related apoptosis-inducing kinase (DRAK1 and DRAK2) families, the group of Group of calcium/calmodulin-regulated (CaM) death-promoting kinases-like (CAMKL) family, consisting of at least 49 subfamilies, protein kinase AMP-activated alpha 1 catalytic subunit (PRKAA1), protein kinase AMP-activated alpha 2 catalytic subunit (PRKAA2), BRSK1 and BRSK2, CHK1 checkpoint homologue (CHEK1), hormonally upregulated Neu-associated kinase (HUNK), serine/threonine kinase 11 (Peutz-Jeghers syndrome) (STK11), MAP/microtubule affinity-regulating kinase (MARK) 1-4, MARKps 01-30, likely ortholog of maternal embryonic leucine zipper kinase (KIAA0175), PAS domain containing serine/threonine kinase (PASK), NIM1, QIK and SNRK, the group of death-domain receptor interacting protein kinase (RIP-kinase) family, consisting of at least six subfamilies, RIP-kinase 1, RIP-kinase 2, RIP-kinase 3 and RIP-kinase 4, ankyrin repeat domain 3 (ANKRD3) and SqK288, the group of multifunctional CaM kinase family, consisting of CaM kinases I, II, including the microtubule affinity-regulating kinases (MARK) and microtubule affinity-regulating kinases-like 1 (MARKL1), CaM kinase IV and CaM kinase kinase subfamilies, the group of dedicated CaM kinases, consisting of Myosin light chain kinase (MLCk), phosphorylase kinase and CaM kinase III (eEF-2k), the group of mitogen-activated protein kinase (MAPK) family, consisting of extracellular signal-regulated kinases (ERK), o-JUN NH2-terminal protein kinases (JNK), nemo-like kinase (NLK) and p38 kinase subfamilies, the group of cyclin-dependent kinase (CDK) family, consisting of the subfamilies, cell cycle related kinase (CCRK), cell division cycle 2 (CDC2), cyclin-dependent kinases (CDK) 1-11, PCTAIRE protein kinase (PCTK) 1-3, PFTAIRE protein kinase (PFTK) 1-2 and cell division cycle 2-like 1 (PITSLRE proteins), the group of eukaryotic translation initiation factor 2-alpha kinase 3 (EIF2AK3) family, also named (PEK), consisting of the protein kinase interferon-inducible double stranded RNA (dsRNA) dependent (PKR) subfamily. A further embodiment of the present invention concerns a complex wherein the histidine protein kinase is selected from one of the eleven families HPK 1-11. A further embodiment of the present invention is a complex wherein the aPK is selected from the alpha protein kinase family, consisting of eukaryotic elongation factor-2 kinase (eEF-2k), myosin heavy chain kinase (MHC-kinase), eukaryotic translation initiation factor 2 alpha kinase 1 (E2K1) and channel kinase (Chak1 and Chak2) subfamilies, the group of Fas-activated s/t kinase (FASTK) family, consisting of the FASTK subfamily, the group of protein tyrosine kinase 9 (A6) family, consisting of A6 and protein tyrosine kinase 9-like (A6r) subfamilies, the group of p21-activated protein kinases (PAK) family, consisting of the three highly conserved isoforms: alpha-PAK (PAK1), beta-PAK (PAK3) and gamma-PAK (PAK2, PAKI), the group of Interleukin-1 (IL-1)-receptor-associated kinase (IRAK) family, consisting of IRAK-1, IRAK-2, IRAK-3 and IRAK-4 subfamilies, or derivatives, mutants or combinations thereof. These kinases were selected because they maintain their activity in a soluble complex. A further embodiment is a complex wherein the kinase activity of component B directly activates or inactivates components of cell-regulatory pathways through phosphorylation, acetylation, methylation, prenylation, and sulfation, altering the function, gene expression, or viability of a target cell, whereby a target cell is defined by the ability of component A to bind to the cell. Preferably the component B activates or inactivates components of cell-regulatory pathways through phosphorylation. In a further embodiment, component B of the complex is DAPK2 or a derivative thereof or EF-2K or a derivative thereof. Those two kinases were found to be particular effective in a complex according to the present invention. A further advantage of the DAPK2 is the existence of a constitutive active mutant of said enzyme which is particular suitable for the complex of the present invention. DAPKs are frequently found to be inactivated in human tumor cells. The complex of the present invention comprising such a DAPK is therefore particular useful since it enables the reintroduction of an active DAPK into, for example, a tumor. A complex comprising eEF-2k as component B has the advantage that it will be active in any human cell, since eEF-2k is ubiquitous. A derivative of those kinases is defined as a constitutively active kinase which has accumulated at least one mutation and/or modification, i.e. a deletion, a substitution, a domain swapping, etc. Preferred mutations are conservative amino acid changes, and preferred modifications are phosphorylations, acetylations, methylations etc. A further embodiment of the present invention is a complex comprising one or more supplementary components S which regulate protein biosynthesis on the transcription and/or translation level, and/or enable purification and/or detection of the complex or its components, and/or facilitate translocation of at least component B into the target cell and intracellular separation therein, and/or activation of component B. A further embodiment of the present invention is a complex wherein the components are chemically coupled and/or genetically fused to each other. A further embodiment are the genetically fused complexes named L-DAPk2-Ki-4-III/G (SEQ ID NO: 2), Ki-4-DAPk2-II/G (SEQ ID NO: 4) and Ki-4(scFv)-eEF-2K (SEQ ID NO: 6), encoded by the corresponding DNA molecules with SEQ ID NOs 1, 3, and 5, respectively. A further embodiment of the present invention are a nucleic acid molecule coding for said complex or for individual components thereof for the preparation of such complex, and/or a vector comprising said nucleic acid molecule. The present invention also concerns cells and non-human organisms synthesizing complete complexes or individual components thereof after having been transformed or transfected with nucleic acid molecules coding for said complexes of the present invention, or in vitro translation systems synthesizing complete complexes or individual components thereof. A further embodiment are also an organism and/or a cell transformed or transfected with the nucleic acid molecule or vector encoding said complex or components thereof, whereby said organism is either a prokaryote, such as *E. coli, B. subtilis, S. carnosus, S. coelicolor*, and/or *Marinococcus* sp., or a lower eukaryote, such as *Saccharomyces* sp., *Aspergillus* sp., *Spodoptera* sp. and/or *P. pastoris*, or a higher non-human eukaryote such as a plant and/or an animal, and the cell is a primary or cultivated mammalian cell, such as a freshly isolated human cell or a eukaryotic cell line, such as CHO, Cos or 293. A further embodiment is a method for influencing the growth and/or the physiology of the cells transfected or transformed with the nucleic acid molecule or the vector encoding said complex, by culturing the cells under conditions supporting the activity of the complex. A further embodiment of the present invention is a kit comprising the complex and/or the nucleic acid molecule and/or the vector, and/or the cells and/or prokaryotes and/or lower eukaryotes transfected or transformed with said nucleic acid molecules of the present invention. A further embodiment is the use of the complex, and/or the nucleic acid molecules, and/or vectors, and/or the cells and/or prokaryotes and/or lower eukaryotes transfected or transformed with said nucleic acid molecules and/or the kit for the preparation of a medicament for the treatment of proliferative diseases, such as cancerous or non-cancerous proliferative diseases, allergies, autoimmune diseases and/or chronic inflammation.

A further embodiment is a medicament comprising a complex, and/or nucleic acid molecules and/or vectors and/or or cells or organisms synthesising the complex of present invention, for treating proliferative diseases, such as cancerous or non-cancerous proliferative diseases, allergies, autoimmune reactions, chronic inflammation reactions or tissue rejection reactions. A further embodiment is the ex vivo, in vivo or in vitro use of the complex, and/or the nucleic acid molecule and/or the vector, and/or the cells and/or the organisms synthesising the complex and/or the kit, for the targeted modulation of cellular signaling pathways. A further embodiment is the use of the complex, and/or the nucleic acid molecule and/or the vector, and/or the cells and/or organisms synthesising the complex and/or the kit for prognostic, diagnostic, and/or analytic kinase assays, and/or for the development of such assays. A further embodiment is a method of treatment of proliferative diseases, such as cancerous or non-cancerous proliferative diseases, allergies, autoimmune diseases, and/or chronic inflammation comprising the steps of administering to a patient the complex of the present invention and/or the nucleic acid and/or the vector encoding said complex.

BRIEF DESCRIPTION OF THE DRAWINGS

FIG. 5A: Nucleic Acid sequence of the construct pMS-(L-DAPK2'-Ki-4)-III/G open reading frame (ORF).

FIG. 5B: Is the drawing of FIG. 5A continued onto a second page.

FIG. 5C: Is the drawing of FIG. 5A continued onto a third page.

FIG. 6A: Amino acid sequence of the construct pMS-(L-DAPK2'-Ki-4)-III/G open reading frame (ORF).

FIG. 6B: Is the drawing of FIG. 6A continued onto a second page.

FIG. 7A: Nucleic acid sequence of the construct pMS-(L-DAPK2'-Ki-4)-II/G ORF.

FIG. 7B: Is the drawing of FIG. 7A continued onto a second page.

FIG. 7C: Is the drawing of FIG. 7A continued onto a third page.

FIG. 8A: Amino acid sequence of the construct pMS-(L-DAPK2'-Ki-4)-II/G ORF.

FIG. 8B: Is the drawing of FIG. 8A continued onto a second page.

FIG. 9A: Nucleic acid sequence of the construct pMT-Ki4 (scFv)-eEF-2K ORF.

FIG. 9B: Is the drawing of FIG. 9A continued onto a second page.

FIG. 9C: Is the drawing of FIG. 9A continued onto a third page.

FIG. 9D: Is the drawing of FIG. 9A continued onto a fourth page.

FIG. 9E: Is the drawing of FIG. 9A continued onto a fifth page.

FIG. 10A: Amino acid sequence of the construct pMT-Ki4 (scFv)-eEF-2K ORF.

FIG. 10B: Is the drawing of FIG. 10A continued onto a second page.

FIG. 10C: Is the drawing of FIG. 10A continued onto a third page.

FIG. 11: Amino acid sequence of the synthetic linker.

FIG. 12: Amino acid sequence of the c-Myc epitope.

FIG. 13: Motif in the domain IX of kinases.

DETAILED DESCRIPTION OF THE INVENTION

Figure 1:
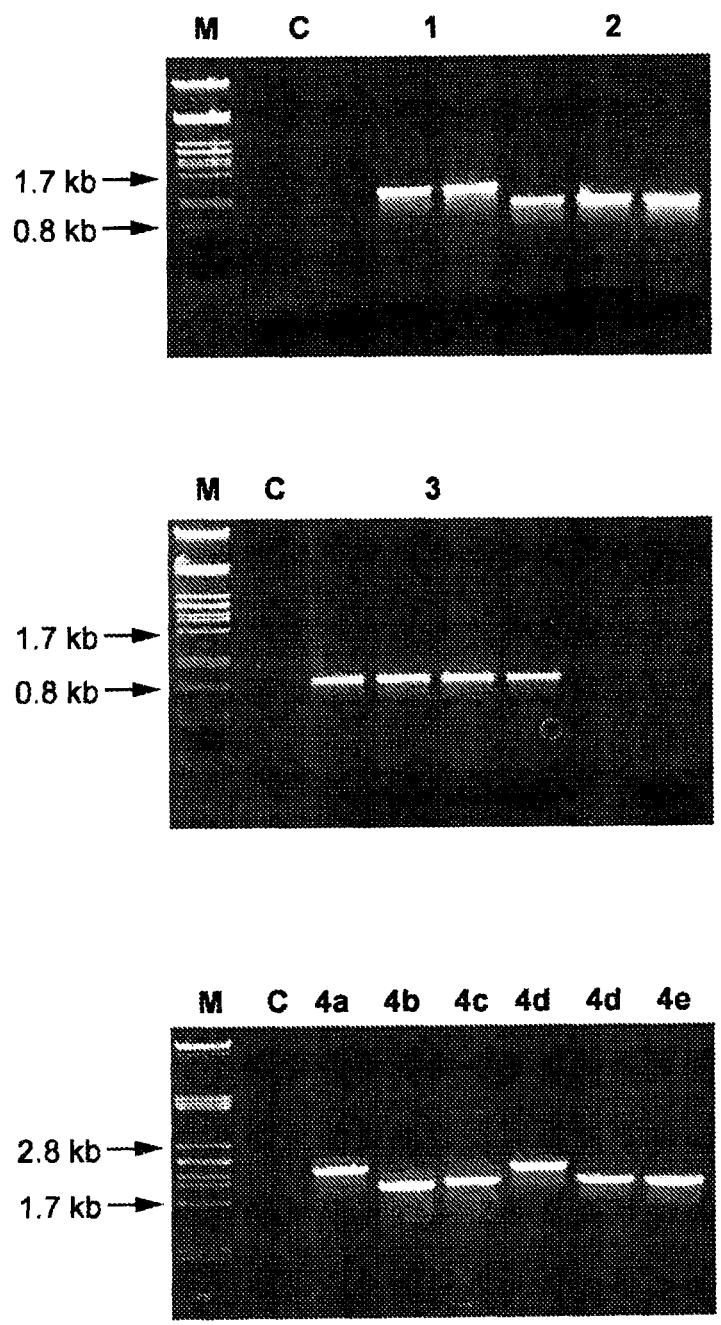
FIG. 1: Cloning of pMS-(L-DAPk2-Ki-4)-III/G (SEQ ID NO 1), pMS-(Ki-4-DAPk2)-II/G (SEQ ID NO 3) and pMT-Ki-4(scFv)-eEF-2K (SEQ ID NO 5). Lane 1-3, PCR-amplification of DAPk2 and derivatives thereof. Lane 4, PCR-amplification of eEF-2K and derivatives thereof. (M, DNA-ladder; C, negative control).

The complex according to the invention is a recombinant heterologous complex comprising at least two domains, i.e. one effector domain and at least one cell-specific binding domain. The complex according to the invention is usable for diagnosis and therapy of diseases.

The invention described herein draws on previously published work and pending patent applications. By way of example, such work consists of scientific papers, patents or pending patent applications. All of these publications and applications, cited previously or below are hereby incorporated by reference.

Definitions

As used herein, the term "immunotoxin" refers to chimeric molecules in which a cell-binding monoclonal antibody or fragments thereof are chemically coupled or genetically fused to toxins or their subunits. The toxin portion of the immunotoxin can be derived form various sources, such as plants, animals, higher and lower microorganisms such as bacteria and fungi, and In particular if the toxin is a catalytic enzyme, the enzyme can be of human origin. The toxin can also be a synthetic drug. Immunotoxins as well their constructions are reviewed above and are well known to the person skilled in the art.

As used herein, the term "immunokinase" refers to chimeric molecules in which a cell-binding monoclonal antibody or fragments thereof are coupled or fused to kinases or their subunits harboring the kinase activity. The term immunokinase is a synonym for the complex of the present invention.

As used herein, the term "component A" of the complex represents the actively binding structure of the complex of present invention. The component A is selected from the group of actively binding structures consisting of antibodies or their derivatives or fragments thereof, synthetic peptides such as scFv, mimotopes, etc. or chemical molecules such as carbohydrates, lipids, nucleic acids, peptides, vitamins, etc., and/or small molecules with up to 100 atoms with receptor-binding activity like ligands, in particular single atoms, peptidic molecules, non-peptidic molecules, etc., and/or cell surface carbohydrate binding proteins and their ligands such as lectins, in particular calnexins, o-type lectins, l-type lectins, m-type lectins, p-type lectins, r-type lectins, galectins and their derivatives, and/or receptor binding molecules such as natural ligands to the cluster of differentiation (CD) antigens, like CD30, CD40, etc., cytokines such as chemokines, colony stimulating factors, type-1 cytokines, type-2 cytokines, interferons, interleukins, lymphokines, monokines, etc., and/or adhesion molecules including their derivatives and mutants, and/or derivatives or combinations of any of the above listed of actively binding structures, which bind to CD antigens, cytokine receptors, hormone receptors, growth factor receptors, ion pumps, channel-forming proteins. The component A may also be selected from the group of passively binding structures consisting of allergens, peptidic allergens, recombinant allergens, allergen-idiotypical antibodies, autoimmune-provoking structures, tissue-rejection-inducing structures, immunoglobulin constant regions and their derivatives, mutants or combinations thereof. A component A with higher valency may be generated by combining at least two identical or different binding structures selected from the above mentioned groups.

As used herein, the term "antibody" refers to polyclonal antibodies, monoclonal antibodies, humanized antibodies, single-chain antibodies, and fragments thereof such as Fab, F(ab')2, Fv, and other fragments which retain the antigen binding function and specificity of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others which retain the antigen, binding function and specificity of the antibody. Monoclonal antibodies of any mammalian species can be used in this invention. In practice, however, the antibodies will typically be of rat, or murine origin because of the availability of rat or murine cell lines for use In making the required hybrid cell lines or hybridomas to produce monoclonal antibodies.

As used herein, the term "human antibodies" means that the framework regions of an immunoglobulin are derived from human immunoglobulin sequences.

As used herein, the term "single chain antibody fragments" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described In U.S. Pat. No. 4,946,778 to Ladner et al.

The "component B" of present invention represents the "targeted kinase" moiety of the immunokinase of the present invention and may be selected from any kinase known in the art. Presently, over 5,000 kinase-like sequences from diverse species are available for analysis in public databases. The human genome appears to encode 510 protein kinases in addition to many pseudo-protein kinase genes, and these have been subclassified into over 57 families. There may well be additional protein kinases that remain to be identified see world wide web at kinexus.ca/kinases.htm). However, preferably component B is chosen from the following three classes of kinases, which are all known to be active in humans and to retain their kinase activity in a soluble complex. 1. The eukaryotic protein kinase (ePK) superfamily, 2. the histidine protein kinase (HPK) superfamily, or 3. the atypical protein kinase (aPK) superfamily. If component B is chosen from the ePK superfamily, it is selected from the group of calcium/calmodulin-regulated (CaM) death-promoting kinases, consisting of death-associated protein kinase (DAP-kinase, DAPk), DAP kinase-related protein kinase 1 (DRP-1), also named DAP-kinase 2 (DAPk2), DAP like kinase/Zipper interacting protein kinase (Dlk/ZIP-kinase), also named DAP-kinase 3 (DAPK3) and DAP kinase related apoptosis-inducing kinase (DRAK1 and DRAK2) families, the group of calcium/calmodulin-regulated (CaM) death-promoting kinases-like (CAMKL) family, consisting of at least 49 subfamilies, protein kinase AMP-activated alpha 1 catalytic subunit (PRKAA1), protein kinase AMP-activated alpha 2 catalytic subunit (PRKAA2), BRSK1 and BRSK2, CHK1 checkpoint homologue (CHEK1), hormonally upregulated Neu-associated kinase (HUNK), serine/threonine kinase 11 (Peutz-Jeghers syndrome) (STK11), MAP/microtubule affinity-regulating kinase (MARK) 1-4, MARKps 01-30, likely ortholog of maternal embryonic leucine zipper kinase (KIAA0175), PAS domain containing serine/threonine kinase (PASK), NIM1, QIK and SNRK, the group of death-domain receptor interacting protein kinase (RIP-kinase) family, consisting of at least six subfamilies, RIP-kinase 1, RIP-kinase 2, RIP-kinase 3 and RIP-kinase 4, ankyrin repeat domain 3 (ANKRD3) and SqK288, the group of multifunctional CaM kinase family, consisting of CaM kinases. I, II, including the microtubule affinity-regulating kinases (MARK) and microtubule affinity-regulating kinases-like 1 (MARKL1), CaM kinase IV and CaM kinase kinase subfamilies, the group of dedicated CaM kinases, consisting of Myosin light chain kinase (MLCk), phosphorylase kinase and CaM kinase III (eEF-2k), the group of mitogen-activated protein kinase (MAPK) family, consisting of extracellular signal-regulated kinases (ERK), c-JUN NH2-terminal protein kinases (JNK), neuro-like kinase (NLK) and p38 kinase subfamilies, the group of cyclin-dependent kinase (CDK) family, consisting of the subfamilies, cell cycle related kinase (CCRK), cell division cycle 2 (CDC2), cyclin-dependent kinases (CDK) 1-11, PCTAIRE protein kinase (PCTK) 1-3, PFTAIRE protein kinase (PFTK) 1-2 and cell division cycle 2-like 1 (PITSLRE proteins), the group of eukaryotic translation initiation factor 2-alpha kinase 3 (EIF2AK3) family, also named (PEK), consisting of the protein kinase interferon-inducible double stranded RNA (dsRNA) dependent (PKR) subfamily.

If component B is chosen from the HPK superfamily, it is selected from the group of at least eleven families HPK 1-11.

If component B is chosen from the aPK superfamily, it is selected from the group of alpha protein kinase family, consisting of eukaryotic elongation factor-2 kinase (eEF-2k), myosin heavy chain kinase (MHC-kinase), eukaryotic translation initiation factor 2 alpha kinase 1 (E2K1) and channel kinase (Chak1 and Chak2) subfamilies, the group of Fas-activated s/t kinase (FASTK) family, consisting of the FASTK subfamily, the group of protein tyrosine kinase 9 (A6) family, consisting of A6 and protein tyrosine kinase 9-like (A6r) subfamilies, the group of p21-activated protein kinases (PAK) family, consisting of the three highly conserved isoforms: alpha-PAK (PAK1), beta-PAK (PAK3) and gamma-PAK (PAK2, PAKI), the group of Interleukin-1 (IL-1)-receptor-associated kinase (IRAK) family, consisting of IRAK-1, IRAK-2, IRAK-3 and IRAK-4 subfamilies.

The term "target cell" and or "target tissue" refers to cells or tissues carrying an extracellular surface structure to which the component A of the complex actively or passively binds. Target cells and target tissues are thus cells and tissues to which the component A of the complex can bind. The target cells and target tissues are further characterized by their ability to internalize the complex according to the present invention upon binding of component A. The term "soluble" refers to the ability of the complex to stay in solution when recombinantly expressed, in particular during protein purification, enabling high yields. The term "soluble" also refers to the state of the complex in fluidic systems inside an organism, until specifically attached to the target cell/tissue. The term also refers to the state of the complex inside a cell upon release from any kind of incorporation vesicles.

The term "endogenous" refers to the localization of the complex in the surrounding/environment of a given target cell/tissue.

The term synthetic refers to a man-made complex, not found in nature. The term also comprises the meaning of "recombinant".

The term "recombinant" refers to the preparation of molecules, in particular the covalent joining of molecules from different sources, by any one of the known methods of molecular biology. As used in the present invention, the term "recombinant" refers in particular to the fusion of the antibody part to the toxin part by any one of the known methods of molecular biology, such as through production of single chain antibodies. The recombinant DNA molecule encoding the recombinant fusion protein comprising the antibody part and the toxin part are recombinantly expressed. Recombinant immunotoxin produced in this way may be isolated by any technique known in the field of recombinant DNA expression technology suitable for this purpose.

The term "derivative" refers to a mutated or modified protein which has retained its characterizing activity, i.e. binding activity or kinase activity. Particular preferred are constitutively active derivatives. The term derivative comprises proteins which carry at least one amino acid substitution, deletion, addition, a swapping of a single domain or at least one modification of at least one amino acid. Preferred are derivatives which carry 20 such changes, more preferred are those with 10 such changes and most preferred are those with 1 to 5 such changes. Modifications, which can occur, are phosphorylation, acetylation, methylation, prenylation and sulfation.

As used herein, the term "vector" comprises DNA and RNA forms of a plasmid, a cosmid, a phage, phagemid, derivatives of them, or a virus. A vector comprises control sequences and coding sequences.

The term "expression of the recombinant genes encoding the recombinant complex", wherein the recombinant complex is a single chain antibody-toxin moiety fusion polypeptide, also called recombinant immunokinase, refers to the transformation and/or transfection of a host cell with a nucleic acid or vector encoding such a complex, and culturing said host cells selected from the group of bacteria, such as *E. coli*, and/or in yeast, such as in *S. cerevisiae*, and/or In established mammalian or insect cell lines, such as CHO, COS, BHK, 293T and MDCK cells, and/or in primary cells, such as human cells, non-human vertebrate cells, and/or in invertebrate cells such as insect cells, and the synthesis and translation of the corresponding mRNA, finally giving rise to the recombinant protein, the recombinant complex. In more detail, the term "expression of the recombinant genes encoding the recombinant complex", comprises the following steps:

Transformation of an appropriate cellular host with a recombinant vector, in which a nucleotide sequence coding for the fusion protein had been inserted under the control of the appropriate regulatory elements, particularly a promoter recognized by the polymerases of the cellular host. In the case of a prokaryotic host, an appropriate ribosome binding site (RBS) also precedes the nucleotide sequence coding for the fusion protein, enabling the translation in said cellular host. In the case of an eukaryotic host any artificial signal sequence or pre/pro sequence may be provided, or the natural signal sequence may be employed. The transformed cellular host is cultured under conditions enabling the expression of said insert.

As used herein, the expression "killing of antigen-expressing cells" refers to the inhibition of protein synthesis or induction of apoptosis, resulting in elimination or death of these cells.

The term "supplementary components S", refers to an additional component of the complex comprising A and B. The supplementary component S contributes features and properties to the complex which allow efficient preparation and/or modify the effectiveness of the complex:

the inducible regulation of transcription/translation (e.g., inducible promoters);
control of protein biosynthesis (e.g., leader sequences);
purification/detection of the complex or its components (e.g., His tag, affinity tags);
translocation of the apoptotic agents into the target cells (e.g., translocation domain, amphiphatic sequences);
intracellular activation/separation of component B (synthetic pro-granzyme B, amphiphatic sequences).

Thus the component S is selected from the group of inducible promoters, leader sequences, affinity tags, His tags, translocation domain, amphiphatic sequences and synthetic pro-granzyme B. The invention also relates to nucleic acid molecules, such as DNA and/or RNA, or vectors, which code for the complex of the present invention or for individual components for preparing the complex. The feasability of the expression of the nucleic acids encoding a recombinant complex in eukaryotic cells of human origin is successfully documented here, as well as the feasibility to use the complex as an specific apoptotic agents in eukaryotic cells of human origin. This suggests the suitability of nucleic acids coding for a complex according to the invention also for non germ line gene-therapeutic approaches. A person skilled in the art is capable of recognizing the various aspects and possibilities of gene-therapeutic interventions in connection with the various diseases to be treated. In addition to the local application of relatively non-specific vectors (e.g., cationic lipids, non-viral, adenoviral and retroviral vectors), a systemic application with modified target-cell-specific vectors will also become possible in the near future. Complexes and nucleic acid molecules and/or vectors coding for the complexes of present invention, are used for the preparation of medicaments for non-germ line gene therapeutic interventions, for the local or systemic application. An interesting alternative to systemic application are the well-aimed ex vivo transfection of defined cell populations and their return into the organism, or the use of the ex vivo transfected defined cell populations for the preparation of a medicament for the treatment of diseases associated with these cell populations.

Also claimed are cells or in vitro translation systems, which synthesize complete complexes according to the invention or individual components thereof, after transformation and/or transfection with, or addition of the nucleic acid molecules or vectors according to the invention.

Cells or organisms according to the invention are either of prokaryotic origin, especially from *E. coli, B. subtills, S. carnosus, S. coelicolor, Marinococcus* sp., or eukaryotic origin, especially from *Saccharomyces* sp., *Aspergillus* sp., *Spodoptera* sp., *P. pastoris*, primary or cultivated mammalian cells, eukaryotic cell lines (e.g., CHO, Cos or 293) or plants (e.g. *N. tabacum*).

The invention also relates to medicaments comprising the complex according to the present invention and/or the nucleic acid or vectors encoding the complex of present invention. Typically, the complexes according to the invention are administered in physiologically acceptable dosage forms. These include, for example, Tris, NaCl, phosphate buffers and all approved buffer systems, especially including buffer systems, which are characterized by the addition of approved protein stabilizers. The administration is effected, in particular, by parenteral, intravenous, subcutaneous, intramuscular, intratumoral, transnasal administrations, and by transmucosal application. The dosage of the complexes according to the invention to be administered must be established for each application in each disease to be newly treated by clinical phase I studies (dose-escalation studies).

Nucleic acids or vectors, which code for a complex according to the invention, are advantageously administered in physiologically acceptable dosage forms. These include, for example, Tris, NaCl, phosphate buffers and all approved buffer systems, especially including buffer systems, which are characterized by the addition of approved stabilizers for the nucleic acids and/or vectors to be used. The administration is effected, in particular, by parenteral, intravenous, subcutaneous, intramuscular, intratumoral, transnasal administrations, and by transmucosal application.

The complex according to the invention, nucleic acid molecules coding therefore and/or cells or in vitro translation systems can be used for the preparation of a medicament for treating tumor diseases, allergies, autoimmune diseases, and chronic/acute inflammation reactions.

Results

Following the construction of three types of recombinant complexes (immunokinases), first results obtained demonstrate their superior quality with regard to binding specificity as well as cytoxicity.

Construction and Expression of a Recombinant Complex (Immunokinase)

PCR-amplified DAPK2' DNA (FIG. 1) was directionally cloned into the ampicillin-resistant pMS-(L-ANG-Ki-4)-III/G eukaryotic expression vector containing a lgk-leader (L) sequence at the N-terminus, Ki-4(scFv) (component A) and a tandem Myc- and His-Tag epitope at the C-terminus of the expression cassette (FIG. 2) Successful cloning was verified by DNA sequence analysis. Three days after transfection of 293T-cells, the appropriate sized expected recombinant complex (immuno-kinase) pMS-(L-DAPk2-Ki-4)-II/G ($M_r$~66,000) was detected by Western blot analysis of protein mini-preparations. Transfected producer-cells were further cultivated under Zeocin selection pressure in medium culture flasks and were used for larger scale production of the recombinant complex (immunokinase) pMS-(L-DAPk2-Ki-4)-III/G. Under normal culture conditions, between 0.1 and 0.5 µg of the recombinant protein were purified from 1 ml cell culture supernatant by a one step Ni-NTA purification procedure. The intact recombinant complex (immunokinase) was secreted into the supernatant of transfected 293T-cells, as visualized by immunoblot using mouse-anti-penta-His monoclonal antibody.

Figure 2:
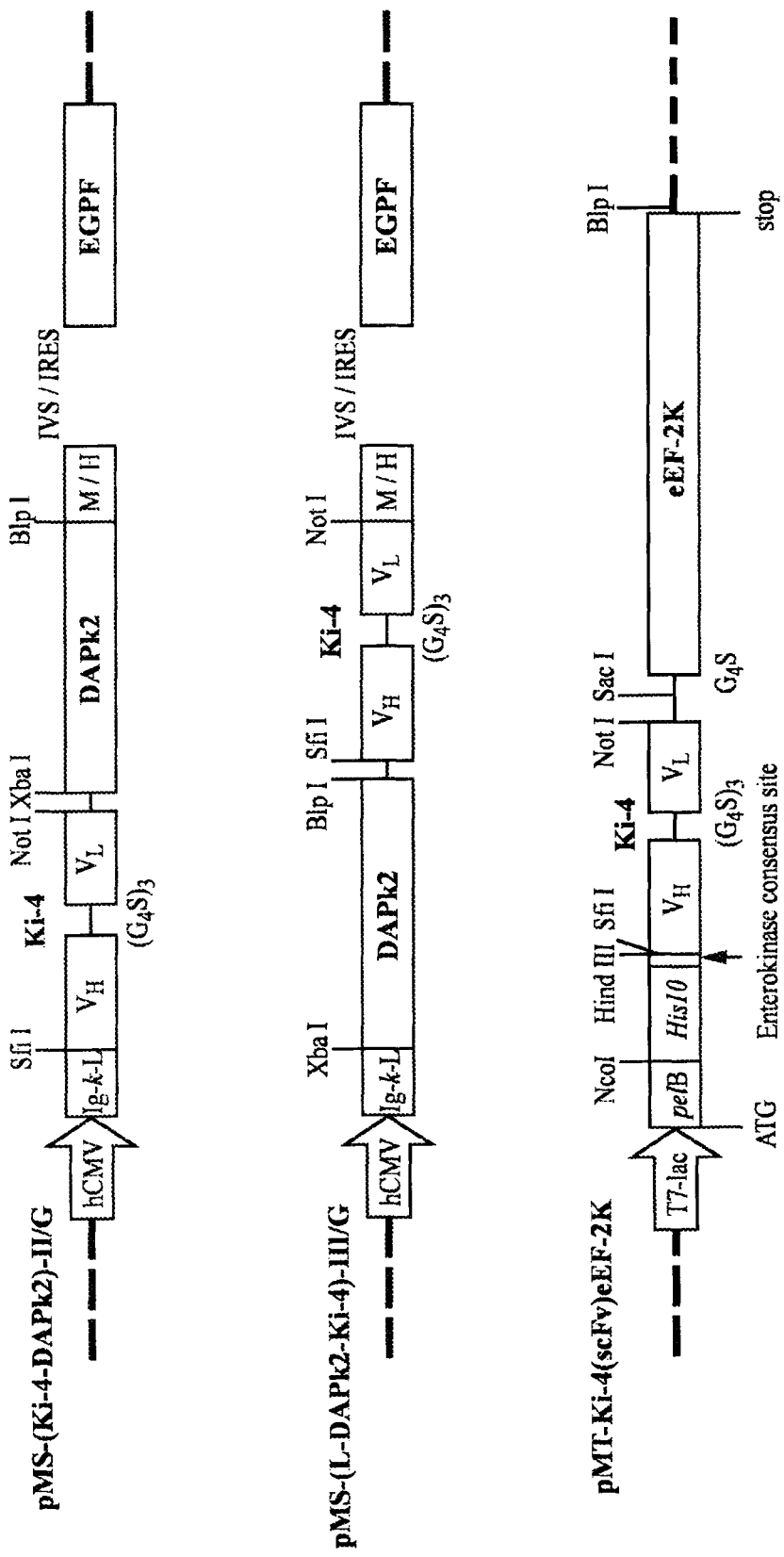
FIG. 2: Schematic structure of the eukaryotic expression cassettes pMS-(L-DAPKk2-Ki-4)-III/G (SEQ ID NO 1), pMS-(Ki-4-DAPk2)-II/G (SEQ ID NO 3) and prokaryotic expression module pMT-Ki-4(scFv)-eEF-2K coding region. Legends: hCMV=human Cyto-megalovirus promotor/enhan-cer; Ig-k-L=Immunoglobin kappa-chain leader sequence; M/H=c-Myc epitope (EQKLISEEDL (SEQ ID NO: 8)) and hexa-Histidine tag; IVS/IRES=intervening sequence/internal ribosome entry site; EGFP=enhanced green fluorescent protein; T7-lac=bacteriophage T7 promotor-lactose operator; pelB=bacterial leader/signal sequence pectate lyase B from *Erwinia carotovora* EC; $His_{10}$=deca-Histidine tag; $V_H$=Immunoglobulin variable heavy-chain; $V_L$=Immunoglobulin variable light-chain; $(G_4S)_3$=(Gly-cinex4−serine)x3 linker; ATG=Translation initiation codon; Stop=Translation termination codon; DAPK2=Death-associated protein-kinase 2/DRP-1; eEF-2K=eukaryotic elongation factor-2 kinase; Ki-4=anti-CD30 immunoglobulin single-chain variable fragment (scFv).

PCR-amplified eEF-2K DNA encoding component B (FIG. 1, 4*a-e*) was directionally cloned into the pET-derived kanamycin-resistant pBM-Ki-4(scFv) prokaryotic expression vector containing an IPTG-inducible lac operator, a pelB signal peptide followed by an enterokinase-cleavable $His_{10}$ tag, and Ki-4(scFv) (component A) (FIG. 2). Successful cloning of the recombinant complex construct pMT-Ki-4(scFv)-eEF-2K was verified by DNA sequence analysis. After transformation, recombinant *E. coli* BL21 Star™ (DE3) clones were cultivated under osmotic stress conditions in the presence of compatible solutes. The recombinant complex (immunokinase) was directed into the periplasmic space and the functional pMT-Ki-4(scFv)-eEF-2K ($M°r$~113,000) protein directly purified by combination of IMAC and SEC to >90% purity. At least 1 mg of purified pMT-Ki-4(scFv)-eEF-2K protein was routinely prepared from 1 liter of bacterial shaking cultures. The intact recombinant complex (immunokinase) was secreted to the periplasmic compartment, as visualized by immunoblot using mouse-anti-penta-His monoclonal antibody.

Binding Properties of Recombinant Complexes (Immunokinases)

Figure 3:
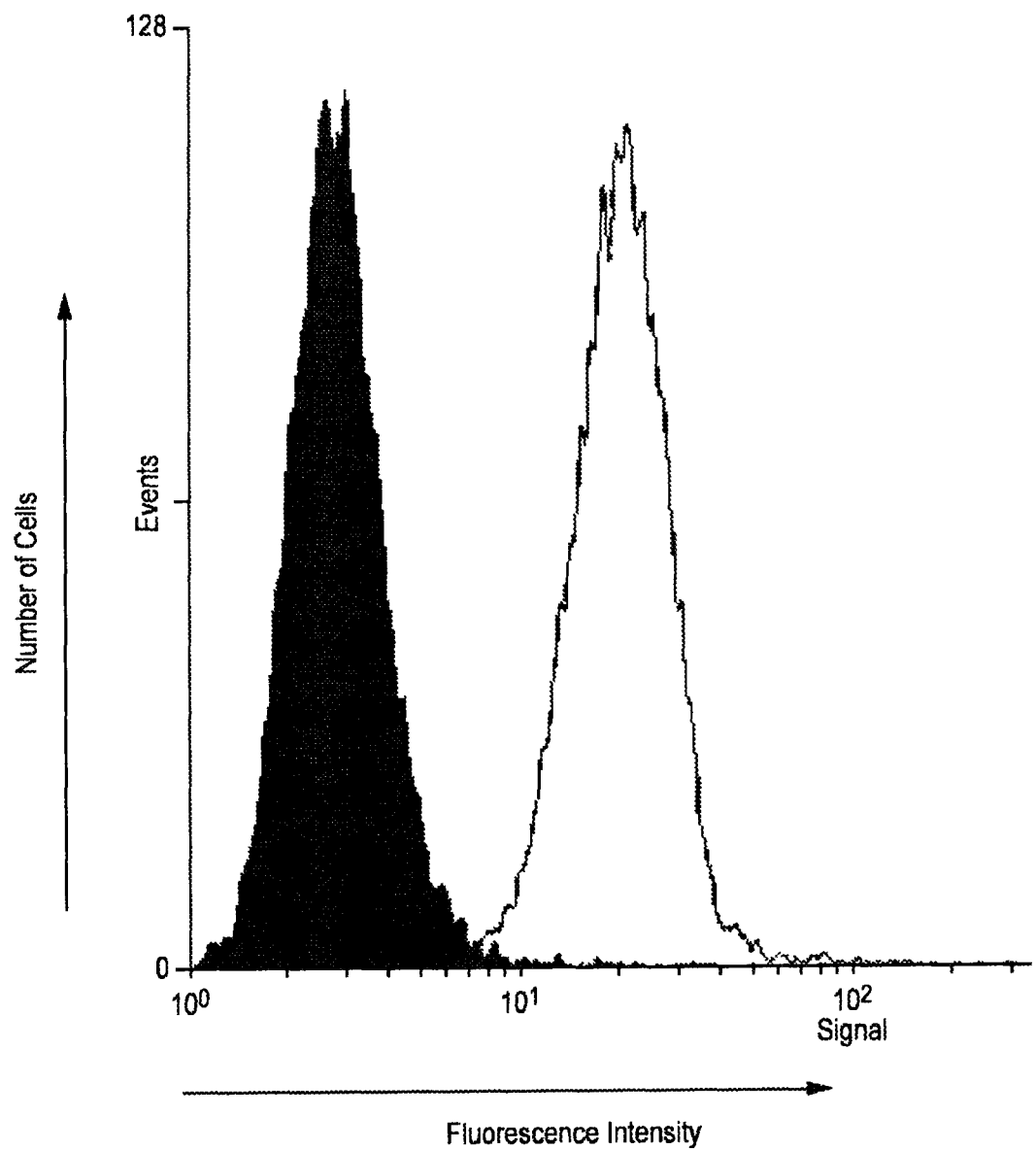
FIG. 3: Binding properties of the recombinant anti-CD30 immunokinases. Binding of pMS-(L-DAPk2-Ki-4)-III/G (SEQ ID NO 2) to CD30-positive cells by flow cytometry. Cells were stained with purified Immunokinase (B) or with PBS as negative control (A).
Figure 4:
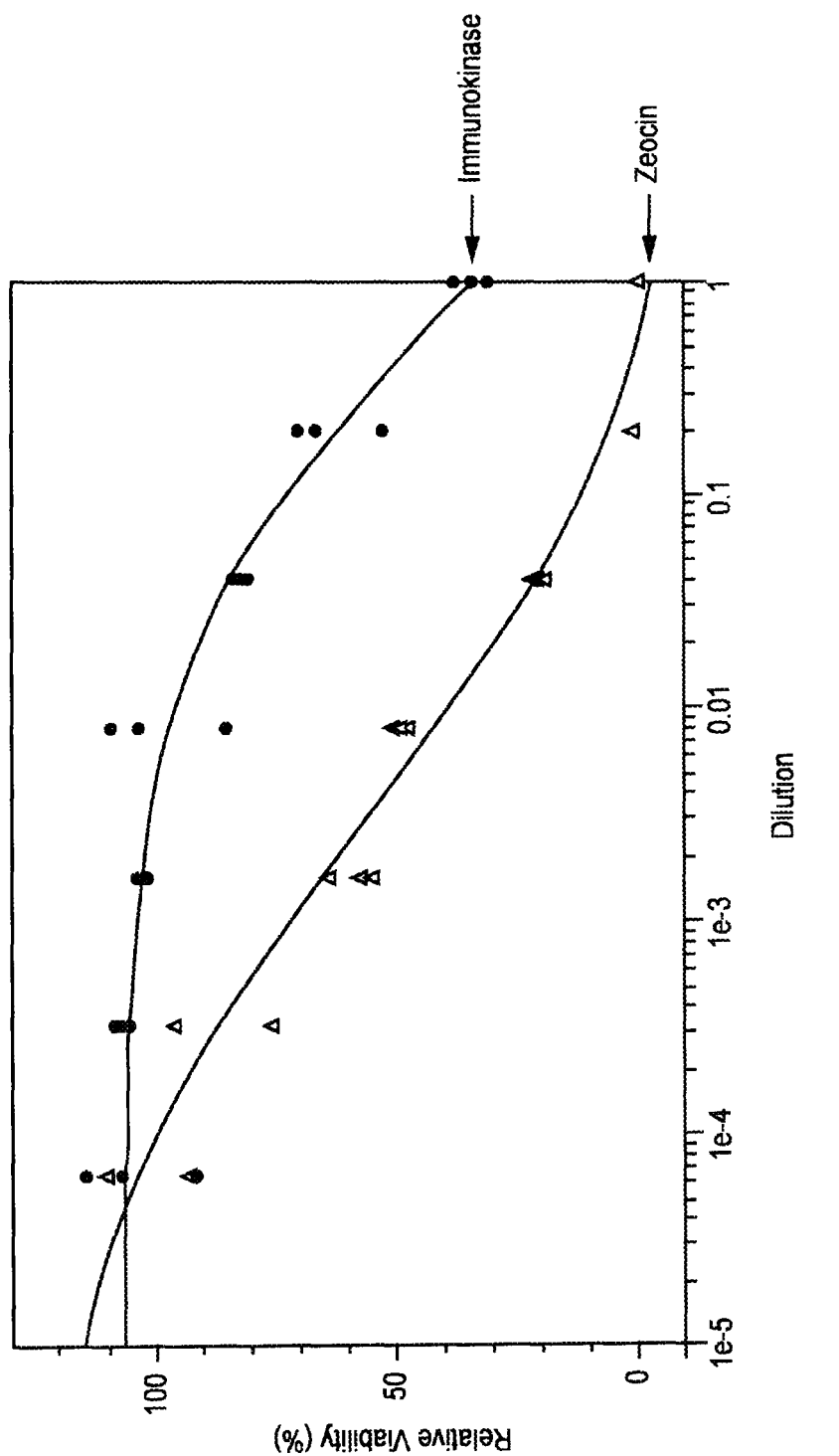
FIG. 4: Growth inhibition of Hodgkin-derived CD30-positive cell lines after incubation with pMS-(L-DAPk2-Ki-4)-III/G as documented by cell-viability assays. L-540Cy cells were treated with different dilutions of recombinant anti-CD30 immunkinase, and their ability to metabolize the XTT to a water-soluble formazan salt was measured as absorbance at 450 and 650 nm. Measurements were performed in triplicate. Results are presented as percentage of untreated control cells and to Zeocin-treated positive control.

Fusing the Ki-4(scFv) coding regions, component A of the complex, to the kinase coding sequences, component B of the complex, did not affect the binding activity of the $V_H/V_L$ antibody format of component A. Component A conferred specificity against the CD30 molecule. The purified recombinant complex (immunokinase) comprising the anti-CD30 component A always bound to the Hodgkin-derived cell line L540Cy as measured by flow cytometry (FIG. 3).

In Vitro Cytotoxic Activity

To characterize the cytotoxic activity of the recombinant complex comprising anti-CD30' (as component A) and kinases (component B) in vitro, the proliferation of different target cells was evaluated after incubation with different amounts of the recombinant complexes (immunokinases) pMS-(L-DAPk2-Ki-4)-III/G and pMT-Ki-4(scFv)-eEF-2K, respectively. Growth inhibition of the CD30-positive cell lines L540Cy and HL60 were documented by a XTT-based colorimetric assay. Toxic effects were observed only against CD30-positive cells with a calculated median $IC_{50}$ of between 4 and 35 ng/ml on L540Cy cells (FIG. 4) The CD30-negative Ramos and 8701-BC cell lines were not affected by recombinant immunokinase concentrations of up to 10 µg/ml. Thus the component A (anti-CD30 scFv) of the complex conferred specificity to the recombinant complex, limiting the cytotoxic effects of the kinase domain to the selected target cells.

EXAMPLES

Bacterial Strains, Oligonucleotides, and Plasmids

*E. coli* XL1-blue (supE44 hsdR17 recA1 endA1 gyr A46 thi relA1 lacF'[pro AB$^+$ lacI$^q$ lacZ ?M15 Tn10(tetr)]) were used for the propagation of plasmids, and *E. coli* BL21 Star™ (DE3) (F$^-$ ompT hsdS$_B$($r_B$-m$_B$-) gal dcm rne131 DE3) as host for synthesis of recombinant immunokinases. Synthetic oligonucleotides were synthesized by MWG Biotech (Ebersberg, Germany). The bacterial expression vector pBM-Ki-4 is derived from the pET27b plasmid (Novagen, Madison, USA), and is used for the expression of the C-terminal fusion of Not I/Blp I-kinase domains to the anti-CD30 scFv (Klimka, A. et al., 1999). The eukaryotic expression vectors pMSKAngII and pMSLAngKIII are derived from the pSec- Tag plasmid (Invitrogen, Carlsbad, USA) and are used for N- or C-terminal fusion of XbaI/BlpI-kinase domains to the Ki-4 (scFv) (Stöcker, M. et al., 2003). Plasmids were prepared by the alkaline lysis method and purified using plasmid preparation kits from Qiagen (Hilden, Germany). Restriction fragments or PCR products were separated by horizontal agarose gel electrophoresis and extracted with QIAquick (Qiagen). All standard cloning procedures were carried out as described by Sambrook, J. et al., 1989.

Cell Culture

All cell lines, including the CD30-positive cell lines L540Cy (Kapp, U. et al., 1992) and HL-60 (Thepen, T. Utrecht, The Netherlands) the CD30-negative cell lines Ramos (ATCC, VA, USA) and 8701-BC (Minafra, S. et al., 1989) and the producer cell line 293T (ATCC) were cultivated in complex medium (RPMI 1640) supplemented with 10% (v/v) heat-inactivated fetal calf serum, 50 µg/ml penicillin, 100 µg/ml streptomycin and 2 m M L-glutamine. All cells were cultured at 37° C. in a 5% $CO_2$ in air atmosphere. For the selection of transfected cells, Zeocin (Invitrogen) was added to a final concentration of 100 µg/ml.

Construction and Expression of Recombinant Complexes (Immunokinases)

Cloning and expression of pMS-(L-DAPk2-Ki-4)-III/G (SEQ ID NO 1) and pMS-(Ki-4-DAPk2)-II/G (SEQ ID NO 3)

For the construction of a vector encoding a recombinant complex with N- or C-terminal DAP-kinase 2 (DAPk2)-fusions, DAPk2 was PCR amplified to introduce the restriction sites XbaI and BlpI. After XbaI/BlpI-digestion, the PCR-product was cloned into the eukaryotic expression vector pMS-(L-ANG-Ki-4)-III/G and pMS-(Ki-4-ANG)-II/G respectively, digested with the same restriction enzymes. The resulting recombinant constructs pMS-(L-DAPk2-Ki-4)-III/G (SEQ ID NO: 1) and pMS-(Ki-4-DAPk2)-II/G (SEQ ID NO: 3) encoding the immukinase proteins L-DAPk2-Ki-4-MH (SEQ ID NO 2) and L-Ki-4-DAPk2-MH (SEQ ID NO 4) were verified by sequence analysis. After TransFast-mediated (Promega, Mannhein, Germany) transformation into 293T-cells, the recombinant immunokinase was expressed as described by Stöcker M. et al., 2003. Briefly, one µg plasmid-DNA and 3 µl TransFast have been used according to the manufactures protocol for 12 well cell culture plates. Transfection efficiency was between 75 and 95% determined by counting green fluorescent cells. 3 days after initial transfection, cell culture supernatants were analyzed for recombinant protein. Subsequently, transfected cells were transferred into medium-sized cell culture flasks (Nunc; 85 m²) and grown in RPMI complex medium supplemented with 100 µg/ml Zeocin. One to two weeks productively transfected clones were green fluorescing and hence could be detected by fluorescence microscopy. Transfected cell populations were established by subcultivation of these clones. Purifications of the His-tagged proteins were accomplished by the Ni-NTA metal-affinity method (Hochuli, V., 1989, Porath, J. et al., 1975) (Qiagen). The protein purification followed a modified protocol for the purification of native protein from Qiagen (*The Expressionist* 07/97). For protein mini-preparation, 900 µl centrifugation-cleared cell culture supernatant was supplemented with 300 µl of 4× incubation buffer (200 mM $NaH_2PO_4$, pH 8.0; 1.2M NaCl; 40 mM Imidazol) and 30 µl 50% Ni-NTA. Following 1 h incubation, the Ni-NTA resin was pelleted by centrifugation. After washing the sediment twice in 175 µl 1× incubation buffer, bound protein was eluted with 30 µl of elution buffer (50 mM $NaH_2PO_4$, pH 8.0; 1.2M NaCl; and 40 mM imidazol) and 30 µl 50% Ni-NTA. Following an 1 h incubation, the Ni-NTA resin was pelleted by centrifugation. After washing the sediment twice in 175 µl 1× incubation buffer, bound protein was eluted with 30 µl of elution buffer (50 mM $NaH_2PO_4$, pH8.0; 300 mM NaCl; 250 mM Imidazol) for 20 min at RT. Larger scale purification of eukaryotically-expressed proteins up to 500 ml cell culture supernatant was performed on a BioLogic workstation (Bio-Rad, USA). Cell culture supernatants were loaded onto a Ni-NTA column and following elution of the His-tagged proteins were made under the conditions described above.

Cloning and Expression of pMT-KI-4(scFv)-eEF-2K

The eukaryotic elongation factor-2 kinase (eEF-2k) was amplified by PCR to introduce the restriction sites NotI and BlpI. After NotI/BlpI-digestion, the PCR-fragment was cloned into the bacterial expression vector pBM-Ki-4, digested with the same restriction enzymes. The resulting recombinant construct pMT-Ki-4(scFv)-eEF-2K (SEQ ID NO: 5) was verified by DNA sequence analysis. After transformation into BL21 Star™ (DE3), the immunokinase Ki-4 (scFv)-eEF-2K (SEQ ID NO 6) were periplasmically expressed under osmotic stress in the presence of compatible solutes as described by Barth, S. et al. 2000. Briefly, transformed bacteria were harvested 15 h after IPTG induction. The bacterial pellet was resuspended in sonication-buffer (75 mM Tris/HCl (pH 8), 300 mM NaCl, 1 capsule of protease inhibitors/50 ml (Complete™, Roche Diagnostics, Mannheim, Germany), 5 mM DTT, 10 mM EDTA, 10% (v/v) glycerol) at 4° C. and sonicated 6 times for 30 s at 200 W. The m22(scFv)-ETA' fusion proteins were enriched by IMAC (immobilized metal-ion affinity chromatography) using nickel-nitriloacetic chelating Sepharose (Qiagen) and SEC (size exclusion chromatography) with Bio-Prep SE-100/17 (Biorad, München, Germany) columns according to the manufacturer's instructions. Recombinant Protein was eluted with PBS (pH 7.4) and 1 M NaCl, analyzed by Sodium dodecyl sulfate/polyacrylamide gel electrophoresis (SDS-PAGE), quantified by densitometry (GS-700 Imaging Densitometer; Biorad) after Coomassie staining in comparison with BSA standards and verified by Bradford assays (Biorad).

SDS—PAGE and Western Blot Analysis

SDS-PAGE, Coomassie staining, and Western blotting were performed as described by Barth, S. et al., 1998. Briefly, recombinant His-tagged immunokinases were detected by mouse-anti-penta-His moab (Qiagen). Bound antibody was detected by a horseradish-conjugated donkey-anti-mouse-IgG moab (Dianova, Hamburg, Germany), followed by ECL-mediated (Amersham Biosciences, Freiburg, Germany), chemiluminescence reaction and exposition to appropriate X-ray film (Roche, Penzberg, Germany) or alkaline-phosphatase-conjugated anti-mouse-IgG moab (Sigma Chemical Co., Deisenhofen, Germany) and a solution of Tris-HCl (pH 8.0) and 0.2 mg/ml naphtol-AS-Bi-phosphate (Sigma Chemical Co.) supplemented with 1 mg/ml Fast-Red (Serva, Heidelberg, Germany).

Cell Membrane (CM) ELISA

The binding activity of recombinant complexes (immunokinases) were determined by CM-ELISA using biological active membranes of tumor cells as described recently by Tur, M K. et al., 2003. Briefly, ELISA Maxisorp-Plates (Nalge Nunc International, Roskilde, Denmark) were coated with 100 µl (~0.9 mg protein/ml) freshly prepared membrane fractions of CD30-positive L540Cy/HL60 cells and Ramos/8701-BC as control in 0.02 M bicarbonate buffer, pH 9.6, overnight at 4° C. Plates were washed five times with PBS (pH 7.4) containing 0.2% Tween 20 (TPBS) and blocked with 200 µl 2% BSA in PBS. After overnight incubation at 4° C., plates were washed five times with TPBS and 1-10 µg/ml of recombinant immunokinases diluted with 0.5% BSA (w/v) and 0.05% Tween 20 (v/v) in PBS was added to the plates and incubated at RT (23° C.) for 1 h. Peroxidase labeled anti-His IgG conjugate (Qiagen) were added diluted with 0.5% BSA and 0.05% Tween 20 in PBS according to manufactures instructions. Bound antibodies were visualized after addition of 100 µl 2',2'-azino-bis(3-ethylbenzthiazoline-6-sulphonic acid) (ABTS) solution (Roche Molecular Biochemical's, Mannheim, Germany) by measuring the extinction at 415 nm with an ELISA-Reader (MWG Biotech).

Flow Cytometry Analyses

Cell binding activity of the recombinant complexes (immunokinases) expressed in E. coli BL21 Star™ (DE3) was evaluated using a FACSCalibur flow cytometry instrument and CellQuest software (Becton Dickinson, Heidelberg, Germany). Cells were stained with recombinant protein as described (25). Briefly, ten thousand events were collected for each sample, and analyses of Intact cells were performed using appropriate scatter gates to exclude cellular debris and aggregates. $5 \times 10^5$ cells were incubated for 1 h on ice with 50 µl of bacterial protein extract at a concentration of 30-40 µg/ml or 100 µl of the immunokuinase containing supernatants respectively. The cells were washed with PBS buffer containing 0.2% w/v BSA and 0.05% w/v sodium azide (PBA) and then incubated for 30 min with anti-penta-His moab (Qiagen) diluted 1:2 in PBA buffer. Cells were washed and incubated with fluorescein-iso-thiocyanate (FITC)-labeled goat-anti-mouse IgG (DAKO Diagnostica, Hamburg, Germany) for 1 h at 4° C. After a final wash, the cells were treated with 2 µl 6.25 mg/ml propidiumiodide and subsequently analyzed on a FACScalibur (Becton Dickison, Heidelberg, Germany).

Colorimetric Cell Proliferation Assay

The cytotoxic effect of the recombinant complexes (immunokinases) on target cells was determined by measurement of metabolization of yellow tetrazolium salt (XTT) to a water soluble orange formazan dye was determined as published by Barth, S. et al. 2000. Various dilutions of the recombinant immunokinase were distributed in 100 µl-aliquots in 96-well plates. Two-four$\times 10^4$ target cells in 100 µl aliquots of complete medium were added and the plates were incubated for 48 h at 37° C. Afterwards, the cell cultures were pulsed with 100 µl fresh culture medium supplemented with XTT/PMS (final concentrations of 0.3 mg and 0.383 ng respectively) for 4 h. The spectrophotometrical absorbances of the samples were measured at 450 and 650 nm (reference wavelength) with an ELISA reader (MWG Biotech). The concentration required to achieve a 50% reduction of protein synthesis ($IC_{50}$) relative to untreated control cells and to 1% Triton X treated positive controls was calculated graphically via Excel generated diagrams. All measurements were done in triplicate.

REFERENCES

1. Kaminski, M. S., Zasadny, K. R., Francis, I. R., Fenner, M. C., Ross, C. W., Milik, A. W., Estes, J., Tuck, M., Regan, D., Fisher, S., Glenn, S. D., and Wahl, R. L. Iodine-131-anti-B1 radioimmunotherapy for B-cell lymphoma. J Clin Oncol, 14: 1974-1981, 1996.
2. Pennell, C. A. and Erickson, H. A. Designing immunotoxins for cancer therapy. Immunol Res, 25: 177-191, 2002.
3. Chaudhary, V. K., Gallo, M. G., FitzGerald, D. J., and Pastan, I. A recombinant single-chain immunotoxin composed of anti-Tac variable regions and a truncated diphtheria toxin. Proc Natl Acad Sci USA, 87: 9491-9494, 1990.
4. Brinkmann, U., Keppler-Hafkemeyer, A., and Hafkemeyer, P. Recombinant immunotoxins for cancer therapy. Expert Opin Biol Ther, 1: 693-702, 2001.
5. Frankel, A. E., Tagge, E. P., and Willingham, M. C. Clinical trials of targeted toxins. Semin Cancer Biol, 6: 307-317, 1995.
6. Youle, R. J., Newton, D., Wu, Y. N., Gadina, M., and Rybak, S. M. Cytotoxic ribonucleases and chimeras in cancer therapy. Crit Rev Ther Drug Carrier Syst, 10:1-28, 1993.
7. Fett, J. W., Strydom, D. J., Lobb, R. R., Alderman, E. M., Bethune, J. L., Riordan, J. F., and Vallee, B. L. Isolation and characterization of angiogenin, an angiogenic protein from human carcinoma cells. Biochemistry, 24: 5480-5486, 1985.
8. Huhn, M., Sasse, S., Tur, M. K., Matthey, B., Schinkothe, T., Rybak, S. M., Barth, S., and Engert, A. Human angiogenin fused to human CD30 ligand (Ang-CD30L) exhibits specific cytotoxicity against CD30-positive lymphoma. Cancer Res, 61: 8737-8742, 2001.
9. Newton, D. L. and Rybak, S. M. Preparation and preclinical characterization of RNase-based immunofusion proteins. Methods Mol Biol, 160: 387-406, 2001.
10. Goueli, S. Protein Kinases as Drug Targets in High-Throughput Systems. Promega Notes, 75: 24-28, 2000.
11. Manning, G., Whyte, D. B., Martinez, R., Hunter, T., and Sudarsanam, S. The Protein Kinase Complement of the Human Genome. Science, 298: 1912-1934, 2002.
12. Hanks, S. K., Quinn, A. M., and Hunter, T. The protein kinase family: conserved features and deduced phylogeny of the catalytic domains. Science, 241: 42-52, 1988.
13. Ryazanov, A. G., Pavur, K. S., and Dorovkov, M. V. Alpha-kinases: a new class of protein kinases with a novel catalytic domain. Curr Biol, 9: 43-45, 1999.
14. Braun, A. P. and Schulman, H. The multifunctional calcium/calmodulin-dependent protein kinase: from form to function. Annu Rev Physiol, 57: 417-445, 1995.
15. Deiss, L. P., Feinstein, E., Berissi, H., Cohen, O., and Kimchi, A. Identification of a novel serine/threonine kinase and a novel 15-kD protein as potential mediators of the gamma interferon-induced cell-death. Genes Dev, 9: 15-30, 1995.
16. Nakatsuka, S., Takakuwa, T., Tomita, Y., Hoshida, Y., Nishiu, M., Yamaguchi, M., Nishii, K., Yang, W. I., and Aozasa, K. Hypermethylation of death-associated protein (DAP) kinase CpG island is frequent not only in B-cell but also in T- and natural killer (NK)/T-cell malignancies. Cancer Sci, 94: 87-91, 2003.
17. Cohen, O., Feinstein, E., and Kimchi, A. DAP-kinase is a Ca2+/calmodulin-dependent, cytoskeletal-associated protein kinase, with cell death-inducing functions that depend on its catalytic activity. Embo J, 16: 998-1008, 1997.
18. Pavur, K. S., Petrov, A. N., and Ryazanov, A. G. Mapping the functional domains of elongation factor-2 kinase. Biochemistry, 39: 12216-12224, 2000.
19. Diggle, T. A., Subkhankulova, T., Lilley, K. S., Shikotra, N., Willis, A. E., and Redpath, N. T. Phosphorylation of elongation factor-2 kinase on serine 499 by cAMP-dependent protein kinase induces Ca2+/calmodulin-independent activity. Biochem J, 353: 621-626, 2001.

The invention claimed is:

1. A synthetic, soluble complex comprising at least one component A and at least one component B, whereby component A comprises an scFv that binds to a Cluster of Differentiation antigen (CD) that internalizes upon binding of component A of said complex, and component B comprises death-associated protein kinase 2 (DAPK2) and has a constitutive catalytic kinase activity to affect cell biosynthesis and/or signaling, wherein the complex comprises residues 1-573 of amino acid sequence SEQ ID NO: 2 or residues 1-576 of SEQ ID NO: 4.

2. The complex according to claim 1 wherein the component A is bound to the extra-cellular surface structure.

3. The complex according to claim 1, wherein component A further comprises at least one additional binding domain.

4. The complex according to claim 1, whereby the constitutive kinase activity of component B directly activates or inactivates components of a cell-regulatory pathway through phosphorylation, acetylation, methylation, prenylation, or sulfation, thereby altering the function, gene expression, or viability of a target cell that binds component A.

5. The complex according to claim 1, comprising one or more supplementary component S which regulates protein biosynthesis an the transcription and/or translation level, and/or enables purification and/or detection of the complex, and/or facilitates translocation of at least component B into the target cell, and/or intracellular separation and/or activation of component B, wherein the component S is selected from the group of inducible promoters, leader sequences, affinity tags, His tags, translocation domain, amphiphatic sequences and synthetic pro-granzyme B.

6. A composition comprising the complex of claim 1 disposed in a physiologically acceptable dosage form.

7. The complex of claim 1 wherein the constitutive catalytic kinase causes cell death after internalization of the complex into the cell.

8. The complex of claim 1 wherein said CD is selected from the group consisting of CD30 and CD40.

* * * * *

SEQUENCE LISTING

<160> NUMBER OF SEQ ID NOS: 9

<210> SEQ ID NO 1
<211> LENGTH: 1785
<212> TYPE: DNA
<213> ORGANISM: Artificial Sequence
<220> FEATURE:
<223> OTHER INFORMATION: Description of Artificial Sequence: pMS-(L-DAPK2'-Ki-4)-III/G open reading frame (ORF)
<220> FEATURE:
<221> NAME/KEY: N_region
<222> LOCATION: (1)..(21)
<223> OTHER INFORMATION: immunoglobin kappa chain leader sequence
<220> FEATURE:
<221> NAME/KEY: CDS
<222> LOCATION: (1)..(1785)

<400> SEQUENCE: 1

```
atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac tct aga atg gtc cag gcc tcg atg agg agc cca        96
Gly Ser Thr Gly Asp Ser Arg Met Val Gln Ala Ser Met Arg Ser Pro
            20                  25                  30 aat atg gag acg ttc aaa cag cag aag gtg gag gac ttt tat gat att       144
Asn Met Glu Thr Phe Lys Gln Gln Lys Val Glu Asp Phe Tyr Asp Ile
        35                  40                  45 gga gag gag ctg ggc agt ggc cag ttt gcc atc gtg aag aag tgc cgg       192
Gly Glu Glu Leu Gly Ser Gly Gln Phe Ala Ile Val Lys Lys Cys Arg
    50                  55                  60 gag aag agc acg ggg ctg gag tat gca gcc aag ttc att aag aag agg       240
Glu Lys Ser Thr Gly Leu Glu Tyr Ala Ala Lys Phe Ile Lys Lys Arg
65                  70                  75                  80 cag agc cgg gcc agc cgt cgg ggc gtg tgc cgg gag gaa atc gag cgg       288
Gln Ser Arg Ala Ser Arg Arg Gly Val Cys Arg Glu Glu Ile Glu Arg
                85                  90                  95 gag gtg agc atc ctg cgg cag gtg ctg cac ccc aac atc atc acg ctg       336
Glu Val Ser Ile Leu Arg Gln Val Leu His Pro Asn Ile Ile Thr Leu
            100                 105                 110 cac gac gtc tat gag aac cgc acc gac gtg gtg ctc atc ctt gag cta       384
His Asp Val Tyr Glu Asn Arg Thr Asp Val Val Leu Ile Leu Glu Leu
        115                 120                 125 gtg tcc gga gga gaa ctg ttt gat ttc ctg gcc cag aag gag tcg tta       432
Val Ser Gly Gly Glu Leu Phe Asp Phe Leu Ala Gln Lys Glu Ser Leu
    130                 135                 140 agt gag gag gaa gcc acc agc ttc att aag cag atc ctg gat ggg gtg       480
Ser Glu Glu Glu Ala Thr Ser Phe Ile Lys Gln Ile Leu Asp Gly Val
145                 150                 155                 160 aat tac ctt cac aca aag aaa att gct cac ttt gat ctc aag cca gaa       528
Asn Tyr Leu His Thr Lys Lys Ile Ala His Phe Asp Leu Lys Pro Glu
                165                 170                 175 aac atc atg ttg tta gac aag aat atc cca att cca cac atc aag ctg       576
Asn Ile Met Leu Leu Asp Lys Asn Ile Pro Ile Pro His Ile Lys Leu
            180                 185                 190 att gac ttt ggc ctg gct cac gaa ata gaa gat gga gtt gaa ttt aaa       624
Ile Asp Phe Gly Leu Ala His Glu Ile Glu Asp Gly Val Glu Phe Lys
        195                 200                 205 aac att ttt ggg aca cct gaa ttt gtt gct cca gaa atc gtg aac tat       672
Asn Ile Phe Gly Thr Pro Glu Phe Val Ala Pro Glu Ile Val Asn Tyr
    210                 215                 220 aac att ttt ggg aca cct gaa ttt gtt gct cca gaa atc gtg aac tat       720
Asn Ile Phe Gly Thr Pro Glu Phe Val Ala Pro Glu Ile Val Asn Tyr
225                 230                 235                 240
```

| | | |
|---|---|---|
| tat atc ctt cta agt gga gcg tcc ccc ttc ctg gga gac aca aaa caa<br>Tyr Ile Leu Leu Ser Gly Ala Ser Pro Phe Leu Gly Asp Thr Lys Gln<br>245 250 255 | | 768 |
| gaa acc ctg gca aat atc act gct gtg agt tac gac ttt gat gag gaa<br>Glu Thr Leu Ala Asn Ile Thr Ala Val Ser Tyr Asp Phe Asp Glu Glu<br>260 265 270 | | 816 |
| ttc ttc agc cag aca agc gag ctg gcc aag gac ttc att cgg aag ctt<br>Phe Phe Ser Gln Thr Ser Glu Leu Ala Lys Asp Phe Ile Arg Lys Leu<br>275 280 285 | | 864 |
| ctt gtg aaa gag acc cgg aaa cgg ctt acc atc caa gag gct ctc aga<br>Leu Val Lys Glu Thr Arg Lys Arg Leu Thr Ile Gln Glu Ala Leu Arg<br>290 295 300 | | 912 |
| cat ccc tgg atc gga tcc aaa cta gct gag cac gaa ggt gac gcg gcc<br>His Pro Trp Ile Gly Ser Lys Leu Ala Glu His Glu Gly Asp Ala Ala<br>305 310 315 320 | | 960 |
| cat ccc tgg atc gga tcc aaa cta gct gag cac gaa ggt gac gcg gcc<br>His Pro Trp Ile Gly Ser Lys Leu Ala Glu His Glu Gly Asp Ala Ala<br>325 330 335 | | 1008 |
| gca aag cct ggg gcc gca gtg aag atg tcc tgc aag gct tct ggc tac<br>Ala Lys Pro Gly Ala Ala Val Lys Met Ser Cys Lys Ala Ser Gly Tyr<br>340 345 350 | | 1056 |
| acc ttt act gac tac tgg atg cac tgg gtt aaa cag agg cct gga cag<br>Thr Phe Thr Asp Tyr Trp Met His Trp Val Lys Gln Arg Pro Gly Gln<br>355 360 365 | | 1104 |
| ggt ctg gaa tgg att gga tac att aat cct aac act gct tat act gac<br>Gly Leu Glu Trp Ile Gly Tyr Ile Asn Pro Asn Thr Ala Tyr Thr Asp<br>370 375 380 | | 1152 |
| tac aat cag aaa ttc aag gac aag gcc aca ttg act gca gac aaa tcc<br>Tyr Asn Gln Lys Phe Lys Asp Lys Ala Thr Leu Thr Ala Asp Lys Ser<br>385 390 395 400 | | 1200 |
| tcc agc aca gcc tac atg caa ctg cgc agc ctg acc tct gag gat tct<br>Ser Ser Thr Ala Tyr Met Gln Leu Arg Ser Leu Thr Ser Glu Asp Ser<br>405 410 415 | | 1248 |
| gca gtc tat tac tgt gca aaa aag aca act cag act acg tgg ggg ttt<br>Ala Val Tyr Tyr Cys Ala Lys Lys Thr Thr Gln Thr Thr Trp Gly Phe<br>420 425 430 | | 1296 |
| cct ttt tgg ggc caa ggg acc acg gtc acc gtc tcc tca ggt gga ggc<br>Pro Phe Trp Gly Gln Gly Thr Thr Val Thr Val Ser Ser Gly Gly Gly<br>435 440 445 | | 1344 |
| ggt tca ggc gga ggt ggc tct ggc ggt ggc gga tcg gac att gtg ctg<br>Gly Ser Gly Gly Gly Ser Gly Gly Gly Gly Ser Asp Ile Val Leu<br>450 455 460 | | 1392 |
| acc cag tct cca aaa tcc atg gcc atg tca gtc gga gag agg gtc acc<br>Thr Gln Ser Pro Lys Ser Met Ala Met Ser Val Gly Glu Arg Val Thr<br>465 470 475 480 | | 1440 |
| ttg agc tgc aag gcc agt gag aat gtg gat tct ttt gtt tcc tgg tat<br>Leu Ser Cys Lys Ala Ser Glu Asn Val Asp Ser Phe Val Ser Trp Tyr<br>485 490 495 | | 1488 |
| caa cag aaa cca ggc cag tct cct aaa ctg ctg ata tac ggg gcc tcc<br>Gln Gln Lys Pro Gly Gln Ser Pro Lys Leu Leu Ile Tyr Gly Ala Ser<br>500 505 510 | | 1536 |
| aac cgg tac act ggg gtc ccc gat cgc ttc gca ggc agt gga tct gga<br>Asn Arg Tyr Thr Gly Val Pro Asp Arg Phe Ala Gly Ser Gly Ser Gly<br>515 520 525 | | 1584 |
| aga gat ttc act ctg acc atc agc agt gtg cag gct gaa gac ctt gca<br>Arg Asp Phe Thr Leu Thr Ile Ser Ser Val Gln Ala Glu Asp Leu Ala<br>530 535 540 | | 1632 |
| gat tat cac tgt gga cag aat tac agg tat ccg ctc acg ttc ggt gct<br>Asp Tyr His Cys Gly Gln Asn Tyr Arg Tyr Pro Leu Thr Phe Gly Ala | | 1680 |

```
                        545                 550                 555                 560
ggc  acc  aag  ctg  gaa  atc  aaa  cgg  gcg  gcc  gca  ggg  ccc  gaa  caa  aaa        1728
Gly  Thr  Lys  Leu  Glu  Ile  Lys  Arg  Ala  Ala  Ala  Gly  Pro  Glu  Gln  Lys
                        565                 570                 575 ctc  atc  tca  gaa  gag  gat  ctg  aat  agc  gcc  gtc  gac  cat  cat  cat  cat        1776
Leu  Ile  Ser  Glu  Glu  Asp  Leu  Asn  Ser  Ala  Val  Asp  His  His  His  His
                        580                 585                 590 cat  cat  tga                                                                          1785
His  His <210> SEQ ID NO 2
<211> LENGTH: 594
<212> TYPE: PRT
<213> ORGANISM: Artificial Sequence
<220> FEATURE:
<223> OTHER INFORMATION: Synthetic Construct

<400> SEQUENCE: 2

Met Glu Thr Asp Thr Leu Leu Leu Trp Val Leu Leu Leu Trp Val Pro
  1               5                  10                  15

Gly Ser Thr Gly Asp Ser Arg Met Val Gln Ala Ser Met Arg Ser Pro
             20                  25                  30

Asn Met Glu Thr Phe Lys Gln Gln Lys Val Glu Asp Phe Tyr Asp Ile
         35                  40                  45

Gly Glu Glu Leu Gly Ser Gly Gln Phe Ala Ile Val Lys Lys Cys Arg
     50                  55                  60

Glu Lys Ser Thr Gly Leu Glu Tyr Ala Ala Lys Phe Ile Lys Lys Arg
 65                  70                  75                  80

Gln Ser Arg Ala Ser Arg Arg Gly Val Cys Arg Glu Ile Glu Arg
                 85                  90                  95

Glu Val Ser Ile Leu Arg Gln Val Leu His Pro Asn Ile Ile Thr Leu
            100                 105                 110

His Asp Val Tyr Glu Asn Arg Thr Asp Val Val Leu Ile Leu Glu Leu
        115                 120                 125

Val Ser Gly Gly Glu Leu Phe Asp Phe Leu Ala Gln Lys Glu Ser Leu
    130                 135                 140

Ser Glu Glu Glu Ala Thr Ser Phe Ile Lys Gln Ile Leu Asp Gly Val
145                 150                 155                 160

Asn Tyr Leu His Thr Lys Lys Ile Ala His Phe Asp Leu Lys Pro Glu
                165                 170                 175

Asn Ile Met Leu Leu Asp Lys Asn Ile Pro Ile Pro His Ile Lys Leu
            180                 185                 190

Ile Asp Phe Gly Leu Ala His Glu Ile Glu Asp Gly Val Glu Phe Lys
        195                 200                 205

Asn Ile Phe Gly Thr Pro Glu Phe Val Ala Pro Glu Ile Val Asn Tyr
    210                 215                 220

Asn Ile Phe Gly Thr Pro Glu Phe Val Ala Pro Glu Ile Val Asn Tyr
225                 230                 235                 240

Tyr Ile Leu Leu Ser Gly Ala Ser Pro Phe Leu Gly Asp Thr Lys Gln
                245                 250                 255

Glu Thr Leu Ala Asn Ile Thr Ala Val Ser Tyr Asp Phe Asp Glu Glu
            260                 265                 270

Phe Phe Ser Gln Thr Ser Glu Leu Ala Lys Asp Phe Ile Arg Lys Leu
        275                 280                 285

Leu Val Lys Glu Thr Arg Lys Arg Leu Thr Ile Gln Glu Ala Leu Arg
    290                 295                 300
```

```
His Pro Trp Ile Gly Ser Lys Leu Ala Glu His Glu Gly Asp Ala Ala
305                 310                 315                 320

His Pro Trp Ile Gly Ser Lys Leu Ala Glu His Glu Gly Asp Ala Ala
                325                 330                 335

Ala Lys Pro Gly Ala Ala Val Lys Met Ser Cys Lys Ala Ser Gly Tyr
            340                 345                 350

Thr Phe Thr Asp Tyr Trp Met His Trp Val Lys Gln Arg Pro Gly Gln
                355                 360                 365

Gly Leu Glu Trp Ile Gly Tyr Ile Asn Pro Asn Thr Ala Tyr Thr Asp
        370                 375                 380

Tyr Asn Gln Lys Phe Lys Asp Lys Ala Thr Leu Thr Ala Asp Lys Ser
385                 390                 395                 400

Ser Ser Thr Ala Tyr Met Gln Leu Arg Ser Leu Thr Ser Glu Asp Ser
                405                 410                 415

Ala Val Tyr Tyr Cys Ala Lys Lys Thr Thr Gln Thr Thr Trp Gly Phe
            420                 425                 430

Pro Phe Trp Gly Gln Gly Thr Thr Val Thr Val Ser Ser Gly Gly Gly
                435                 440                 445

Gly Ser Gly Gly Gly Gly Ser Gly Gly Gly Gly Ser Asp Ile Val Leu
        450                 455                 460

Thr Gln Ser Pro Lys Ser Met Ala Met Ser Val Gly Glu Arg Val Thr
465                 470                 475                 480

Leu Ser Cys Lys Ala Ser Glu Asn Val Asp Ser Phe Val Ser Trp Tyr
                485                 490                 495

Gln Gln Lys Pro Gly Gln Ser Pro Lys Leu Leu Ile Tyr Gly Ala Ser
            500                 505                 510

Asn Arg Tyr Thr Gly Val Pro Asp Arg Phe Ala Gly Ser Gly Ser Gly
                515                 520                 525

Arg Asp Phe Thr Leu Thr Ile Ser Ser Val Gln Ala Glu Asp Leu Ala
        530                 535                 540

Asp Tyr His Cys Gly Gln Asn Tyr Arg Tyr Pro Leu Thr Phe Gly Ala
545                 550                 555                 560

Gly Thr Lys Leu Glu Ile Lys Arg Ala Ala Ala Gly Pro Glu Gln Lys
                565                 570                 575

Leu Ile Ser Glu Glu Asp Leu Asn Ser Ala Val Asp His His His His
            580                 585                 590

His His

<210> SEQ ID NO 3
<211> LENGTH: 1794
<212> TYPE: DNA
<213> ORGANISM: Artificial Sequence
<220> FEATURE:
<223> OTHER INFORMATION: pMS-(Ki-4-DAPK2')-II/G ORF
<220> FEATURE:
<221> NAME/KEY: CDS
<222> LOCATION: (1)..(1794)
<220> FEATURE:
<221> NAME/KEY: N_region
<222> LOCATION: (1)..(21)
<223> OTHER INFORMATION: immunoglobin kappa chain leader sequence

<400> SEQUENCE: 3 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac gcg gcc cag ccg gcc atg gcc cag gtc aag ctg        96
```

```
                Gly Ser Thr Gly Asp Ala Ala Gln Pro Ala Met Ala Gln Val Lys Leu
                                20                  25                  30 cag gag tca ggg act gaa ctg gca aag cct ggg gcc gca gtg aag atg         144
Gln Glu Ser Gly Thr Glu Leu Ala Lys Pro Gly Ala Ala Val Lys Met
            35                  40                  45 tcc tgc aag gct tct ggc tac acc ttt act gac tac tgg atg cac tgg         192
Ser Cys Lys Ala Ser Gly Tyr Thr Phe Thr Asp Tyr Trp Met His Trp
        50                  55                  60 gtt aaa cag agg cct gga cag ggt ctg gaa tgg att gga tac att aat         240
Val Lys Gln Arg Pro Gly Gln Gly Leu Glu Trp Ile Gly Tyr Ile Asn
65                  70                  75                  80 cct aac act gct tat act gac tac aat cag aaa ttc aag gac aag gcc         288
Pro Asn Thr Ala Tyr Thr Asp Tyr Asn Gln Lys Phe Lys Asp Lys Ala
                85                  90                  95 aca ttg act gca gac aaa tcc tcc agc aca gcc tac atg caa ctg cgc         336
Thr Leu Thr Ala Asp Lys Ser Ser Ser Thr Ala Tyr Met Gln Leu Arg
            100                 105                 110 agc ctg acc tct gag gat tct gca gtc tat tac tgt gca aaa aag aca         384
Ser Leu Thr Ser Glu Asp Ser Ala Val Tyr Tyr Cys Ala Lys Lys Thr
        115                 120                 125 act cag act acg tgg ggg ttt cct ttt tgg ggc caa ggg acc acg gtc         432
Thr Gln Thr Thr Trp Gly Phe Pro Phe Trp Gly Gln Gly Thr Thr Val
130                 135                 140 acc gtc tcc tca ggt gga ggc ggt tca ggc gga ggt ggc tct ggc ggt         480
Thr Val Ser Ser Gly Gly Gly Gly Ser Gly Gly Gly Gly Ser Gly Gly
145                 150                 155                 160 ggc gga tcg gac att gtg ctg acc cag tct cca aaa tcc atg gcc atg         528
Gly Gly Ser Asp Ile Val Leu Thr Gln Ser Pro Lys Ser Met Ala Met
                165                 170                 175 tca gtc gga gag agg gtc acc ttg agc tgc aag gcc agt gag aat gtg         576
Ser Val Gly Glu Arg Val Thr Leu Ser Cys Lys Ala Ser Glu Asn Val
            180                 185                 190 gat tct ttt gtt tcc tgg tat caa cag aaa cca ggc cag tct cct aaa         624
Asp Ser Phe Val Ser Trp Tyr Gln Gln Lys Pro Gly Gln Ser Pro Lys
        195                 200                 205 ctg ctg ata tac ggg gcc tcc aac cgg tac act ggg gtc ccc gat cgc         672
Leu Leu Ile Tyr Gly Ala Ser Asn Arg Tyr Thr Gly Val Pro Asp Arg
210                 215                 220 ttc gca ggc agt gga tct gga aga gat ttc act ctg acc atc agc agt         720
Phe Ala Gly Ser Gly Ser Gly Arg Asp Phe Thr Leu Thr Ile Ser Ser
225                 230                 235                 240 gtg cag gct gaa gac ctt gca gat tat cac tgt gga cag aat tac agg         768
Val Gln Ala Glu Asp Leu Ala Asp Tyr His Cys Gly Gln Asn Tyr Arg
            245                 250                 255 tat ccg ctc acg ttc ggt gct ggc acc aag ctg gaa atc aaa cgg gcg         816
Tyr Pro Leu Thr Phe Gly Ala Gly Thr Lys Leu Glu Ile Lys Arg Ala
        260                 265                 270 gcc gca ctc gag tct aga atg gtc cag gcc tcg atg agg agc cca aat         864
Ala Ala Leu Glu Ser Arg Met Val Gln Ala Ser Met Arg Ser Pro Asn
275                 280                 285 atg gag acg ttc aaa cag cag aag gtg gag gac ttt tat gat att gga         912
Met Glu Thr Phe Lys Gln Gln Lys Val Glu Asp Phe Tyr Asp Ile Gly
            290                 295                 300 gag gag ctg ggc agt ggc cag ttt gcc atc gtg aag aag tgc cgg gag         960
Glu Glu Leu Gly Ser Gly Gln Phe Ala Ile Val Lys Lys Cys Arg Glu
305                 310                 315                 320 aag agc acg ggg ctg gag tat gca gcc aag ttc att aag aag agg cag         1008
Lys Ser Thr Gly Leu Glu Tyr Ala Ala Lys Phe Ile Lys Lys Arg Gln
                325                 330                 335
```

| | | |
|---|---|---|
| agc cgg gcc agc cgt cgg ggc gtg tgc cgg gag gaa atc gag cgg gag<br>Ser Arg Ala Ser Arg Arg Gly Val Cys Arg Glu Glu Ile Glu Arg Glu<br>340                                   345                           350 | 1056 | |
| gtg agc atc ctg cgg cag gtg ctg cac ccc aac atc atc acg ctg cac<br>Val Ser Ile Leu Arg Gln Val Leu His Pro Asn Ile Ile Thr Leu His<br>355                                   360                           365 | 1104 | |
| gac ctc tat gag aac cgc acc gac gtg gtg ctc atc ctt gag cta gtg<br>Asp Leu Tyr Glu Asn Arg Thr Asp Val Val Leu Ile Leu Glu Leu Val<br>370                                   375                         380 | 1152 | |
| tcc gga gga gaa ctg ttt gat ttc ctg gcc cag aag gag tcg tta agt<br>Ser Gly Gly Glu Leu Phe Asp Phe Leu Ala Gln Lys Glu Ser Leu Ser<br>385                                   390                         395              400 | 1200 | |
| gag gag gaa gcc acc agc ttc att aag cag atc ctg gat ggg gtg aat<br>Glu Glu Glu Ala Thr Ser Phe Ile Lys Gln Ile Leu Asp Gly Val Asn<br>                           405                         410                         415 | 1248 | |
| tac ctt cac aca aag aaa att gct cac ttt gat ctc aag cca gaa aac<br>Tyr Leu His Thr Lys Lys Ile Ala His Phe Asp Leu Lys Pro Glu Asn<br>                     420                         425                         430 | 1296 | |
| atc atg ttg tta gac aag aat atc cca att cca cac atc aag ctg att<br>Ile Met Leu Leu Asp Lys Asn Ile Pro Ile Pro His Ile Lys Leu Ile<br>               435                         440                         445 | 1344 | |
| gac ttt ggc ctg gct cac gaa ata gaa gat gga gtt gaa ttt aaa aac<br>Asp Phe Gly Leu Ala His Glu Ile Glu Asp Gly Val Glu Phe Lys Asn<br>450                                   455                         460 | 1392 | |
| att ttt ggg aca cct gaa ttt gtt gct cca gaa atc gtg aac tat gag<br>Ile Phe Gly Thr Pro Glu Phe Val Ala Pro Glu Ile Val Asn Tyr Glu<br>465                                   470                         475              480 | 1440 | |
| cca ctg gga ctg gag gcc gac atg tgg agc att gga gtc atc acc tat<br>Pro Leu Gly Leu Glu Ala Asp Met Trp Ser Ile Gly Val Ile Thr Tyr<br>                           485                         490                         495 | 1488 | |
| atc ctt cta agt gga gcg tcc ccc ttc ctg gga gac aca aaa caa gaa<br>Ile Leu Leu Ser Gly Ala Ser Pro Phe Leu Gly Asp Thr Lys Gln Glu<br>                   500                         505                         510 | 1536 | |
| acc ctg gca aat atc act gct gtg agt tac gac ttt gat gag gaa ttc<br>Thr Leu Ala Asn Ile Thr Ala Val Ser Tyr Asp Phe Asp Glu Glu Phe<br>               515                         520                         525 | 1584 | |
| ttc agc cag aca agc gag ctg gcc aag gac ttc att cgg aag ctt ctt<br>Phe Ser Gln Thr Ser Glu Leu Ala Lys Asp Phe Ile Arg Lys Leu Leu<br>530                                   535                         540 | 1632 | |
| gtg aaa gag acc cgg aaa cgg ctt acc atc caa gag gct ctc aga cat<br>Val Lys Glu Thr Arg Lys Arg Leu Thr Ile Gln Glu Ala Leu Arg His<br>545                                   550                         555              560 | 1680 | |
| ccc tgg atc gga tcc aaa cta gct gag cac gaa ttt cga gga ggg ccc<br>Pro Trp Ile Gly Ser Lys Leu Ala Glu His Glu Phe Arg Gly Gly Pro<br>                   565                         570                         575 | 1728 | |
| gaa caa aaa ctc atc tca gaa gag gat ctg aat agc gcc gtc gac cat<br>Glu Gln Lys Leu Ile Ser Glu Glu Asp Leu Asn Ser Ala Val Asp His<br>                       580                         585                         590 | 1776 | |
| cat cat cat cat cat tga<br>His His His His His<br>             595 | 1794 | |

<210> SEQ ID NO 4
<211> LENGTH: 597
<212> TYPE: PRT
<213> ORGANISM: Artificial Sequence
<220> FEATURE:
<223> OTHER INFORMATION: Synthetic Construct

<400> SEQUENCE: 4

Met Glu Thr Asp Thr Leu Leu Leu Trp Val Leu Leu Leu Trp Val Pro

-continued

```
1               5                   10                  15
Gly Ser Thr Gly Asp Ala Ala Gln Pro Ala Met Ala Gln Val Lys Leu
            20                  25                  30
Gln Glu Ser Gly Thr Glu Leu Ala Lys Pro Gly Ala Ala Val Lys Met
            35                  40                  45
Ser Cys Lys Ala Ser Gly Tyr Thr Phe Thr Asp Tyr Trp Met His Trp
 50                      55                  60
Val Lys Gln Arg Pro Gly Gln Gly Leu Glu Trp Ile Gly Tyr Ile Asn
 65                  70                  75                  80
Pro Asn Thr Ala Tyr Thr Asp Tyr Asn Gln Lys Phe Lys Asp Lys Ala
                85                  90                  95
Thr Leu Thr Ala Asp Lys Ser Ser Thr Ala Tyr Met Gln Leu Arg
                100                 105                 110
Ser Leu Thr Ser Glu Asp Ser Ala Val Tyr Tyr Cys Ala Lys Lys Thr
            115                 120                 125
Thr Gln Thr Thr Trp Gly Phe Pro Phe Trp Gly Gln Gly Thr Thr Val
            130                 135                 140
Thr Val Ser Ser Gly Gly Gly Ser Gly Gly Gly Ser Gly Gly
 145                     150                 155                 160
Gly Gly Ser Asp Ile Val Leu Thr Gln Ser Pro Lys Ser Met Ala Met
                165                 170                 175
Ser Val Gly Glu Arg Val Thr Leu Ser Cys Lys Ala Ser Glu Asn Val
            180                 185                 190
Asp Ser Phe Val Ser Trp Tyr Gln Gln Lys Pro Gly Gln Ser Pro Lys
            195                 200                 205
Leu Leu Ile Tyr Gly Ala Ser Asn Arg Tyr Thr Gly Val Pro Asp Arg
 210                     215                 220
Phe Ala Gly Ser Gly Ser Gly Arg Asp Phe Thr Leu Thr Ile Ser Ser
 225                     230                 235                 240
Val Gln Ala Glu Asp Leu Ala Asp Tyr His Cys Gly Gln Asn Tyr Arg
            245                 250                 255
Tyr Pro Leu Thr Phe Gly Ala Gly Thr Lys Leu Glu Ile Lys Arg Ala
                260                 265                 270
Ala Ala Leu Glu Ser Arg Met Val Gln Ala Ser Met Arg Ser Pro Asn
            275                 280                 285
Met Glu Thr Phe Lys Gln Gln Lys Val Glu Asp Phe Tyr Asp Ile Gly
            290                 295                 300
Glu Glu Leu Gly Ser Gly Gln Phe Ala Ile Val Lys Lys Cys Arg Glu
 305                     310                 315                 320
Lys Ser Thr Gly Leu Glu Tyr Ala Ala Lys Phe Ile Lys Lys Arg Gln
                325                 330                 335
Ser Arg Ala Ser Arg Arg Gly Val Cys Arg Glu Glu Ile Glu Arg Glu
            340                 345                 350
Val Ser Ile Leu Arg Gln Val Leu His Pro Asn Ile Ile Thr Leu His
            355                 360                 365
Asp Leu Tyr Glu Asn Arg Thr Asp Val Val Leu Ile Leu Glu Leu Val
 370                 375                 380
Ser Gly Gly Glu Leu Phe Asp Phe Leu Ala Gln Lys Glu Ser Leu Ser
 385                     390                 395                 400
Glu Glu Glu Ala Thr Ser Phe Ile Lys Gln Ile Leu Asp Gly Val Asn
                405                 410                 415
Tyr Leu His Thr Lys Lys Ile Ala His Phe Asp Leu Lys Pro Glu Asn
                420                 425                 430
```

```
Ile Met Leu Leu Asp Lys Asn Ile Pro Ile Pro His Ile Lys Leu Ile
            435                 440                 445

Asp Phe Gly Leu Ala His Glu Ile Glu Asp Gly Val Glu Phe Lys Asn
450                 455                 460

Ile Phe Gly Thr Pro Glu Phe Val Ala Pro Glu Ile Val Asn Tyr Glu
465                 470                 475                 480

Pro Leu Gly Leu Glu Ala Asp Met Trp Ser Ile Gly Val Ile Thr Tyr
                485                 490                 495

Ile Leu Leu Ser Gly Ala Ser Pro Phe Leu Gly Asp Thr Lys Gln Glu
            500                 505                 510

Thr Leu Ala Asn Ile Thr Ala Val Ser Tyr Asp Phe Asp Glu Glu Phe
            515                 520                 525

Phe Ser Gln Thr Ser Glu Leu Ala Lys Asp Phe Ile Arg Lys Leu Leu
        530                 535                 540

Val Lys Glu Thr Arg Lys Arg Leu Thr Ile Gln Glu Ala Leu Arg His
545                 550                 555                 560

Pro Trp Ile Gly Ser Lys Leu Ala Glu His Glu Phe Arg Gly Gly Pro
                565                 570                 575

Glu Gln Lys Leu Ile Ser Glu Glu Asp Leu Asn Ser Ala Val Asp His
            580                 585                 590

His His His His His
        595

<210> SEQ ID NO 5
<211> LENGTH: 3102
<212> TYPE: DNA
<213> ORGANISM: Artificial Sequence
<220> FEATURE:
<223> OTHER INFORMATION: pMT-Ki-4 (scFv)-eEF-2K ORF
<220> FEATURE:
<221> NAME/KEY: CDS
<222> LOCATION: (1)..(3102)
<220> FEATURE:
<221> NAME/KEY: N_region
<222> LOCATION: (2)..(22)
<223> OTHER INFORMATION: pelB leader sequence

<400> SEQUENCE: 5 atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
1               5                   10                  15 gcc cag ccg gcg atg gcc atg ggc cat cat cat cat cat cat cat          96
Ala Gln Pro Ala Met Ala Met Gly His His His His His His His
                20                  25                  30 cat cac agc agc ggc cat atc gac gac gac gac aag cat atg aag ctt     144
His His Ser Ser Gly His Ile Asp Asp Asp Asp Lys His Met Lys Leu
            35                  40                  45 atg gcc cag ccg gcc atg gcc cag gtc aag ctg cag gag tca ggg act     192
Met Ala Gln Pro Ala Met Ala Gln Val Lys Leu Gln Glu Ser Gly Thr
        50                  55                  60 gaa ctg gca aag cct ggg gcc gca gtg aag atg tcc tgc aag gct tct     240
Glu Leu Ala Lys Pro Gly Ala Ala Val Lys Met Ser Cys Lys Ala Ser
65                  70                  75                  80 ggc tac acc ttt act gac tac tgg atg cac tgg gtt aaa cag agg cct     288
Gly Tyr Thr Phe Thr Asp Tyr Trp Met His Trp Val Lys Gln Arg Pro
                85                  90                  95 gga cag ggt ctg gaa tgg att gga tac att aat cct aac act gct tat     336
Gly Gln Gly Leu Glu Trp Ile Gly Tyr Ile Asn Pro Asn Thr Ala Tyr
                100                 105                 110
```

```
act gac tac aat cag aaa ttc aag gac aag gcc aca ttg act gca gac     384
Thr Asp Tyr Asn Gln Lys Phe Lys Asp Lys Ala Thr Leu Thr Ala Asp
        115                 120                 125 aaa tcc tcc agc aca gcc tac atg caa ctg cgc agc ctg acc tct gag     432
Lys Ser Ser Ser Thr Ala Tyr Met Gln Leu Arg Ser Leu Thr Ser Glu
130                 135                 140 gat tct gca gtc tat tac tgt gca aaa aag aca act cag act acg tgg     480
Asp Ser Ala Val Tyr Tyr Cys Ala Lys Lys Thr Thr Gln Thr Thr Trp
145                 150                 155                 160 ggg ttt cct ttt tgg ggc caa ggg acc acg gtc acc gtc tcc tca ggt     528
Gly Phe Pro Phe Trp Gly Gln Gly Thr Thr Val Thr Val Ser Ser Gly
                165                 170                 175 gga ggc ggt tca ggc gga ggt ggc tct ggc ggt ggc gga tcg gac att     576
Gly Gly Gly Ser Gly Gly Gly Gly Ser Gly Gly Gly Gly Ser Asp Ile
            180                 185                 190 gtg ctg acc cag tct cca aaa tcc atg gcc atg tca gtc gga gag agg     624
Val Leu Thr Gln Ser Pro Lys Ser Met Ala Met Ser Val Gly Glu Arg
                195                 200                 205 gtc acc ttg agc tgc aag gcc agt gag aat gtg gat tct ttt gtt tcc     672
Val Thr Leu Ser Cys Lys Ala Ser Glu Asn Val Asp Ser Phe Val Ser
210                 215                 220 tgg tat caa cag aaa cca ggc cag tct cct aaa ctg ctg ata tac ggg     720
Trp Tyr Gln Gln Lys Pro Gly Gln Ser Pro Lys Leu Leu Ile Tyr Gly
225                 230                 235                 240 gcc tcc aac cgg tac act ggg gtc ccc gat cgc ttc gca ggc agt gga     768
Ala Ser Asn Arg Tyr Thr Gly Val Pro Asp Arg Phe Ala Gly Ser Gly
                245                 250                 255 tct gga aga gat ttc act ctg acc atc agc agt gtg cag gct gaa gac     816
Ser Gly Arg Asp Phe Thr Leu Thr Ile Ser Ser Val Gln Ala Glu Asp
            260                 265                 270 ctt gca gat tat cac tgt gga cag aat tac agg tat ccg ctc acg ttc     864
Leu Ala Asp Tyr His Cys Gly Gln Asn Tyr Arg Tyr Pro Leu Thr Phe
                275                 280                 285 ggt gct ggc acc aag ctg gaa atc aaa cgg gcg gcc gca gag ctc ggc     912
Gly Ala Gly Thr Lys Leu Glu Ile Lys Arg Ala Ala Ala Glu Leu Gly
        290                 295                 300 gga ggt ggc tct atg gca gac gaa gat ctc atc ttc cgc ctg gaa ggc     960
Gly Gly Gly Ser Met Ala Asp Glu Asp Leu Ile Phe Arg Leu Glu Gly
305                 310                 315                 320 gtt gat ggc ggc cag tcc ccc cga gct ggc cat gat ggt gat tct gat    1008
Val Asp Gly Gly Gln Ser Pro Arg Ala Gly His Asp Gly Asp Ser Asp
                325                 330                 335 ggg gac agc gac gat gag gaa ggt tac ttc atc tgc ccc atc acg gat    1056
Gly Asp Ser Asp Asp Glu Glu Gly Tyr Phe Ile Cys Pro Ile Thr Asp
            340                 345                 350 gac cca agc tcg aac cag aat gtc aat tcc aag gtt aat aag tac tac    1104
Asp Pro Ser Ser Asn Gln Asn Val Asn Ser Lys Val Asn Lys Tyr Tyr
                355                 360                 365 agc aac cta aca aaa agt gag cgg tat agc tcc agc ggg tcc ccg gca    1152
Ser Asn Leu Thr Lys Ser Glu Arg Tyr Ser Ser Ser Gly Ser Pro Ala
        370                 375                 380 aac tcc ttc cac ttc aag gaa gcc tgg aag cac gca atc cag aag gcc    1200
Asn Ser Phe His Phe Lys Glu Ala Trp Lys His Ala Ile Gln Lys Ala
385                 390                 395                 400 aag cac atg ccc gac ccc tgg gct gag ttc cac ctg gaa gat att gcc    1248
Lys His Met Pro Asp Pro Trp Ala Glu Phe His Leu Glu Asp Ile Ala
                405                 410                 415 acc gaa cgt gct act cga cac agg tac aac gcc gtc acc ggg gaa tgg    1296
Thr Glu Arg Ala Thr Arg His Arg Tyr Asn Ala Val Thr Gly Glu Trp
            420                 425                 430
```

-continued

| | |
|---|---|
| ctg gat gat gaa gtt ctg atc aag atg gca tct cag ccc ttc ggc cga<br>Leu Asp Asp Glu Val Leu Ile Lys Met Ala Ser Gln Pro Phe Gly Arg<br>435                      440                      445 | 1344 |
| gga gca atg agg gag tgc ttc cgg acg aag aag ctc tcc aac ttc ttg<br>Gly Ala Met Arg Glu Cys Phe Arg Thr Lys Lys Leu Ser Asn Phe Leu<br>    450                      455                      460 | 1392 |
| cat gcc cag cag tgg aag ggc gcc tcc aac tac gtg gcg aag cgc tac<br>His Ala Gln Gln Trp Lys Gly Ala Ser Asn Tyr Val Ala Lys Arg Tyr<br>465                      470                      475                      480 | 1440 |
| atc gag ccc gta gac cgg gat gtg tac ttt gag gac gtg cgt cta cag<br>Ile Glu Pro Val Asp Arg Asp Val Tyr Phe Glu Asp Val Arg Leu Gln<br>                      485                      490                      495 | 1488 |
| atg gag gcc aag ctc tgg ggg gag gag tat aat cgg cac aag ccc ccc<br>Met Glu Ala Lys Leu Trp Gly Glu Glu Tyr Asn Arg His Lys Pro Pro<br>500                      505                      510 | 1536 |
| aag cag gtg gac atc atg cag atg tgc atc atc gag ctg aag gac aga<br>Lys Gln Val Asp Ile Met Gln Met Cys Ile Ile Glu Leu Lys Asp Arg<br>                515                      520                      525 | 1584 |
| ccg ggc aag ccc ctc ttc cac ctg gag cac tac atc gag ggc aag tac<br>Pro Gly Lys Pro Leu Phe His Leu Glu His Tyr Ile Glu Gly Lys Tyr<br>530                      535                      540 | 1632 |
| atc aag tac aac tcc aac tct ggc ttt gtc cgc gat gac aac atc cgc<br>Ile Lys Tyr Asn Ser Asn Ser Gly Phe Val Arg Asp Asp Asn Ile Arg<br>545                      550                      555                      560 | 1680 |
| ctg acg ccg cag gcc ttc agc cac ttc act ttt gag cgt tcc ggc cat<br>Leu Thr Pro Gln Ala Phe Ser His Phe Thr Phe Glu Arg Ser Gly His<br>                      565                      570                      575 | 1728 |
| cag ctg ata gtg gtg gac atc cag gga gtt ggg gat ctc tac act gac<br>Gln Leu Ile Val Val Asp Ile Gln Gly Val Gly Asp Leu Tyr Thr Asp<br>580                      585                      590 | 1776 |
| cca cag atc cac acg gag acg ggc act gac ttt gga gac ggc aac cta<br>Pro Gln Ile His Thr Glu Thr Gly Thr Asp Phe Gly Asp Gly Asn Leu<br>595                      600                      605 | 1824 |
| ggt gtc cgc ggg atg gcg ctc ttc ttc tac tct cat gcc tgc aac cgg<br>Gly Val Arg Gly Met Ala Leu Phe Phe Tyr Ser His Ala Cys Asn Arg<br>    610                      615                      620 | 1872 |
| att tgc gag agc atg ggc ctt gct ccc ttt gac ctc tcg ccc cgg gag<br>Ile Cys Glu Ser Met Gly Leu Ala Pro Phe Asp Leu Ser Pro Arg Glu<br>625                      630                      635                      640 | 1920 |
| agg gat gca gtg aat cag aac acc aag ctg ctg caa tca gcc aag acc<br>Arg Asp Ala Val Asn Gln Asn Thr Lys Leu Leu Gln Ser Ala Lys Thr<br>                      645                      650                      655 | 1968 |
| atc ttg aga gga aca gag gaa aaa tgt ggg agc ccc cga gta agg acc<br>Ile Leu Arg Gly Thr Glu Glu Lys Cys Gly Ser Pro Arg Val Arg Thr<br>660                      665                      670 | 2016 |
| ctc tct ggg agc cgg cca ccc ctg ctc cgt ccc ctt tca gag aac tct<br>Leu Ser Gly Ser Arg Pro Pro Leu Leu Arg Pro Leu Ser Glu Asn Ser<br>                675                      680                      685 | 2064 |
| gga gac gag aac atg agc gac gtg acc ttc gac tct ctc cct tct tcc<br>Gly Asp Glu Asn Met Ser Asp Val Thr Phe Asp Ser Leu Pro Ser Ser<br>690                      695                      700 | 2112 |
| cca tct tcg gcc aca cca cac agc cag aag cta gac cac ctc cat tgg<br>Pro Ser Ser Ala Thr Pro His Ser Gln Lys Leu Asp His Leu His Trp<br>705                      710                      715                      720 | 2160 |
| cca gtc ttc agt gac ctc gat aac atg gca tcc aga gac cat gat cat<br>Pro Val Phe Ser Asp Leu Asp Asn Met Ala Ser Arg Asp His Asp His<br>                      725                      730                      735 | 2208 |
| cta gac aac cac cgg gag tct gag aat agt ggg gac agc gga tac ccc<br>Leu Asp Asn His Arg Glu Ser Glu Asn Ser Gly Asp Ser Gly Tyr Pro | 2256 |

-continued

```
                    740                     745                     750
agt gag aag cgg ggt gag ctg gat gac cct gag ccc cga gaa cat ggc        2304
Ser Glu Lys Arg Gly Glu Leu Asp Asp Pro Glu Pro Arg Glu His Gly
        755                     760                     765 cac tca tac agt aat cgg aag tac gag tct gac gaa gac agc ctg ggc        2352
His Ser Tyr Ser Asn Arg Lys Tyr Glu Ser Asp Glu Asp Ser Leu Gly
770                     775                     780 agc tct gga cgg gta tgt gta gag aag tgg aat ctc ctc aac tcc tcc        2400
Ser Ser Gly Arg Val Cys Val Glu Lys Trp Asn Leu Leu Asn Ser Ser
785                     790                     795                 800 cgc ctc cac ctg ccg agg gct tcg gcc gtg gcc ctg gaa gtc caa agg        2448
Arg Leu His Leu Pro Arg Ala Ser Ala Val Ala Leu Glu Val Gln Arg
            805                     810                     815 ctt aat gct ctg gac ctc gaa aag aaa atc ggg aag tcc att ttg ggg        2496
Leu Asn Ala Leu Asp Leu Glu Lys Lys Ile Gly Lys Ser Ile Leu Gly
        820                     825                     830 aag gtc cat ctg gcc atg gtg cgc tac cac gag ggt ggg cgc ttc tgc        2544
Lys Val His Leu Ala Met Val Arg Tyr His Glu Gly Gly Arg Phe Cys
    835                     840                     845 gag aag ggc gag gag tgg gac cag gag tcg gct gtc ttc cac ctg gag        2592
Glu Lys Gly Glu Glu Trp Asp Gln Glu Ser Ala Val Phe His Leu Glu
850                     855                     860 cac gca gcc aac ctg ggc gag ctg gag gcc atc gtg ggc ctg gga ctc        2640
His Ala Ala Asn Leu Gly Glu Leu Glu Ala Ile Val Gly Leu Gly Leu
865                     870                     875                 880 atg tac tcg cag ttg cct cat cac atc cta gcc gat gtc tct ctg aag        2688
Met Tyr Ser Gln Leu Pro His His Ile Leu Ala Asp Val Ser Leu Lys
            885                     890                     895 gag aca gaa gag aac aaa acc aaa gga ttt gat tac tta cta aag gcc        2736
Glu Thr Glu Glu Asn Lys Thr Lys Gly Phe Asp Tyr Leu Leu Lys Ala
        900                     905                     910 gct gaa gct ggc gac agg cag tcc atg atc cta gtg gcg cga gct ttt        2784
Ala Glu Ala Gly Asp Arg Gln Ser Met Ile Leu Val Ala Arg Ala Phe
    915                     920                     925 gac tct ggc cag aac ctc agc ccg gac agg tgc caa gac tgg cta gag        2832
Asp Ser Gly Gln Asn Leu Ser Pro Asp Arg Cys Gln Asp Trp Leu Glu
930                     935                     940 gcc ctg cac tgg tac aac act gcc ctg gag atg acg gac tgt gat gag        2880
Ala Leu His Trp Tyr Asn Thr Ala Leu Glu Met Thr Asp Cys Asp Glu
945                     950                     955                 960 ggc ggt gag tac gac gga atg cag gac gag ccc cgg tac atg atg ctg        2928
Gly Gly Glu Tyr Asp Gly Met Gln Asp Glu Pro Arg Tyr Met Met Leu
            965                     970                     975 gcc agg gag gcc gag atg ctg ttc aca gga ggc tac ggg ctg gag aag        2976
Ala Arg Glu Ala Glu Met Leu Phe Thr Gly Gly Tyr Gly Leu Glu Lys
        980                     985                     990 gac ccg cag aga tca ggg gac ttg tat acc cag gca gca gag gca gcg        3024
Asp Pro Gln Arg Ser Gly Asp Leu Tyr Thr Gln Ala Ala Glu Ala Ala
    995                     1000                    1005 atg gaa gcc atg aag ggc cga ctg gcc aac cag tac tac caa aag          3069
Met Glu Ala Met Lys Gly Arg Leu Ala Asn Gln Tyr Tyr Gln Lys
    1010                    1015                    1020 gct gaa gag gcc tgg gcc cag atg gag gag taa                          3102
Ala Glu Glu Ala Trp Ala Gln Met Glu Glu
1025                    1030

<210> SEQ ID NO 6
<211> LENGTH: 1033
<212> TYPE: PRT
<213> ORGANISM: Artificial Sequence
```

<220> FEATURE:
<223> OTHER INFORMATION: Synthetic Construct

<400> SEQUENCE: 6

```
Met Lys Tyr Leu Leu Pro Thr Ala Ala Ala Gly Leu Leu Leu Leu Ala
1               5                   10                  15

Ala Gln Pro Ala Met Ala Met Gly His His His His His His
            20              25                  30

His His Ser Ser Gly His Ile Asp Asp Asp Lys His Met Lys Leu
        35                  40                  45

Met Ala Gln Pro Ala Met Ala Gln Val Lys Leu Gln Glu Ser Gly Thr
50                  55                  60

Glu Leu Ala Lys Pro Gly Ala Ala Val Lys Met Ser Cys Lys Ala Ser
65                  70                  75                  80

Gly Tyr Thr Phe Thr Asp Tyr Trp Met His Trp Val Lys Gln Arg Pro
                85                  90                  95

Gly Gln Gly Leu Glu Trp Ile Gly Tyr Ile Asn Pro Asn Thr Ala Tyr
            100                 105                 110

Thr Asp Tyr Asn Gln Lys Phe Lys Asp Lys Ala Thr Leu Thr Ala Asp
        115                 120                 125

Lys Ser Ser Ser Thr Ala Tyr Met Gln Leu Arg Ser Leu Thr Ser Glu
130                 135                 140

Asp Ser Ala Val Tyr Tyr Cys Ala Lys Lys Thr Thr Gln Thr Thr Trp
145                 150                 155                 160

Gly Phe Pro Phe Trp Gly Gln Gly Thr Thr Val Thr Val Ser Ser Gly
                165                 170                 175

Gly Gly Gly Ser Gly Gly Gly Gly Ser Gly Gly Gly Ser Asp Ile
            180                 185                 190

Val Leu Thr Gln Ser Pro Lys Ser Met Ala Met Ser Val Gly Glu Arg
        195                 200                 205

Val Thr Leu Ser Cys Lys Ala Ser Glu Asn Val Asp Ser Phe Val Ser
210                 215                 220

Trp Tyr Gln Gln Lys Pro Gly Gln Ser Pro Lys Leu Leu Ile Tyr Gly
225                 230                 235                 240

Ala Ser Asn Arg Tyr Thr Gly Val Pro Asp Arg Phe Ala Gly Ser Gly
                245                 250                 255

Ser Gly Arg Asp Phe Thr Leu Thr Ile Ser Ser Val Gln Ala Glu Asp
            260                 265                 270

Leu Ala Asp Tyr His Cys Gly Gln Asn Tyr Arg Tyr Pro Leu Thr Phe
        275                 280                 285

Gly Ala Gly Thr Lys Leu Glu Ile Lys Arg Ala Ala Ala Glu Leu Gly
290                 295                 300

Gly Gly Gly Ser Met Ala Asp Glu Asp Leu Ile Phe Arg Leu Glu Gly
305                 310                 315                 320

Val Asp Gly Gly Gln Ser Pro Arg Ala Gly His Asp Gly Asp Ser Asp
                325                 330                 335

Gly Asp Ser Asp Asp Glu Glu Gly Tyr Phe Ile Cys Pro Ile Thr Asp
            340                 345                 350

Asp Pro Ser Ser Asn Gln Asn Val Asn Ser Lys Val Asn Lys Tyr Tyr
        355                 360                 365

Ser Asn Leu Thr Lys Ser Glu Arg Tyr Ser Ser Ser Gly Ser Pro Ala
370                 375                 380

Asn Ser Phe His Phe Lys Glu Ala Trp Lys His Ala Ile Gln Lys Ala
385                 390                 395                 400
```

```
Lys His Met Pro Asp Pro Trp Ala Glu Phe His Leu Glu Asp Ile Ala
                405                 410                 415
Thr Glu Arg Ala Thr Arg His Arg Tyr Asn Ala Val Thr Gly Glu Trp
            420                 425                 430
Leu Asp Asp Glu Val Leu Ile Lys Met Ala Ser Gln Pro Phe Gly Arg
                435                 440                 445
Gly Ala Met Arg Glu Cys Phe Arg Thr Lys Lys Leu Ser Asn Phe Leu
        450                 455                 460
His Ala Gln Gln Trp Lys Gly Ala Ser Asn Tyr Val Ala Lys Arg Tyr
465                 470                 475                 480
Ile Glu Pro Val Asp Arg Asp Val Tyr Phe Glu Asp Val Arg Leu Gln
                485                 490                 495
Met Glu Ala Lys Leu Trp Gly Glu Glu Tyr Asn Arg His Lys Pro Pro
            500                 505                 510
Lys Gln Val Asp Ile Met Gln Met Cys Ile Ile Glu Leu Lys Asp Arg
                515                 520                 525
Pro Gly Lys Pro Leu Phe His Leu Glu His Tyr Ile Glu Gly Lys Tyr
        530                 535                 540
Ile Lys Tyr Asn Ser Asn Ser Gly Phe Val Arg Asp Asp Asn Ile Arg
545                 550                 555                 560
Leu Thr Pro Gln Ala Phe Ser His Phe Thr Phe Glu Arg Ser Gly His
                565                 570                 575
Gln Leu Ile Val Val Asp Ile Gln Gly Val Gly Asp Leu Tyr Thr Asp
                580                 585                 590
Pro Gln Ile His Thr Glu Thr Gly Thr Asp Phe Gly Asp Gly Asn Leu
        595                 600                 605
Gly Val Arg Gly Met Ala Leu Phe Phe Tyr Ser His Ala Cys Asn Arg
        610                 615                 620
Ile Cys Glu Ser Met Gly Leu Ala Pro Phe Asp Leu Ser Pro Arg Glu
625                 630                 635                 640
Arg Asp Ala Val Asn Gln Asn Thr Lys Leu Leu Gln Ser Ala Lys Thr
                645                 650                 655
Ile Leu Arg Gly Thr Glu Glu Lys Cys Gly Ser Pro Arg Val Arg Thr
                660                 665                 670
Leu Ser Gly Ser Arg Pro Pro Leu Leu Arg Pro Leu Ser Glu Asn Ser
        675                 680                 685
Gly Asp Glu Asn Met Ser Asp Val Thr Phe Asp Ser Leu Pro Ser Ser
        690                 695                 700
Pro Ser Ser Ala Thr Pro His Ser Gln Lys Leu Asp His Leu His Trp
705                 710                 715                 720
Pro Val Phe Ser Asp Leu Asp Asn Met Ala Ser Arg Asp His Asp His
                725                 730                 735
Leu Asp Asn His Arg Glu Ser Glu Asn Ser Gly Asp Ser Gly Tyr Pro
                740                 745                 750
Ser Glu Lys Arg Gly Glu Leu Asp Asp Pro Glu Pro Arg Glu His Gly
        755                 760                 765
His Ser Tyr Ser Asn Arg Lys Tyr Glu Ser Asp Glu Asp Ser Leu Gly
        770                 775                 780
Ser Ser Gly Arg Val Cys Val Glu Lys Trp Asn Leu Leu Asn Ser Ser
785                 790                 795                 800
Arg Leu His Leu Pro Arg Ala Ser Ala Val Ala Leu Glu Val Gln Arg
                805                 810                 815
```

-continued

Leu Asn Ala Leu Asp Leu Glu Lys Lys Ile Gly Lys Ser Ile Leu Gly
             820                 825                 830

Lys Val His Leu Ala Met Val Arg Tyr His Glu Gly Gly Arg Phe Cys
             835                 840                 845

Glu Lys Gly Glu Glu Trp Asp Gln Glu Ser Ala Val Phe His Leu Glu
     850                 855                 860

His Ala Ala Asn Leu Gly Glu Leu Glu Ala Ile Val Gly Leu Gly Leu
865                 870                 875                 880

Met Tyr Ser Gln Leu Pro His His Ile Leu Ala Asp Val Ser Leu Lys
                 885                 890                 895

Glu Thr Glu Glu Asn Lys Thr Lys Gly Phe Asp Tyr Leu Leu Lys Ala
             900                 905                 910

Ala Glu Ala Gly Asp Arg Gln Ser Met Ile Leu Val Ala Arg Ala Phe
         915                 920                 925

Asp Ser Gly Gln Asn Leu Ser Pro Asp Arg Cys Gln Asp Trp Leu Glu
     930                 935                 940

Ala Leu His Trp Tyr Asn Thr Ala Leu Glu Met Thr Asp Cys Asp Glu
945                 950                 955                 960

Gly Gly Glu Tyr Asp Gly Met Gln Asp Glu Pro Arg Tyr Met Met Leu
                965                 970                 975

Ala Arg Glu Ala Glu Met Leu Phe Thr Gly Gly Tyr Gly Leu Glu Lys
             980                 985                 990

Asp Pro Gln Arg Ser Gly Asp Leu Tyr Thr Gln Ala Ala Glu Ala Ala
         995                 1000                1005

Met Glu Ala Met Lys Gly Arg Leu Ala Asn Gln Tyr Tyr Gln Lys
     1010                1015                1020

Ala Glu Glu Ala Trp Ala Gln Met Glu Glu
     1025                1030

<210> SEQ ID NO 7
<211> LENGTH: 15
<212> TYPE: PRT
<213> ORGANISM: Artificial Sequence
<220> FEATURE:
<223> OTHER INFORMATION: synthetic linker

<400> SEQUENCE: 7

Gly Gly Gly Gly Ser Gly Gly Gly Gly Ser Gly Gly Gly Gly Ser
1               5                  10                  15

<210> SEQ ID NO 8
<211> LENGTH: 10
<212> TYPE: PRT
<213> ORGANISM: Artificial Sequence
<220> FEATURE:
<223> OTHER INFORMATION: c-Myc epitope

<400> SEQUENCE: 8

Glu Gln Lys Leu Ile Ser Glu Glu Asp Leu
1               5                  10

<210> SEQ ID NO 9
<211> LENGTH: 6
<212> TYPE: PRT
<213> ORGANISM: Artificial Sequence
<220> FEATURE:
<223> OTHER INFORMATION: motif in domain IX of kinases
<220> FEATURE:
<221> NAME/KEY: Variant
<222> LOCATION: (2)..(2)
<223> OTHER INFORMATION: Xaa is any amino acid -continued

```
<220> FEATURE:
<221> NAME/KEY: Variant
<222> LOCATION: (4)..(5)
<223> OTHER INFORMATION: Xaa is any amino acid

<400> SEQUENCE: 9

Asp Xaa Trp Xaa Xaa Gly
  1               5
```